US006544257B2

United States Patent
Nagase et al.

(10) Patent No.: US 6,544,257 B2
(45) Date of Patent: Apr. 8, 2003

(54) THERMAL TREATMENT APPARATUS

(75) Inventors: Toru Nagase, Tokyo (JP); Norihiko Hareyama, Tokyo (JP); Takefumi Uesugi, Tokyo (JP); Satoshi Mizukawa, Tokyo (JP); Makoto Inaba, Tokyo (JP); Akira Sakaguchi, Kanagawa (JP); Shigenobu Iwahashi, Kanagawa (JP); Shigeki Ariura, Kanagawa (JP); Shin Maki, Kanagawa (JP); Wataru Karino, Kanagawa (JP)

(73) Assignees: Olympus Optical Co., Ltd., Tokyo (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/895,259

(22) Filed: Jul. 2, 2001

(65) Prior Publication Data

US 2002/0022829 A1 Feb. 21, 2002

(30) Foreign Application Priority Data

Jul. 3, 2000 (JP) .......................................... 2000-201644

(51) Int. Cl.$^7$ ............................................... A61B 18/18
(52) U.S. Cl. .............................. 606/15; 606/11; 606/18; 606/19; 607/89
(58) Field of Search ........................ 607/88–93; 606/10, 606/11, 15, 13, 14, 18, 19

(56) References Cited

U.S. PATENT DOCUMENTS

| 4,932,956 | A |   | 6/1990 | Reddy et al. |
|---|---|---|---|---|
| 5,207,672 | A |   | 5/1993 | Roth et al. |
| 5,292,320 | A |   | 3/1994 | Brown et al. |
| 5,387,211 | A | * | 2/1995 | Saadatmanesh et al. ...... 606/10 |
| 5,496,308 | A |   | 3/1996 | Brown et al. |
| 5,860,967 | A | * | 1/1999 | Zavislan et al. .............. 606/10 |
| 6,379,347 | B1 | * | 4/2002 | Maki et al. .................... 606/17 |

FOREIGN PATENT DOCUMENTS

| EP | 0 673 627 A1 | 9/1995 |
|---|---|---|
| EP | 0 947 221 A2 | 10/1999 |
| EP | 0 960 601 A2 | 12/1999 |
| WO | WO 92/04934 A1 | 4/1992 |
| WO | WO 93/04727 A1 | 3/1993 |

* cited by examiner

Primary Examiner—Michael Peffley
Assistant Examiner—H. M. Johnson
(74) Attorney, Agent, or Firm—Burns, Doane, Swecker & Mathis, LLP

(57) ABSTRACT

A thermal treatment apparatus comprises a control unit 251a that stops issuing a signal for laser beam activation transmitted over the foot switch signal cable 291 when the temperature obtained by the mirror temperature sensor 111 that detects the temperature of the laser emission part 122 provided at the laser irradiation unit 1 exceeds a predetermined value. This stops the output of the laser beam from the laser generator 3. Alternatively, the control unit can adjust the output value of the laser beam generated by the laser beam generator 3 by transmitting a signal via the communication cable 293 to change it in accordance with the detection signal of the mirror temperature sensor 111.

25 Claims, 36 Drawing Sheets

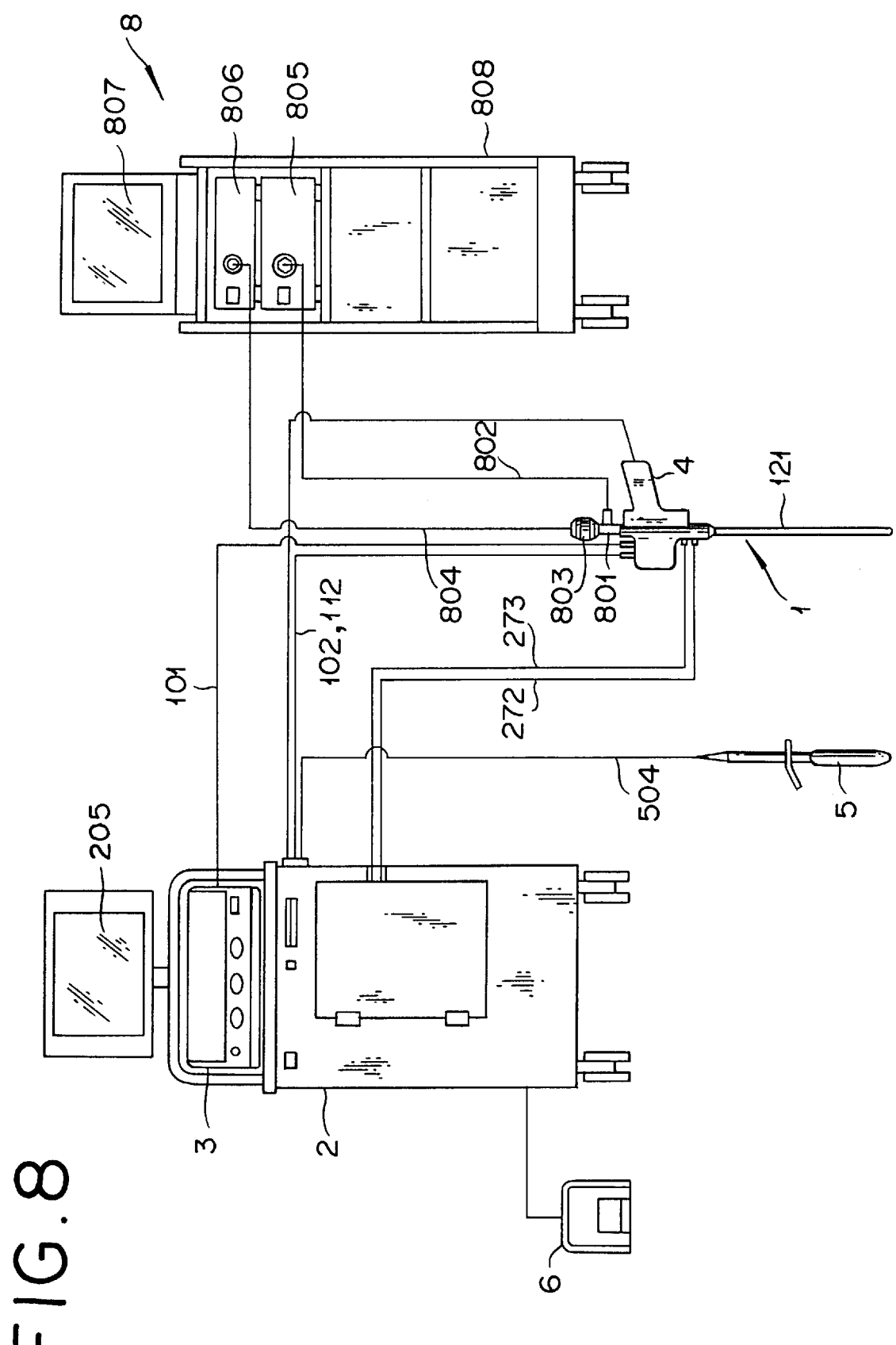

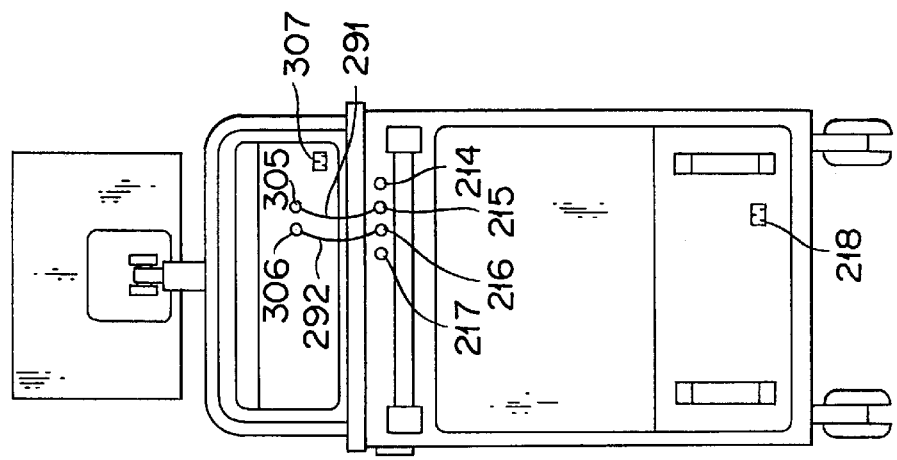
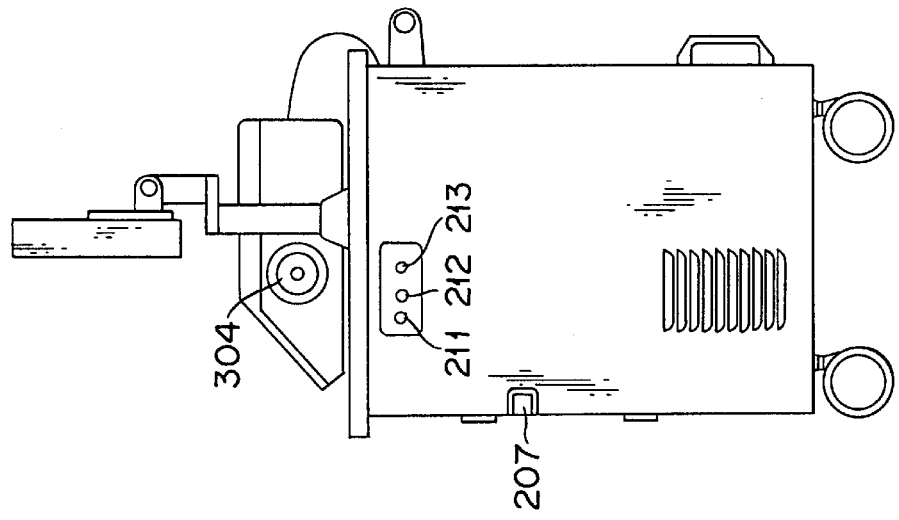
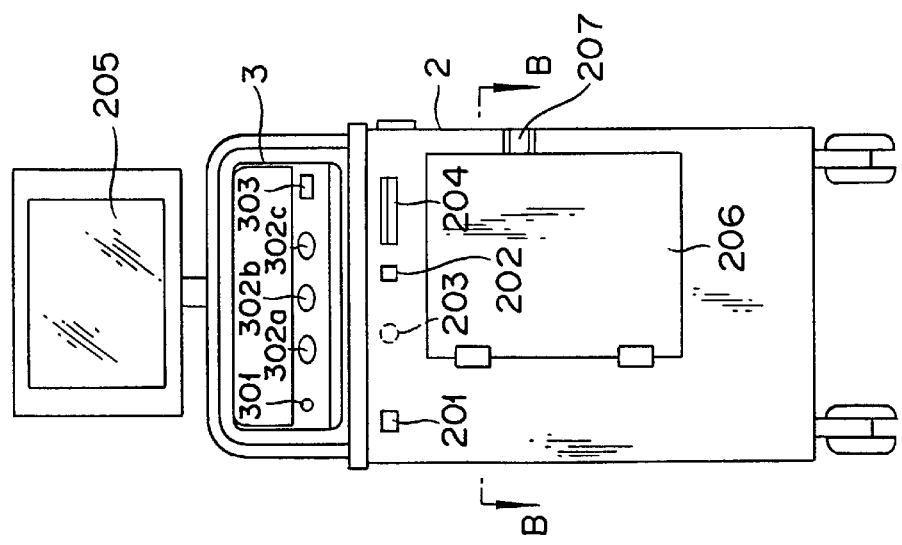

FIG. 27A

| DETECTION RESULTS OF LASER BEAM EMISSION PART'S RECIPROCATING MOTION | DETECTION RESULTS OF URETHRA SURFACE TEMPERATURE | RESULTS OF DIAGNOSIS | EXPECTED CONDITION | EXPECTED CAUSE (EXAMPLE) |
|---|---|---|---|---|
| PEAK-TO-PEAK CYCLE CONSTANT | WITHIN SET RANGE | NORMAL | APPROPRIATE | — |
| PEAK-TO-PEAK CYCLE UNSTABLE | WITHIN SET RANGE | EMISSION PART DRIVING CONDITION INAPPROPRIATE | MOTION INSTABILITY | DRIVE SYSTEM PROBLEM (MOTION PROBLEM, BACKLASH, MOTOR PROBLEM, POWER SOURCE) <br><br> MIRROR MOTION PROBLEM (BACKLASH, EXCESSIVE LOAD) <br><br> TRANSMISSION PROBLEM (EXCESSIVE LOAD TO PROBE) |
| PEAK-TO-PEAK INTERVAL SMALL | WITHIN SET RANGE | EMISSION PART DRIVING CONDITION INAPPROPRIATE | MOTION TOO FAST | DRIVE SYSTEM PROBLEM (MOTION PROBLEM, MOTOR PROBLEM, POWER SOURCE, PARTS BREAKDOWN) |
| PEAK-TO-PEAK INTERVAL LARGE | WITHIN SET RANGE | EMISSION PART DRIVING CONDITION INAPPROPRIATE | MOTION TOO SLOW | DRIVE SYSTEM PROBLEM (MOTION PROBLEM, BACKLASH, MOTOR PROBLEM, POWER SOURCE) |
| NO PEAK-TO-PEAK | WITHIN SET RANGE | EMISSION PART DRIVING OR REFLECTION CONDITION INAPPROPRIATE | MOTION STOPPED | DRIVE SYSTEM PROBLEM (MOTION PROBLEM, BACKLASH, MOTOR PROBLEM, POWER SOURCE) <br><br> MIRROR MOTION PROBLEM (BACKLASH, EXCESSIVE LOAD) <br><br> TRANSMISSION PROBLEM (EXCESSIVE LOAD TO PROBE) |

FIG. 27B

| DETECTION RESULTS OF LASER BEAM EMISSION PART'S RECIPROCATING MOTION | DETECTION RESULTS OF URETHRA SURFACE TEMPERATURE | RESULTS OF DIAGNOSIS | EXPECTED CONDITION | EXPECTED CAUSE (EXAMPLE) |
|---|---|---|---|---|
| PEAK-TO-PEAK CYCLE IS CONSTANT, BUT PEAK SIGNAL IS TOO LOW | WITHIN SET RANGE | LASER BEAM OUTPUT PROBLEM | LASER OUTPUT TOO SMALL | LIGHT SOURCE PROBLEM (OUTPUT DROP)<br><br>OPTICAL COMPONENTS PROBLEM (FIBER BENDING, GRINDING PROBLEM, BURN) |
| PEAK-TO-PEAK CYCLE IS CONSTANT, BUT PEAK SIGNAL IS TOO HIGH | WITHIN SET RANGE | LASER BEAM OUTPUT PROBLEM | LASER OUTPUT TOO LARGE | LIGHT SOURCE PROBLEM (OUTPUT INCREASE)<br><br>SETUP ERROR (OUTPUT VALUE SETUP ERROR) |
| PEAK-TO-PEAK CYCLE CONSTANT | LOWER THAN SET TEMPERATURE | LASER BEAM OUTPUT OR COOLING PROBLEM | LASER OUTPUT TOO SMALL OR EXCESSIVE COOLING | LIGHT SOURCE PROBLEM (OUTPUT DROP)<br><br>OPTICAL COMPONENTS PROBLEM (FIBER BENDING, GRINDING PROBLEM, BURN)<br><br>COOLING SYSTEM PROBLEM (EXCESSIVE COOLANT FLOW, TEMPERATURE TOO LOW) |
| PEAK-TO-PEAK CYCLE CONSTANT | HIGHER THAN SET TEMPERATURE | LASER BEAM OUTPUT OR COOLING PROBLEM | LASER OUTPUT TOO LARGE OR INSUFFICIENT COOLING | LIGHT SOURCE PROBLEM (OUTPUT INCREASE)<br><br>SETUP ERROR (OUTPUT VALUE SETUP ERROR)<br><br>COOLING SYSTEM PROBLEM (INSUFFICIENT COOLANT FLOW, TEMPERATURE TOO HIGH) |

THERMAL TREATMENT APPARATUS

BACKGROUND OF THE INVENTION

1. Field of the Invention

The invention is related to a thermal treatment apparatus for thermally treating by irradiating a vital tissue with the energy such as laser beam microwave, radio frequency, and ultrasound, by means of inserting an insertion part into a human body-either via a body cavities or lumens such as blood vessel, urethra and abdominal cavity or pressing its pressing part against a vital tissue surgically or the body surface.

2. Description of the Related Art

Various thermal treatment apparatuses have been known for treating lesions to reduce or eliminate them by means of heating, alteration, sphacelation, coagulation, cauterization or evaporation of lesions by irradiating them with the energy, such as laser beam, microwave, radio frequency, and ultrasound, with a long and slender insertion part inserted into a living body either via a body cavity or an opening produced by a small incision.

For example, the Publication of Unexamined Publication No. JP-A-11-333005 discloses a side emission type thermal treatment apparatus that irradiates a lesion located on the surface layer or its vicinity with laser beams supplied by a laser beam generator reflecting the beams with a mirror provided near the distal end of the insertion part.

In such a case, the operator himself sets up the treatment conditions of the thermal treatment apparatus by inputting each item of the treatment conditions such as the energy output power and irradiation time of the energy, e.g., laser beams.

However, in case of a thermal treatment apparatus, in which the laser beam is reflected by a mirror in order to be irradiated on the lesion, it is difficult to know the condition of the mirror, in particular, the temperature during the laser beam irradiation. The mirror temperature can rise substantially if the operator selects a large irradiation value and a long irradiation time, particularly when the cooling capacity of the refrigerant is relatively small, so that it is important for the operator to be able to measure the mirror temperature.

If the mirror is glued on to its base member with adhesive, etc., the adhesive can deteriorate because of the heat, causing the mirror to separate or peel off from the base member. The same thing can happen when the mirror and the base member are made of different materials with a big difference in the thermal expansion rates. Moreover, if the base member consists of a material with a high thermal expansion rate, the sliding resistance between the base member and the rail means that guides the mirror slidably may increase, preventing the mirror's smooth motion.

Above-mentioned publication also proposes a technology for concentrating laser beams at a target location located deep inside the vital tissue by inserting a long insertion part inside the urethra, for example, by causing its emission part equipped with a mirror, which is the laser beam reflection surface, to make a reciprocating motion inside the insertion part in longitudinal direction while changing the angle of laser beam's emission angle, i.e., the angle of the mirror. This way, only the target location is thermally treated to a desired temperature and locations excepted of the target location will be maintained at low temperatures.

However, the thermal treatment apparatus described in said publication was not able to detect the laser beam emitting motion of the continuously moving emission part. Therefore, it was difficult to confirm directly that the laser beam is being irradiated as it moves properly against the vital tissue being thermally treated.

Moreover, the thermal treatment apparatus described in said publication has a relatively complex constitution having the insertion part to be inserted into the living body and a drive unit that contains a motor for causing the laser beam emission part to make a reciprocating motion inside said insertion part. Therefore, the long insertion part is used repetitively washing and disinfecting after each use. This causes the problem of wear and tear of the apparatus. Moreover, the process of washing and disinfecting the long insertion part and the drive unit is cumbersome and time consuming. Therefore, it is desired to develop a structure that simplifies the washing and disinfecting process, or a disposal constitution.

In case of thermally treating benign prostatic hyperplasia, the transurethral method is used as the prostate is located in such a way as to surround the back of the urethra. The insertion part is inserted into the urethra, and irradiates the lesion with energies such as laser beams. In order to irradiate laser beams while checking the lesion visually, the thermal treatment apparatus disclosed in said publication is equipped with an endoscope. However, since the laser beam emission part and others are located in front of the endoscope inside the insertion part of the thermal treatment apparatus, it was difficult to secure a clear frontal view. Therefore, it used a diagonal viewing type endoscope and tried to check the location of the lesion through the side of the insertion part through the window used for emitting the laser beam. Consequently, the thermal apparatus of the prior art had a problem that it takes time to confirm the insertion location of the insertion part or the laser beam's irradiating position, as it is difficult to have a clear frontal view.

SUMMARY OF THE INVENTION

It is an object of the present invention to provide an improved thermal treatment apparatus that solves the above-mentioned problems.

It is a more specific object of the present invention to provide a thermal treatment apparatus with an improved treatment effect by means of applying energy to the intended lesion area more securely.

It is another object of the present invention to provide a thermal treatment apparatus that can be separated into a long insertion part that is used by being inserted into the living body, etc., and a drive unit that drives its laser beam irradiation part, and can securely provide a reciprocating motion of the laser beam emission part while thermal treating.

It is still another object of the present invention to provide a thermal treatment apparatus that is capable of performing frontal and side observations using an endoscope.

According to an aspect of the invention, it is a thermal treatment apparatus for thermally treating a vital tissue by means of applying energy, comprising: an energy supply unit for supplying energy for treatment; an energy output unit that is connected to said energy supply unit and has an energy reflection member for reflecting energy supplied by said energy supply unit; a drive unit that changes the position and angle of said energy reflection member; a detection unit that detects information concerning emission function of energy emitted by being reflected by said energy reflection member; and an energy control unit controlling operating conditions of said energy supply unit based on said detection unit's detection results.

The objects, features and characteristics of this invention other than those set forth above will become apparent from the description given herein below with reference to preferred embodiments illustrated in the accompanying drawings.

BRIEF DESCRIPTION OF THE DRAWINGS

FIG. 8 is a diagram showing the entire constitution of the thermal treatment apparatus;

FIG. 9A is a frontal view of the control unit of the apparatus and the laser beam generator;

FIG. 9B is a side view of the control unit of the apparatus and the laser beam generator;

FIG. 9C is a back view of the control unit of the apparatus and the laser beam generator;

FIG. 27A and FIG. 27B are diagrams showing a sample diagnostic table;

DETAILED DESCRIPTION OF THE PREFERRED EMBODIMENTS

The embodiments of this invention will be described below with reference to the accompanying drawings.

Figure 1:
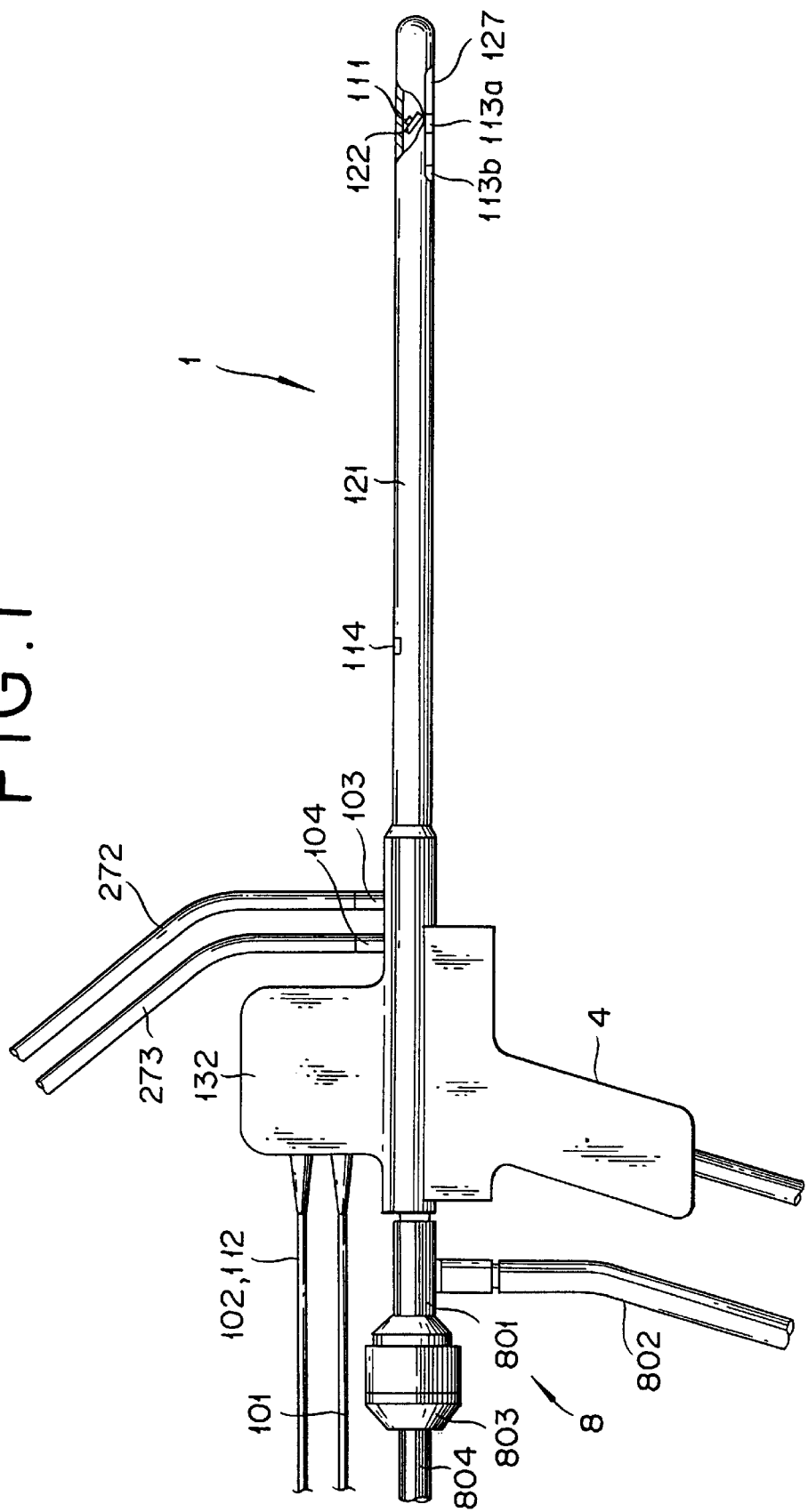
FIG. 1 is a side view of the laser beam irradiation unit used on a thermal treatment apparatus according to the first embodiment of the invention.
Figure 2:
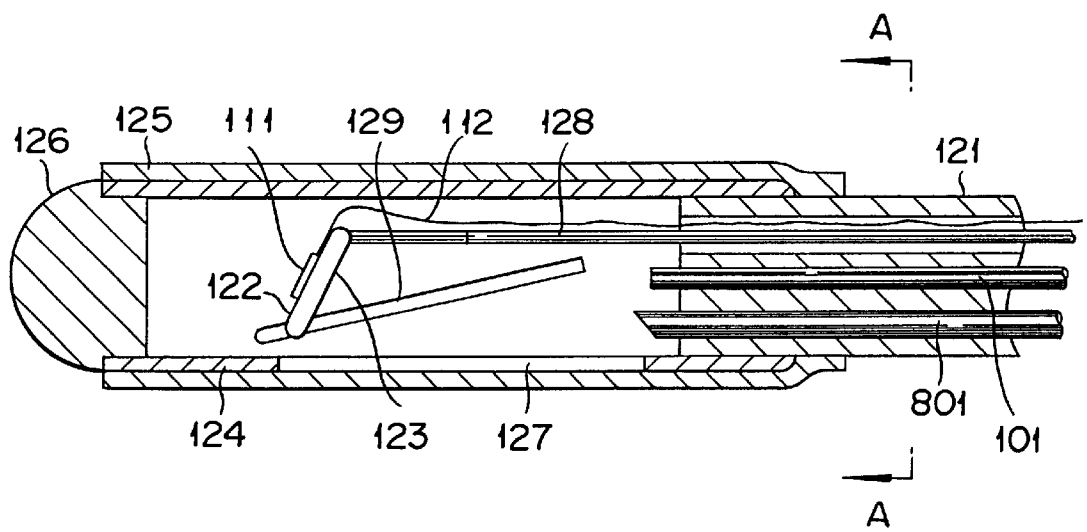
FIG. 2 is a cross section of the distal end of the laser beam irradiation unit.

FIG. 1 is a side view of the laser beam irradiation unit used on a thermal treatment apparatus according to the first embodiment of the invention, and FIG. 2 is a cross section of the distal end of the laser beam irradiation unit.

The thermal treatment apparatus of this embodiment has a side emission type laser beam irradiation unit 1 that irradiates vital tissues with laser beams. This thermal treatment apparatus inserts a long and slender insertion part 121 of the laser beam irradiation unit 1 into a living body for thermally treating a vital tissue 1001 (refer to FIG. 6) by irradiating it with laser beams emitted from a laser beam emission part 122 provided in the insertion part 121, and the apparatus is used for treatments of, for example, benign prostatic hyperplasia and various tumors such as cancers.

The laser beam irradiation unit 1, which serves as an energy generator, has a long insertion part 121, a laser beam emission part 122 that emits laser beams, and a housing 124 that contains the laser beam emission part 122 and connects with the distal end of the insertion part 121 as shown in FIG. 1 and FIG. 2.

An arm 128 is connected to the laser beam emission part 122. The arm 128 supports the laser beam emission part 122 within the housing 124. The laser beam emission part 122 is caused to move axially by moving the arm 128 in the axis direction of the insertion part 121.

The laser beam emission part 122 has a flat laser beam reflection surface (mirror) 123 for reflecting laser beams. The laser beam emission part 122 is made of a plastic, glass, metal or a composite material comprising them. The mirrors used here include specifically ones that are made of metals with the surfaces ground to mirror finish levels, mirrors made of plastic and metal base materials coated with thin films formed by vapor deposition processes, reflecting materials made of glass, etc., glued on base materials made of plastics and metals. A mirror temperature sensor 111 is provided in this embodiment for detecting the temperature of the laser beam emission part 122. The mirror temperature sensor 111 can be, but not limited to thermistor or thermocouple, a platinum temperature measuring resistor.

The mirror temperature sensor 111 is preferably installed on the back of the laser beam reflection surface 123. Such an arrangement protects the mirror temperature sensor 111 from being exposed directly to laser beams, and helps to maintain a better temperature detection accuracy and protect it from damages. It does not also reduce the reflection efficiency of laser beams. The mirror temperature sensor 111 can be installed not only to the back of the laser beam reflection surface 123, but can be installed anywhere except the laser beam reflection surface 123 of the laser beam emission part 122. The signal from the mirror temperature sensor 111 is sent to the mirror temperature sensor signal lead wire 112.

The housing 124 consists of a hard tubular member made of stainless steel having a window 127 for laser beam irradiation, and is covered by a laser beam transmitting covering member 125. In order to change the emission angle of the laser beam emitted from the laser beam emission part 122, the housing 124 has an internal wall provided with a pair of grooves 129 to engage with protrusions 131 (see FIG. 3) that are protruding on both sides of the laser beam emission unit 122. The grooves 129 that function as the guides for the laser beam emission part 122 are provided on both sides across the laser beam emission part 122 and are tilted relative to the axial direction of the insertion part 121. A cap 126 seals the distal end of the housing 124.

An optical fiber 101 for guiding the laser beam is provided inside the insertion part 121. The distal end of the optical fiber 101 can be provided with a lens. Such a lens is an optical element for minimizing the numerical aperture of the laser beam. The optical fiber 101 transmits the laser beam generated by a laser beam generator 3. A cushioning unit 132 absorbs the movement of the optical fiber by storing the optical fiber forming a loop.

The laser beam irradiation unit 1 has a drive unit 4, which is installed to be removable from the laser beam irradiation unit 1 and serves as a drive unit for the arm 128 that changes the irradiation angle of the laser beam emission part 122.

The laser beam irradiation unit 1 is equipped with an observation unit 8 used for observing the surface layers of vital tissues. This observation unit 8 has an endoscope 801 that is removable relative from the laser beam irradiation unit 1. The endoscope 801 is inserted from the proximal end to the distal end of the laser beam irradiation unit 1. The proximal end of the endoscope 801 is equipped with a camera head 803 for sending images via a camera signal lead wire 804. A light guide 802 is connected to the proximal end of the endoscope 801 to illuminate the surface layer to be irradiated with laser beams. It is also possible to make a visual observation through an eyepiece installed on the endoscope 801 without having to connect the camera head 803.

Figure 3:
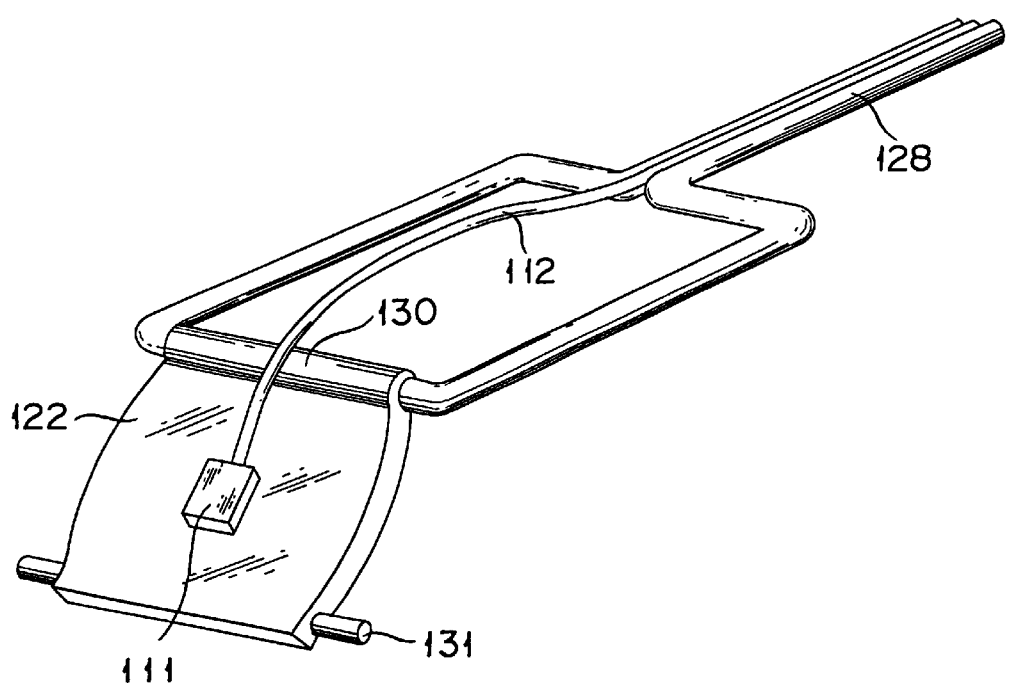
FIG. 3 is a perspective drawing for describing the structures of the laser beam emission part and the arm of the laser beam irradiation unit.

FIG. 3 is a perspective drawing for describing the structures of the laser beam emission unit and the arm of the laser beam irradiation unit.

The arm 128 supports the laser beam emission part 122 with its left and right branches inside the housing 124, so that the laser beam will reach the surface of the laser beam emission part 122 without being interrupted by the arm 128. The laser beam emission part 122 has a support part 130 on one side and a pair of protrusions 131. The support part 130 is mounted on the arm 128 pivotably to cope with the change of the irradiation angle of the laser beam emission part 122. The protrusions 131 engage with the grooves 129 provided on the internal wall of the housing 124.

The arm 128 is connected to the drive unit 4 arranged on the proximal end of the laser beam irradiation unit 1. It is also possible to have the drive unit 4 to be installed outside of the laser beam irradiation unit 1 and connect the arm 128 with the drive unit 4 via a drive shaft. The drive shaft in such a case can be a metal wire, etc.

Figure 13:
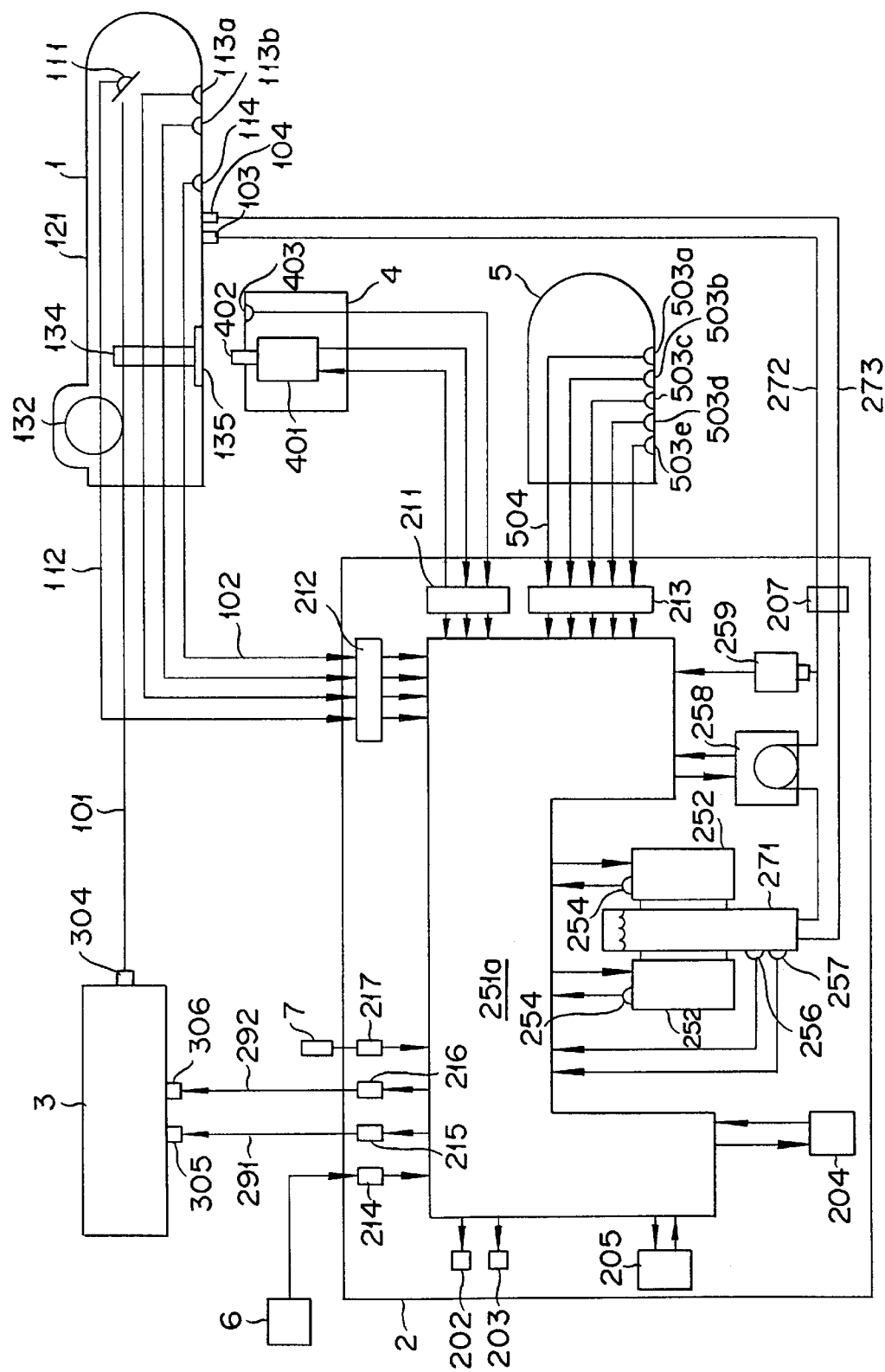
FIG. 13 is a block diagram of the control system consisting mainly of the control unit of the thermal treatment apparatus according to the first embodiment of the invention.

The drive unit 4 has a motor 401 (see FIG. 13). The It motor 401 can be an induction motor, a servomotor, a stepping motor, etc. The drive unit 4 converts the rotary motion of the motor 401 into a linear reciprocating motion by means of a cam mechanism or a link mechanism to be transmitted to the arm 128, thus causing the laser beam emission part 122 to reciprocate in the axial direction of the insertion part 121. The laser beam emission part 122 changes its tilt angle in accordance with its axial position due to the interaction between the arm 128 and the groove 129.

The drive unit 4 is constituted to be able to be removed from the laser beam irradiation unit 1 as mentioned above. More specifically, the motor 401 has a drive power transmission part 402 for transmitting drive power of the motor 401, while the arm 128 of the laser beam irradiation unit 1 is equipped with a drive power receiving part 135 via a support part 134 to which the drive power transmission part 402 can be connected removably (see FIG. 13). It is also possible to eliminate the arm 128, mount the laser beam emission part 122 pivotably on a fixed member affixed on the vicinity of the distal end of the optical fiber 101, and cause the optical fiber 101 itself to make a reciprocating motion in order to change the position and angle of the laser beam emission part 122. In this case, the support part 134 connected to the drive power receiving part 135 is connected to the optical fiber 101 that reciprocates.

By having the drive unit 4 and the laser beam irradiation unit 1 constituted removable from each other, it is possible to dispose of the laser beam irradiation unit 1, which is inserted into a human body when it used, after each usage, while using the drive unit 4 repetitively. This makes the washing and disinfecting process substantially easier, as only the drive unit 4, which has a simpler shape, is to be washed and disinfected each time.

A micro switch 403 is provided between the drive unit 4 and the laser beam irradiation unit 1 as a means of detecting that the drive unit 4 is connected to the laser beam irradiation unit 1. Therefore, the connection status between the drive unit 4 and the laser beam irradiation unit 1 can be known by signals from this micro switch 403.

The control unit 2 detects the signal from this micro switch 403 and stops the laser beam output from the laser beam generator 3, which is the laser beam supplier, in case the drive unit 4 disengages from the laser beam irradiation unit 1.

Figure 4:
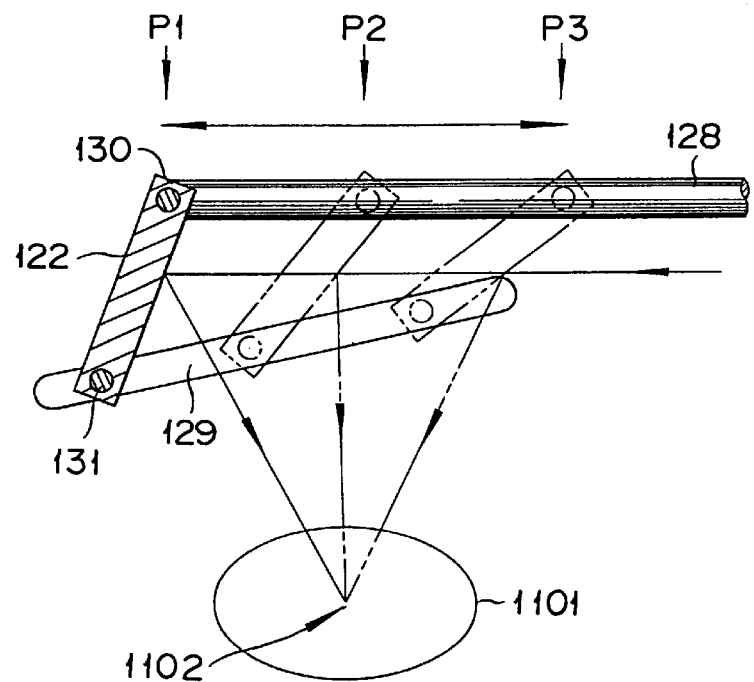
FIG. 4 is a drawing for describing the relation between the movement of the laser beam emission part and the laser beam irradiation direction.

FIG. 4 is a drawing for describing the relation between the movement of the laser beam emission part and the laser beam irradiation direction.

As can be seen from FIG. 4, the distance between the arm 128 and the groove 129, which are not parallel to each other, at the point P2 is short compared to the distance between them at the point P1. Therefore, as the support part 130 of the laser beam emission part 122 moves from the point P1 to the point P2, the protrusion 131 of the laser beam emission part 122 moves along the groove 129 and causes the tilt angle of the laser beam emission part 122 to change. In other words, the tilt angle of the laser beam emission part 122 relative to the insertion part 121 reduces in this case. Similarly, when the support part 130 of the laser beam emission part 122 moves from the point P2 to the point P3, the tilt angle of the laser beam emission part 122 relative to the insertion part 121 reduces still further. On the other hand, the laser beams reflected by the laser beam emission part 122 at the points P1 through P3 all concentrate on a target point 1102 inside the target location 1101, which is the target heating location, i.e., the lesion.

The laser beams continuously irradiate only the target point 1102, while other parts of the vital tissue such as the surface layer are irradiated only intermittently. Thus, the target point 1102 will be heated by the irradiated laser beams and reaches the desired temperature. On the other hand, other vital tissues such as the surface layer will be heated only slightly as the times they are heated are too short to generate heat.

Figure 5:
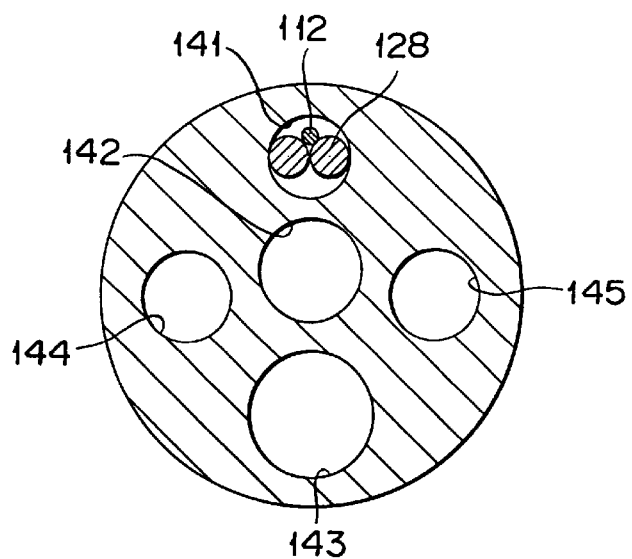
FIG. 5 is a cross section along the line A—A shown in FIG. 2.

FIG. 5 is a cross section along the line A—A shown in FIG. 2.

As shown in FIG. 5, the insertion part 121 has a working lumen 141, into which the arm 128 is inserted to slide freely. The working lumen 141 is formed in parallel with the axis of the insertion part 121. The insertion part 121 further has a lumen 142 for the optical fiber 101, a lumen 143 for the endoscope 801, a lumen 144 for introducing cooling water to be used as a cooling refrigerant, and a lumen 145 for draining the cooling water. In FIG. 5, the optical fiber 101 and the endoscope 801 are not shown. The cooling water is used to suppress the heating inside the housing 124, which otherwise will be caused because of the laser beams, and to cool the surface of the vital tissue that is contacting the housing 124.

The lumens 144 and 145 are connected to a water supply tube 272 and a water drain tube 273 via a cooling water inlet connector 103 and a cooling water outlet connector 104 respectively (see FIG. 1). By means of circulating the cooling water, the cooling efficiency improvement can be achieved. The temperature range of the cooling water is not specifically limited as long as it can reduce the damages on the laser beam emission part 122 and the irradiated surface of the vital tissue, but it should be preferably 0 to 37° C., or more preferably 8 to 25° C., which would provide a less chance of causing frostbite and provide a high cooling efficiency. In order to prevent back flows of the cooling water, it is preferable to have a check valve on each of the lumens 141 through 143. The refrigerant for cooling should preferably be disinfected fluid, for example, purified water or physiological saline.

Figure 6:
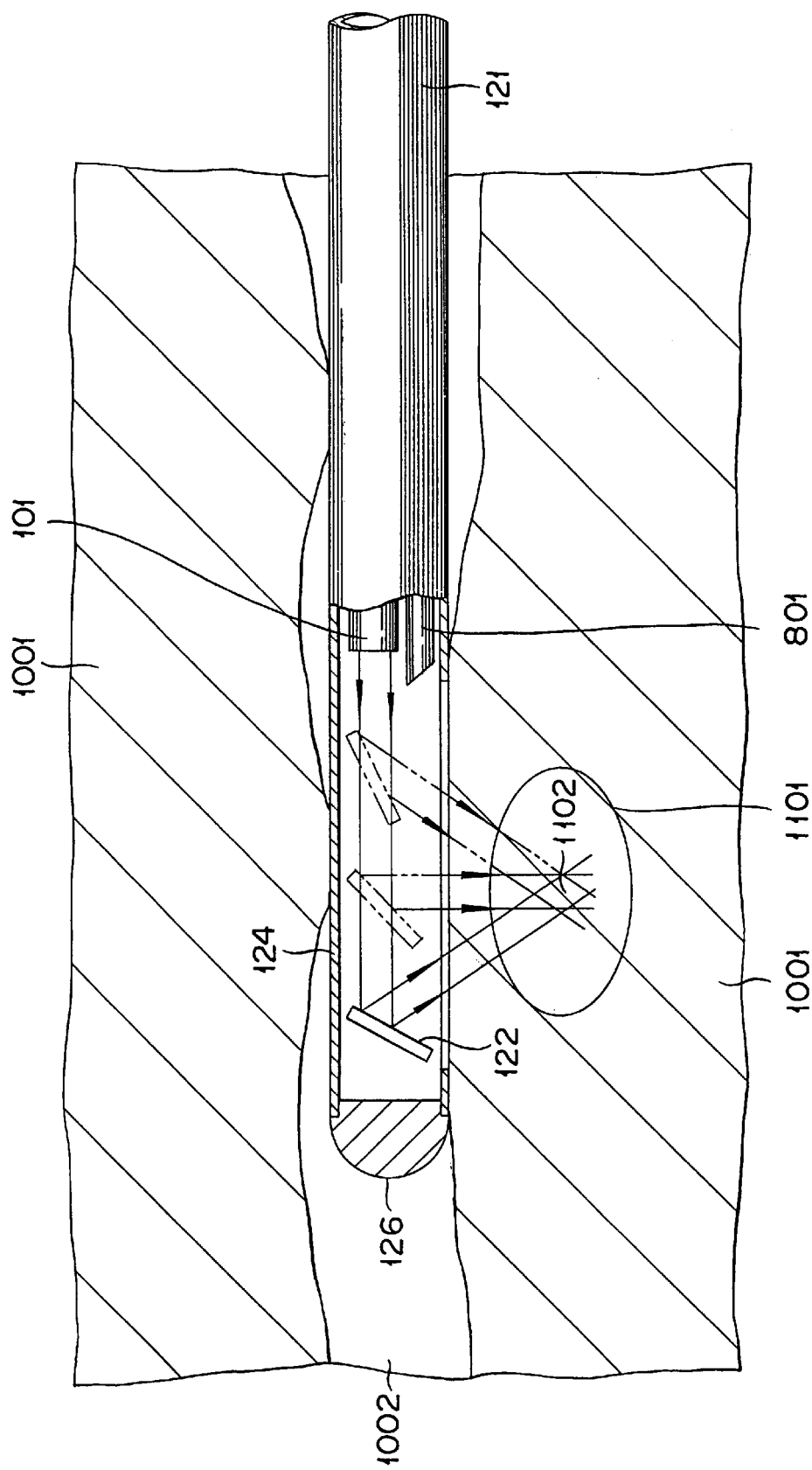
FIG. 6 is a cross section for describing an example application of the laser beam irradiation.

FIG. 6 is a cross section for describing an example application of the laser beam irradiation.

The distal end of the insertion part 121 is inserted into a body cavity 1002 and the housing 124 that contains the laser beam emission part 122 is made to contact with the surface layer in the vicinity of a target location 1101, which is the lesion, in other words, the area to be heated. In this case, it is preferable to confirm the location of the housing 124 by means of the endoscope 801. The location of a target point 1102 in the longitudinal direction of the insertion part 121 is adjusted by moving the entire laser beam irradiation unit 1 in the longitudinal direction of the insertion part 121. The position of the target point 1102 in the circumferential direction of the insertion part 121 is adjusted by rotating the entire laser beam irradiation apparatus 1.

In the irradiation of the laser beam, the laser beam emission part 122 preferably makes a reciprocating motion in the axial direction by changing the irradiation angle at the frequency of 0.1 through 10 Hz, preferably 1 through 6 Hz while changing the irradiation angle. Although the laser beam thus emitted changes the beam passage continuously, all the resultant beams cross each other at the target point 1102.

As a result, the target point 1102 and its vicinity inside vital tissues 1001 get heated by the irradiated beams and reach a desired temperature. Thus, it is possible to raise only the temperature at the desired target area 1101.

The laser beam used for irradiating the tissue 1001 can be a divergent beam, a collimated beam, or a convergent beam. In order to make a laser beam a convergent beam, an optical system is provided in the passage of the beam. Any laser beam can be used for the purpose of the invention as long as it is transmissible to living tissue. However, the wavelengths of the laser beams are preferably 750 nm through 1300 nm or 1600 nm through 1800 nm as they have particularly good transmissibility. The laser beam generator that generates laser beams with such wavelength ranges can be either gas laser beams such as the He—Ne laser beam, solid laser beams such as the Nd-YAG laser beam, or semiconductor laser beams such as the GaAlAs laser beam.

The diameter of the insertion part of the laser beam irradiation unit 1, i.e., the outer diameter of the insertion part 121 can be arbitrary as long as it can be inserted into the body cavity 1002. However, the output diameter of the insertion part 121 is preferably 2 to 20 mm, or more preferably 3 to 8 mm.

Figure 7:
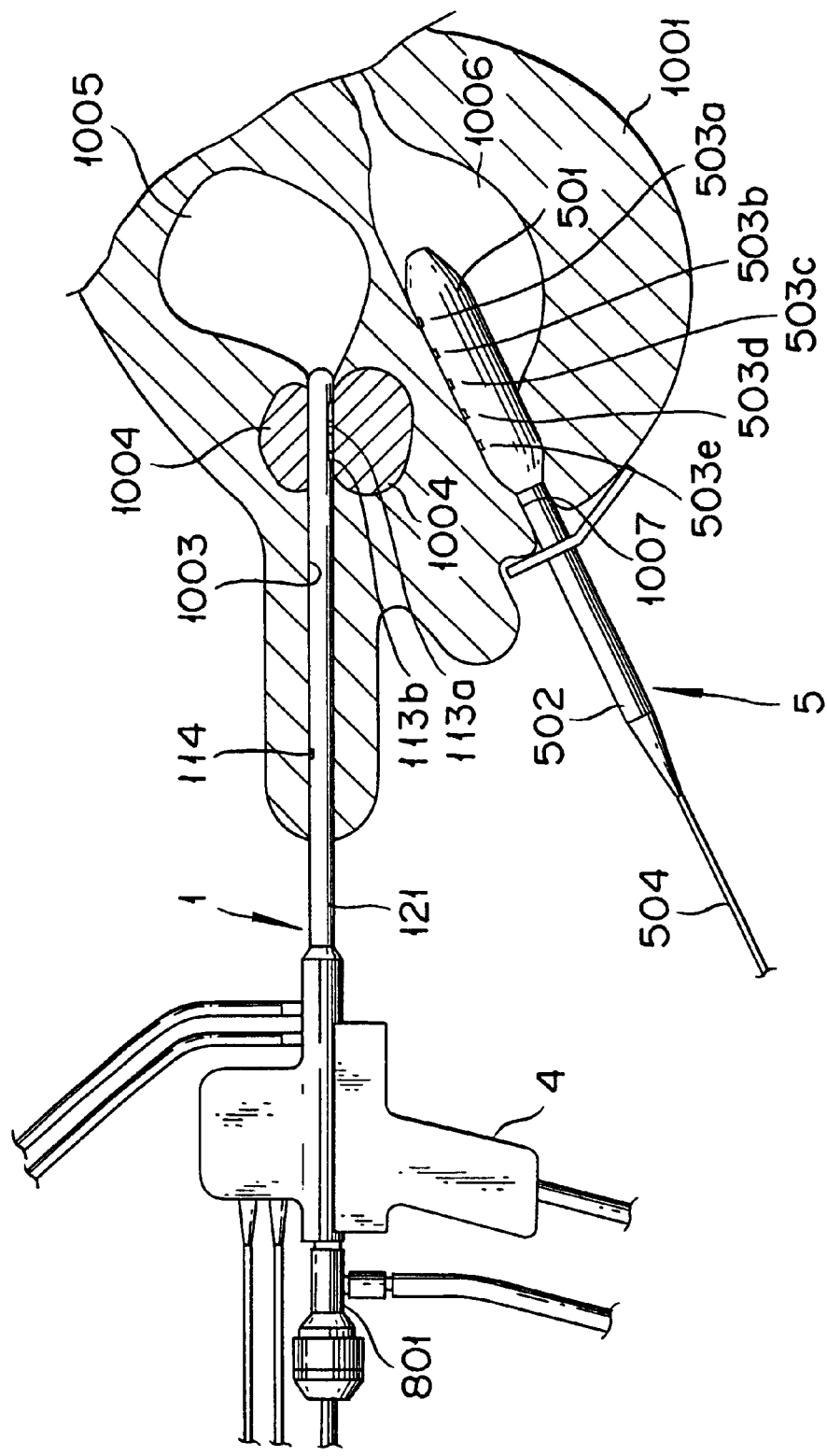
FIG. 7 is a cross section for describing an example application of the thermal treatment apparatus to a treatment of benign prostatic hyperplasia.

FIG. 7 is a cross section for describing an example application of the thermal treatment apparatus to a treatment of benign prostatic hyperplasia. The insertion part 121 of the laser beam irradiation unit 1 is inserted into the urethra 1003 and the vicinity of the distal end of the insert part 121 where the laser beam emission unit is installed is made to contact with the surface layer of the prostate 1004. The item 1005 in the drawing represents the bladder. Urethra temperature sensors 113a and 113b are provided to detect the temperatures of the urethra wall inside the insertion part 121 in the vicinity of its distal end.

The thermal treatment apparatus of this embodiment has a rectum probe 5. The rectum probe 5 has an insertion part 501, which is inserted into the rectum 1006 through the anus 1007, and a grip 502, which is held by the operator. The insertion part 501 of the rectum probe 5 is provided with multiple rectum temperature sensors 503*a* through 503*e* for detecting the temperatures of the rectum wall, and the detected values are transmitted through sensor signal lead wire 504. The rectum temperature sensors 503*a* through 503*e* are not implanted in vital tissues but rather placed deep inside the rectum as illustrated.

Therefore, this thermal treatment apparatus is capable of conducting a thermal treatment using the results of urethra wall temperature and rectum wall temperature detections. This way it is possible to prevent the normal tissues of the urethra and the rectum existing in the vicinity of the prostate being unnecessarily heated. The temperature sensors that can be used as the urethra temperature sensors 113*a* and 113*b* are thermistors, thermocouples, and platinum temperature measuring resistors, but the thermocouple is the most preferable because the thermocouple is smaller so that its effect on laser beam irradiation is minimum and the thermistor is inexpensive. As to the temperature sensors that can be used as the rectum temperature sensors 503*a* through 503*e* are also thermistors, thermocouples, and platinum temperature measuring resistors, but the thermistor is the most preferable because it is inexpensive.

Figure 10:
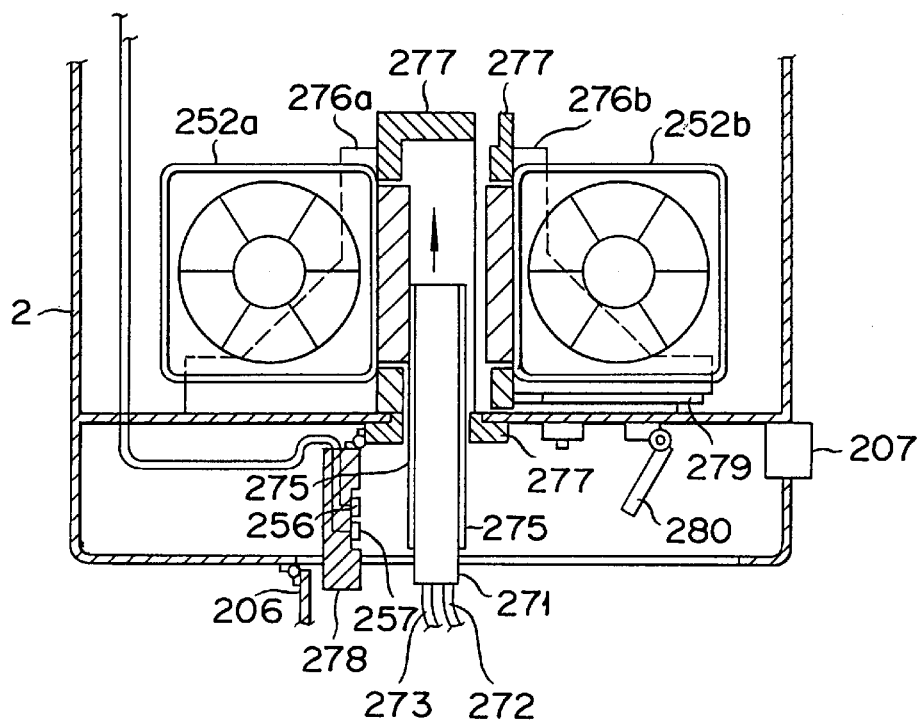
FIG. 10 is a cross section along the line B—B shown in FIG. 9.
Figure 11:
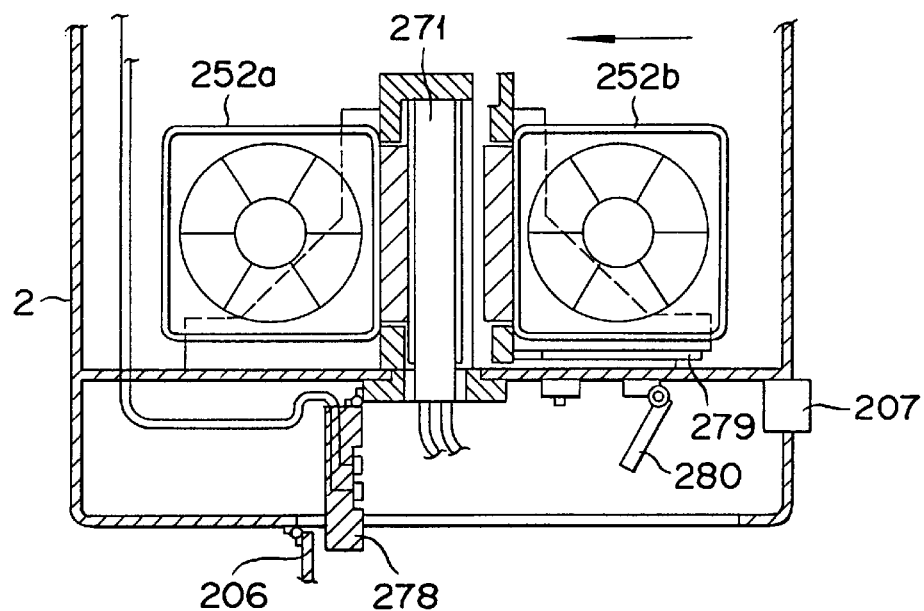
FIG. 11 is another cross section along the line B—B shown in FIG. 9.
Figure 12:
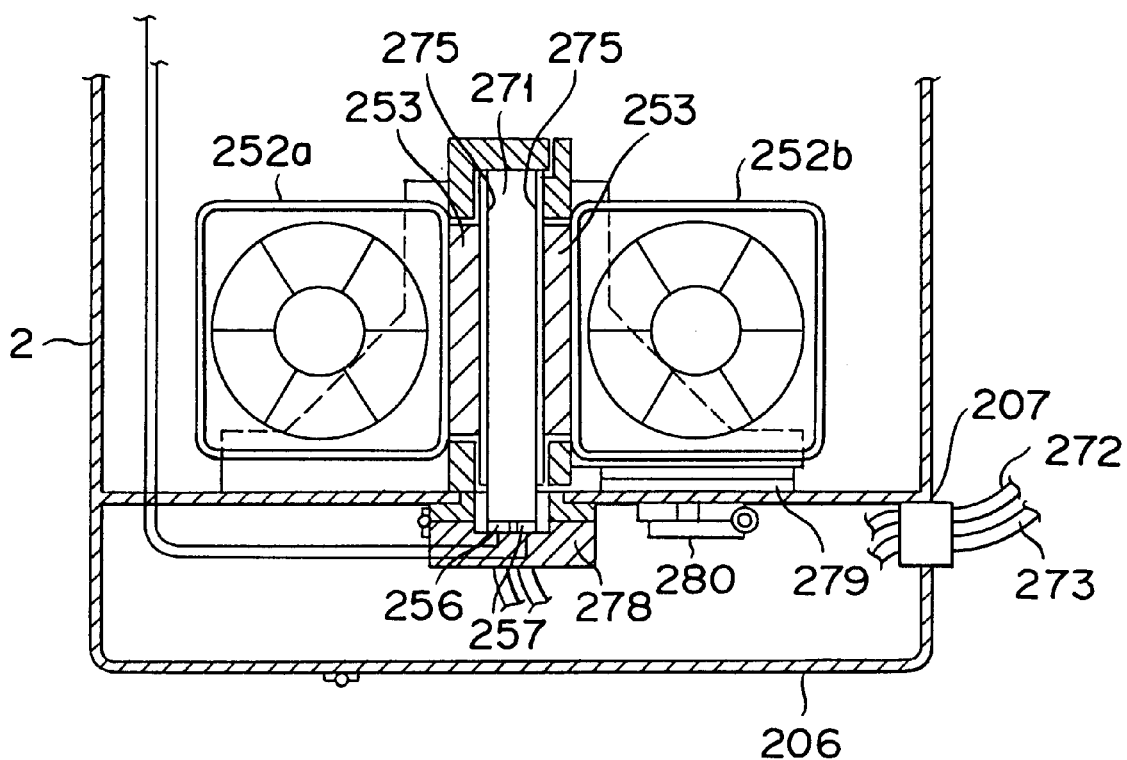
FIG. 12 is another cross section along the line B—B shown in FIG. 9.

FIG. 8 is a diagram showing the entire constitution of the thermal treatment apparatus, FIG. 9A is a frontal view of the control unit of the apparatus and the laser beam generator, FIG. 9B is a side view of the control unit of the apparatus and the laser beam generator, FIG. 9C is a back view of the control unit of the apparatus and the laser beam generator, and FIG. 10 through FIG. 12 are cross sections along the line B—B shown in FIG. 9.

The thermal treatment apparatus of this embodiment includes, as shown in FIG. 8, a laser beam irradiation unit 1, a control unit 2, a laser beam generator 3, a drive unit 4, a rectum probe 5, a footswitch 6, and an observation unit 8. The laser beam irradiation unit 1, the laser beam generator 3, the drive unit 4, the rectum probe 5, and the footswitch 6 are connected to the control unit 2. The footswitch 6 sends a signal to a control unit 2 prompting laser beam irradiation when the operator steps on it.

The observation unit 8 is equipped with a light source unit 805 that supplies illumination light for endoscope observation, a TV camera unit 806 for capturing images observed by an endoscope, an image receiver 807 for displaying images captured by the television camera unit 806, and a movable cart 808 carrying all of these units. A light source unit 805 is connected to a light guide 802. A TV camera 806 is connected to a camera head 803 via a camera signal lead 804. Thus, it is possible to perform thermal treatments as observing through an endoscope 801.

The control unit 2 controls the entire operation of the thermal treatment apparatus using the detection signals from various sensors and micro switches built into the laser beam irradiation unit 1, the drive unit 4, and the rectum probe 5.

As shown in FIG. 9, the front face of the control unit 2 is provided with a main switch 201 for turning on the power, an abnormality warning lamp 202 for warning the operator by light in case of predetermined abnormalities, an abnormality warning buzzer 203 for warning the operator by sound in case of predetermined abnormalities, and a media interface 204 for inputting the information of external memory media. In the embodiment, the media interface 204 includes drive units for flexible disks (FD), optical magnetic disks (MO) and the like recorded information such as images got by diagnosing a patient. A user interface 205 is provided on top of the control unit 2 for displaying predetermined types of information to the user and for receiving predetermined setups and operations. The user interface 205 of this embodiment is a touch type operating panel that includes a display screen.

On the side of the control unit 2 are a drive unit connector 211 for connecting with the signal lead wires extending from the drive unit 4, a urethra sensor connector 212 for connecting with the sensor signal lead wires 102 and 112 extending from the sensors provided at the laser beam irradiation unit 1, and a rectum connector sensor 213 for connecting with the sensor signal lead wires 504 extending from the sensors provided at the rectum probe 5.

On the back of the control unit 2 are a footswitch signal input connector 214 for connecting with the signal lead wires from the footswitch 6 and a foot switch signal output connector 215 for connecting with the footswitch signal lead cable 291. The footswitch signal lead cable 291 is for transmitting the footswitch signal from the footswitch 6 via the control unit 2. Moreover, on the back of the control unit 2 are an interlock switch signal input connector 217 for connecting with the signal lead wires extending from the interlock switch 7 (see FIG. 13) and an interlock switch signal output connector 216 for connecting with the interlock switch signal cable 292. The interlock switch signal cable 292 is for transmitting the interlock switch signal from the interlock switch 7 via the control unit 2. The item 218 shown in the drawing is an inlet for connecting with the power supply cable (not shown).

On the front of the laser beam generator 3 are a main switch 301 for turning on the power, setup dials 302*a* through 302*c* for the operator to set up the output conditions of the laser beam, and an emergency stop switch 303 for stopping the laser beam in an emergency. The setup dials 302*a* through 302*c* are used to set up the output conditions such as laser beam output power, laser beam pulse time, laser beam pulse interval and laser beam output time, etc. The recommended laser beam output conditions planned by the control unit 2 are displayed on the user interface 205. The operator can arbitrarily set up the laser beam output conditions using the recommended values as references.

On the side of the laser beam generator 3 is a laser beam output connector 304 for connecting with the proximal end of the optical fiber 101. On the back of the laser beam generator 3 a footswitch signal input connector 305 and an interlock switch signal input connector 306 for connecting the above-mentioned footswitch signal cable 291 and the interlock switch signal cable 292 respectively. The item 307 shown in the drawing is an inlet for connecting with the power supply cable (not shown).

As shown in FIG. 9, the laser beam generator 3 and the control unit 2 are both standalone units having their own cabinets with different frames. The laser beam generator 3 to be combined with the control unit 2 is not only limited to a dedicated unit, but rather a different laser beam generator can be used in combination with the control unit 2 as long as the specifications of the foot switch signal and the interlock switch signal are matching ranges. For example, it is possible to have several laser beam generators of different rated output value of laser beam to use as changing them properly. This improves the system performance of the entire thermal treatment apparatus and also the maintenance performance as the laser beam generator can be easily disconnected.

A cooling unit is provided inside the control unit 2 as shown in FIG. 9 and FIG. 10 through FIG. 12, and a cooling unit door 206 is provided on the front of the control unit 2. The cooling unit has a bag 271 for holding the cooling water. The bag 271 is connected with the water supply tube 272 and the water drain tube 273. These water supply tube 272 and water drain tube 273 are connected with the cooling water input connector 103 and the water drain connector 104 of the laser beam irradiation unit 1 via a tube panel 207. The bag 271 has two sides parallel to each other and a bag sidewall 275 is glued on each side surface 275. The bag 271 is made of a silicone rubber plate or sheet and the bag sidewall 275 is made of a material with a good thermal conductivity such as an aluminum plate or sheet.

The cooling unit has a first cooling element 252a that contacts with one side of the bag 271 via the bag sidewall 275 and a cooling face 253, and a second cooling element 252b that contacts with or separates from another side of the bag 271 via the bag sidewall 275 and the cooling face 253. The cooling elements 252a and 252b, for example, can be those that use Peltier elements. The first cooling element 252a is mounted on a fixed frame 276a and the second cooling element 252b is movable with a frame 276b along a slide rail 279.

When the cooling unit is used, the bag 271 on which the bag sidewall 275 is glued on, is stored in a thermally insulated housing 277 that is thermally insulated (FIG. 10). Next, the second cooling element 252b is moved toward the first cooling element 252a (FIG. 11), and is affixed with the hinge type affixing member 280 (FIG. 12). Thus, the bag 271 is positioned by being sandwiched by the first and second cooling elements. By closing the insulating door 278 that has an insulating characteristic, the insulating housing 277 that stores the bag 271 will be sealed. The insulating door 278 is provided with a water temperature sensor 256 that detects the cooling water temperature and a water level sensor 257 that detects the water level and their detection results are transmittable.

Figure 14:
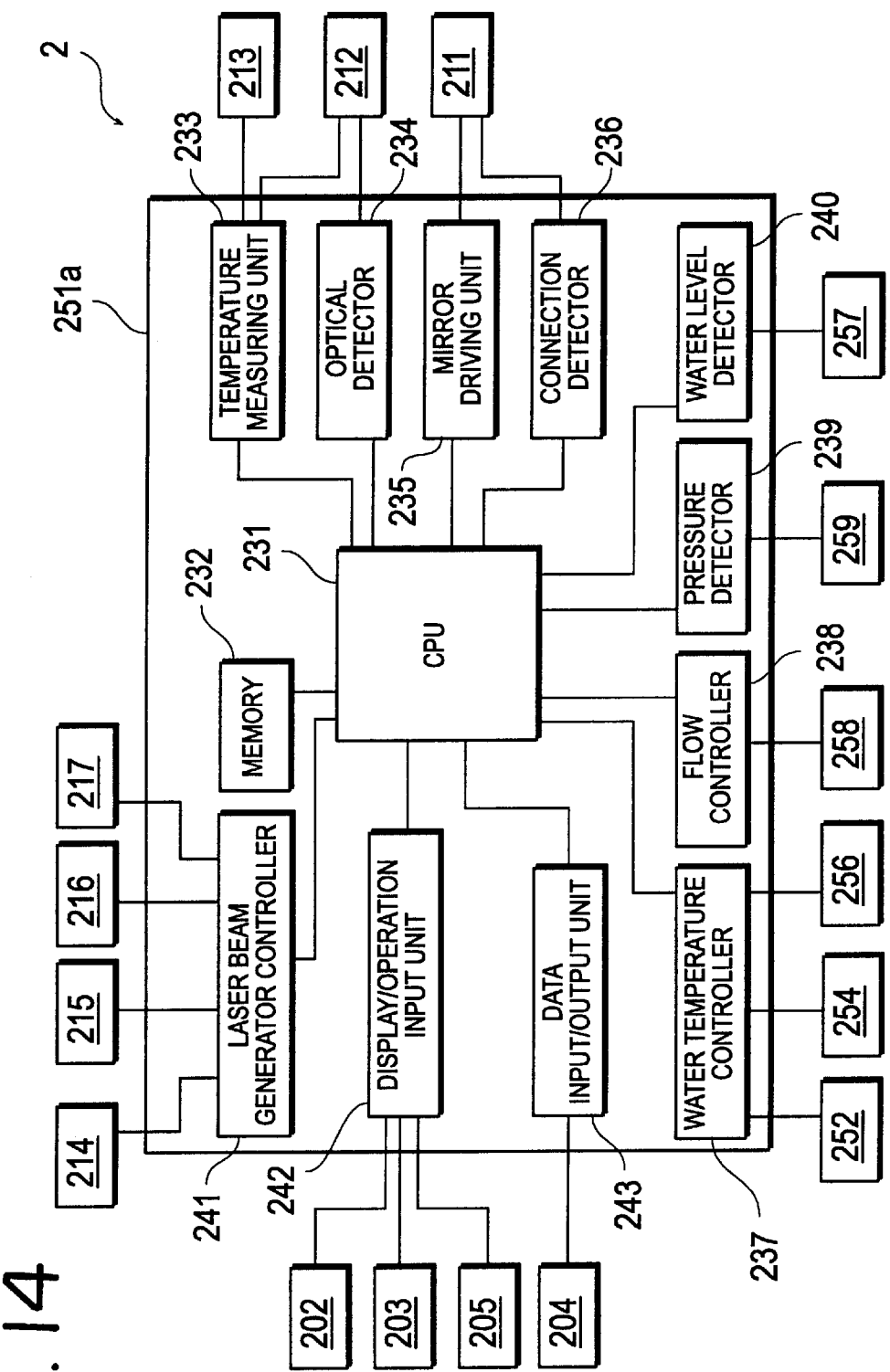
FIG. 14 is a diagram for describing the details of the control unit shown in FIG. 13.

FIG. 13 is a block diagram of the control system consisting mainly of the control unit of the thermal treatment apparatus according to the first embodiment of the invention and FIG. 14 is a diagram for describing the details of the control unit shown in FIG. 13. Those that have already been described will not be repeated in the following descriptions.

The control unit 2 has a controller 251a as shown in FIG. 13. As shown in FIG. 14, the controller 251a is equipped with peripheral controllers such as a temperature measurement unit 233, an optical detector 234, a mirror driving unit 235, a connection detector 236, a water temperature controller 237, a flow controller 238, a pressure detector 239, a water level detector 240, a laser beam generator controller 241, a display/operation input unit 242, and a data input/output unit 243, a CPU 231 for controlling such peripheral controllers integrally, and a memory 232 for storing specified programs and data.

The temperature measuring unit 233 receives detection signals from a mirror temperature sensor 111 and urethra temperature sensors 113a and 113b via a urethra sensor connector 212, as well as detection signals from rectum temperature sensors 503a through 503e via a rectum sensor connector 213. The optical detector 234 receives a detection signal from a light sensor 114 via a urethra sensor connector 212. The light sensor 114 is installed in the laser beam irradiation unit 1 and detects optically whether the insertion part 121 of the laser beam irradiation unit 1 is not abutting the object of irradiation by the laser beam. This makes it possible, for example, to prevent the laser beam to be emitted under the condition that the insertion part 121 is not inserted in the human body.

The mirror driving unit 235 is connected to a motor 401 of the drive unit 4 via a connector 211 and exchanges signals. The drive signal is sent by the mirror drive unit to the motor 401. The motor 401 has a detection means (not shown) for detecting rotating speeds, rotating angular positions, and rotating loads and the signals from these detection means are fed back to the mirror drive unit.

The connection detector 236 receives detection signals from a micro switch 403 that detects whether the drive unit 4 is connected to the laser beam irradiation unit 1 via the drive unit connector 211. When the CPU 231 detects that the drive unit 4 is disconnected from the laser beam irradiation unit 1 from the signal from the micro switch 403, it sends an instruction to the laser beam generator controller 241 to stop the laser beam output. Thus it is possible to cause the laser beam emission part 122 to make a reciprocating motion securely and irradiate the lesion with the laser beam. The CPU 231 simultaneously displays on the user interface 205 via display/operating input unit 242 that the drive unit 4 is disconnected from the laser beam irradiation unit 1 and the laser beam output is stopped.

The water temperature controller 237 receives detection signals from a water temperature sensor 256, and the water temperature controller 237 issues a signal for cooling to the cooling element 252. Thus, the water of the circulated cooling water can be controlled within a preferred range suitable for treatment. Moreover, the water temperature controller 237 can stop the power supply to the cooling element, if a excessively high temperature of the cooling element 252 is detected by a thermostat 254. The water level detector 240 receives detection signals from a water level sensor 257 so that it is possible to judge if the necessary amount of the cooling water is maintained.

The flow controller 238 is connected to a pump 258 to exchange signals. The flow controller 238 issues drive signals to the pump 258, and the pump 258 feeds back detection signals concerning the flow amount rate and others to the flow controller 238. This makes it possible to control the cooling water flow amount rate. Roller pumps, diaphragm pumps, magnet pumps, etc., can be uses as the pump 258. The pressure detector 239 receives detection signals from a pressure sensor 259 that detects the water pressure in the water supply tube 272. Monitoring the detection results of the pressure sensor 259 makes it possible to avoid the cooling water from reaching excessively high pressures.

The laser beam generator controller 241 receives signals from the footswitch 6 via a footswitch signal input connector 214. The laser beam generator controller 241 issues signals for outputting laser beams to the laser beam generator 3 via a footswitch signal cable 291. When it receives signals from an interlock switch 7 via an interlock switch signal input connector 217, the laser beam generator controller 241 issues signals for stopping the output of laser beams to the laser beam generator 3 via an interlock switch signal cable 292. The interlock switch 7 issues signals to stop the operation of the laser beam generator 3 interlocking with, for example, the signal that the door of the laser beam management area is opened.

The display/operation input unit 242 lights an abnormality warning lamp 202 and outputs a signal for operation to an abnormality warning buzzer 203. The display/operation input unit 242 is connected to a touch panel (touch screen) display 205 that receives various input for operations and instructions for exchanging signals. A certain type of information is outputted from the display/operation input unit 242 to the user interface 205, and signals corresponding to various settings and instructions by the operator are issued from the user interface 205 to display/operation input unit 242.

The data input/output unit 243 is connected to media interface 204 in order to make it possible to read or write various information concerning patients such as diagnostic information and thermal treatment histories via external memory media. It is also possible to enter diagnostic information directly from various image diagnostic devices to external memory devices by directly connecting with them.

In using the thermal treatment apparatus constituted as shown above, the lesion of the patient is diagnosed first of all. The diagnosis of the lesion can be made using optical endoscopes, ultrasonic endoscopes, X-ray contrast radiography, magnetic resonance imaging (MRI), computed tomography (CT) using X-ray or magnetic resonance, positron emission tomography (PET), single photon emission computed tomography (SPECT), etc.

The image information of the lesion periphery obtained by diagnosing the patient in advance will be entered from the media interface 204 through floppy disks, etc. the inputted image information of the lesion periphery will be displayed on the user interface 205. The operator will decide the target location, which is the target thermal location from the displayed lesion, and input the information concerning the target location through the user interface 205.

The control unit 2 plans the treatment condition based on the target location determined by the operator and displays the recommended values of the treatment condition on the user interface 205. The operator will setup the output condition of the laser beam as a treatment condition referencing the recommended values by means of the setup dial 302a through 302c of the laser beam generator 3.

The laser beam output conditions as the treatment conditions are, for example, laser beam output power, laser beam output time, etc. Although general values in thermal treatment are used as the treatment conditions such as the cooling water temperature, cooling water flow amount, travel speed of the laser beam emission part, etc., they can be set up as needed through the user interface 205.

When the operator completes the treatment condition and steps on the footswitch 6, the footswitch signal is inputted into the control unit 251a of the control unit 2. In this embodiment, stepping on the footswitch 6 alone does not cause the laser beam generator 3 to operate. The control unit 251a grasps the statuses of various parts of the thermal treatment apparatus, and issues a signal via the foot switch signal cable 291 to the laser beam generator 3 allowing it to output the laser beam when the condition is suitable for outputting the laser beam.

More specifically, when the detection signal of the mirror temperature sensor 111 provided at the laser beam irradiation unit 1 exceeds the set value, the control unit 251a stops issuing the signal for outputting the laser beam being transmitted via the foot switch signal cable 291, and stops the operation of the laser beam generator 3.

Thus, it is possible to stop the operation of the apparatus with an ample time before the following problems occur even if the operator has selected a substantially large laser beam output value as well as a substantially large irradiation time and the cooling capacity of the refrigerant is relatively small so that the mirror temperature rise occurs. Consequently, it is possible to prevent excessive wear of the apparatus, in particular, the surroundings of the mirror. Expected problems include the mirror's lifting up or peeling off from the mirror base as a result of deterioration of the adhesive due to heat if the mirror is attached to its base by means of adhesion. This can happen also in case the mirror and the base have widely different thermal expansion coefficients. Moreover, if the base is made of a material with a high thermal expansion coefficient, the sliding friction between it and the rail means (groove 129) that guides the mirror increases and prevents smooth sliding of the mirror.

The controller 251a stops the operation of the laser beam generator 3 when it judges that there is a deviation beyond the specified tolerance for the instructed values or the stoppage of the motor 401 based on the detection signals of the rotating speed, rotating angle and rotating load fed back from the motor 401 of the drive unit 4.

The controller 251a further stops the operation of the laser beam generator 3 when it judges that the drive unit 4 is not securely connected to the laser beam irradiation unit 1 based on the detection signal of the micro switch 403 of the drive unit 4. Therefore, the risk of continuously irradiating with the laser beam in one direction is avoided by stopping the laser beam emission, if in case the drive unit 4 disengages from the laser beam irradiation 1 during a treatment.

Moreover, if an abnormal status occurs such that the laser beam control area's door is opened by mistake during a thermal treatment, the interlock switch 7 is activated and the controller 251a stops the operation of the laser beam generator 3. The controller 251a further monitors the signals from various sensors, micro switches, thermostats, etc., and the operating conditions of various parts, and controls the operations of various parts such as laser beam generator 3 of the thermal treatment apparatus as needed.

Thus, according to this embodiment, it is possible to achieve a good treatment result by securely applying the laser beam to the targeted lesion location while reciprocating the laser beam emission part 122 at a specified frequency as the information concerning the laser beam's emission functions are detected and the operating conditions of the laser beam generator 3 are controlled based on said detection results.

Figure 15:
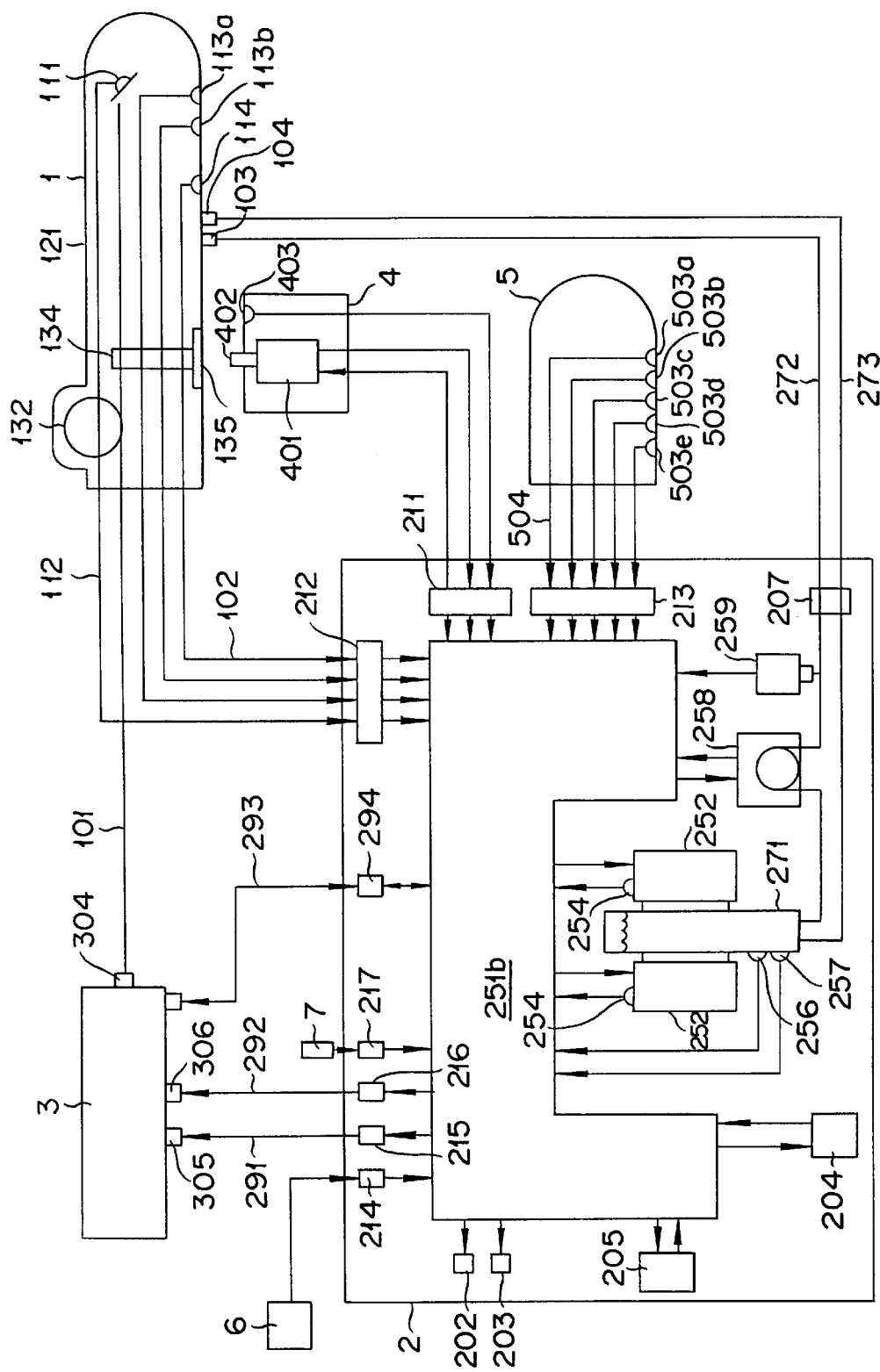
FIG. 15 is a block diagram of the control system consisting mainly of the control unit of the thermal treatment apparatus according to the second embodiment of the invention.
Figure 16:
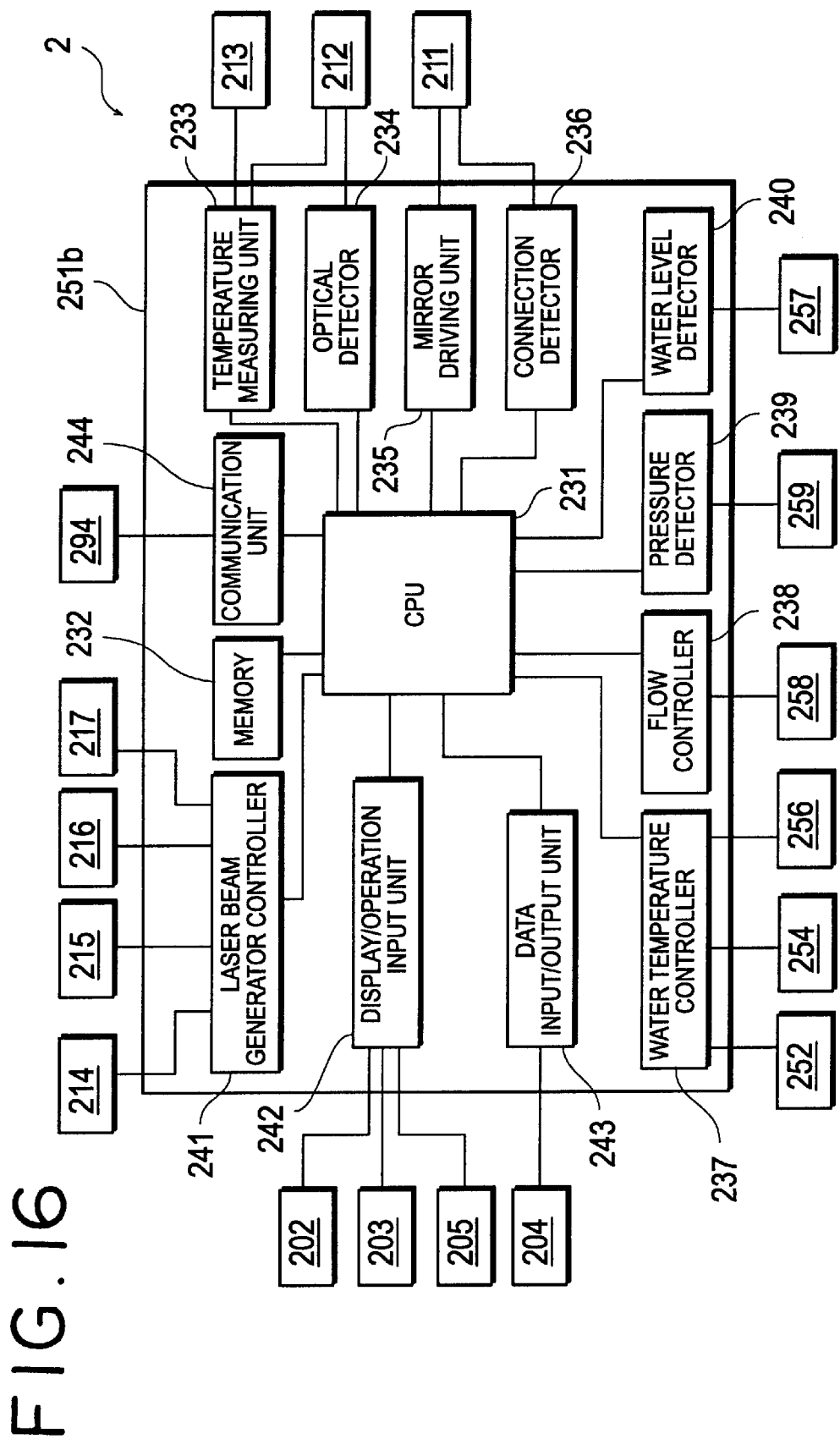
FIG. 16 is a diagram for describing the details of the control unit shown in FIG. 15.

FIG. 15 is a block diagram of the control system consisting mainly of the control unit of the thermal treatment apparatus according to the second embodiment of the invention and FIG. 16 is a diagram for describing the details of the control unit shown in FIG. 15. The second embodiment will be described bellow primarily concerning with the differences from the first embodiment.

As shown in FIG. 15 and FIG. 16, the controller 251b of the control unit 2 in this second embodiment has a communication unit 244, the communication unit 244 being connected with the laser beam generator 3 via a communication connector 294 and a communication cable 293. Although, in the first embodiment, the operator finally sets up the output conditions of the laser beam as the treatment conditions by means of the setup dials 302a through 302c of the laser beam generator 3, the laser beam output conditions are automatically set up in the second embodiment by means of transmitting the conditions planned by the controller 251b via the communication cable 293 to the laser beam generator 3.

Figure 17:
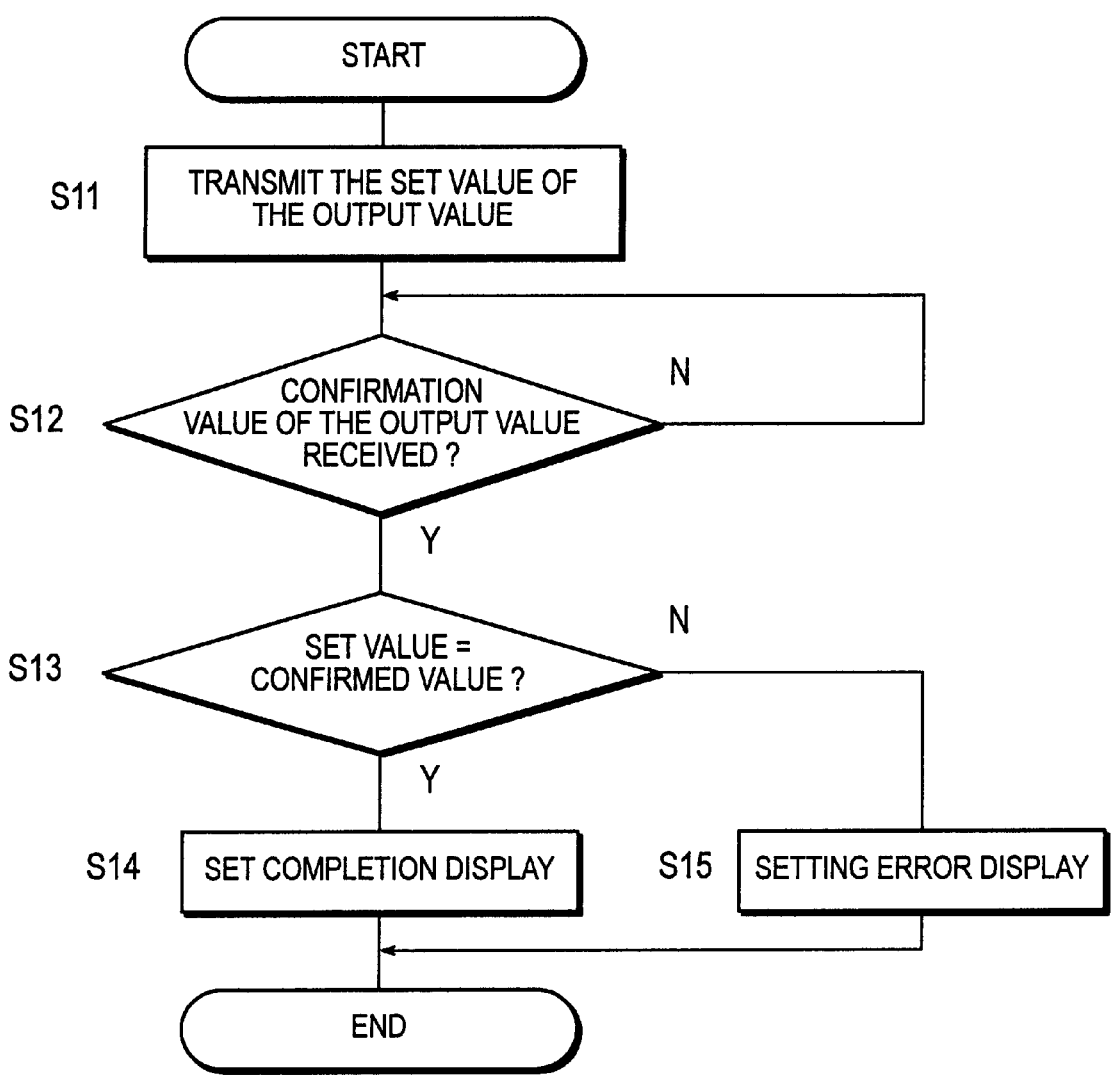
FIG. 17 is a flowchart for describing the setup operation of the laser beam output power.
Figure 18:
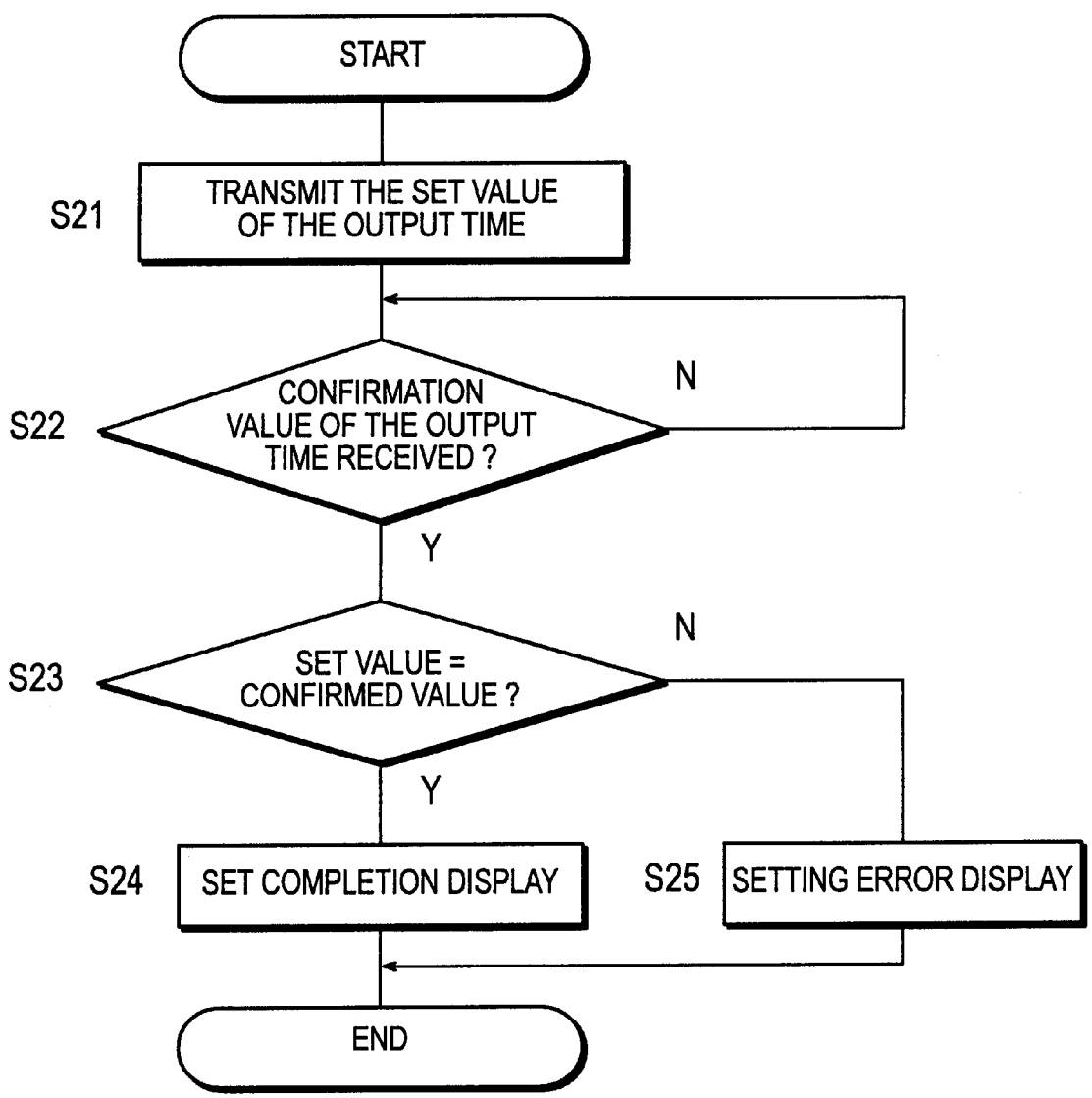
FIG. 18 is a flowchart for describing the setup operation of the laser beam output time.
Figure 19:
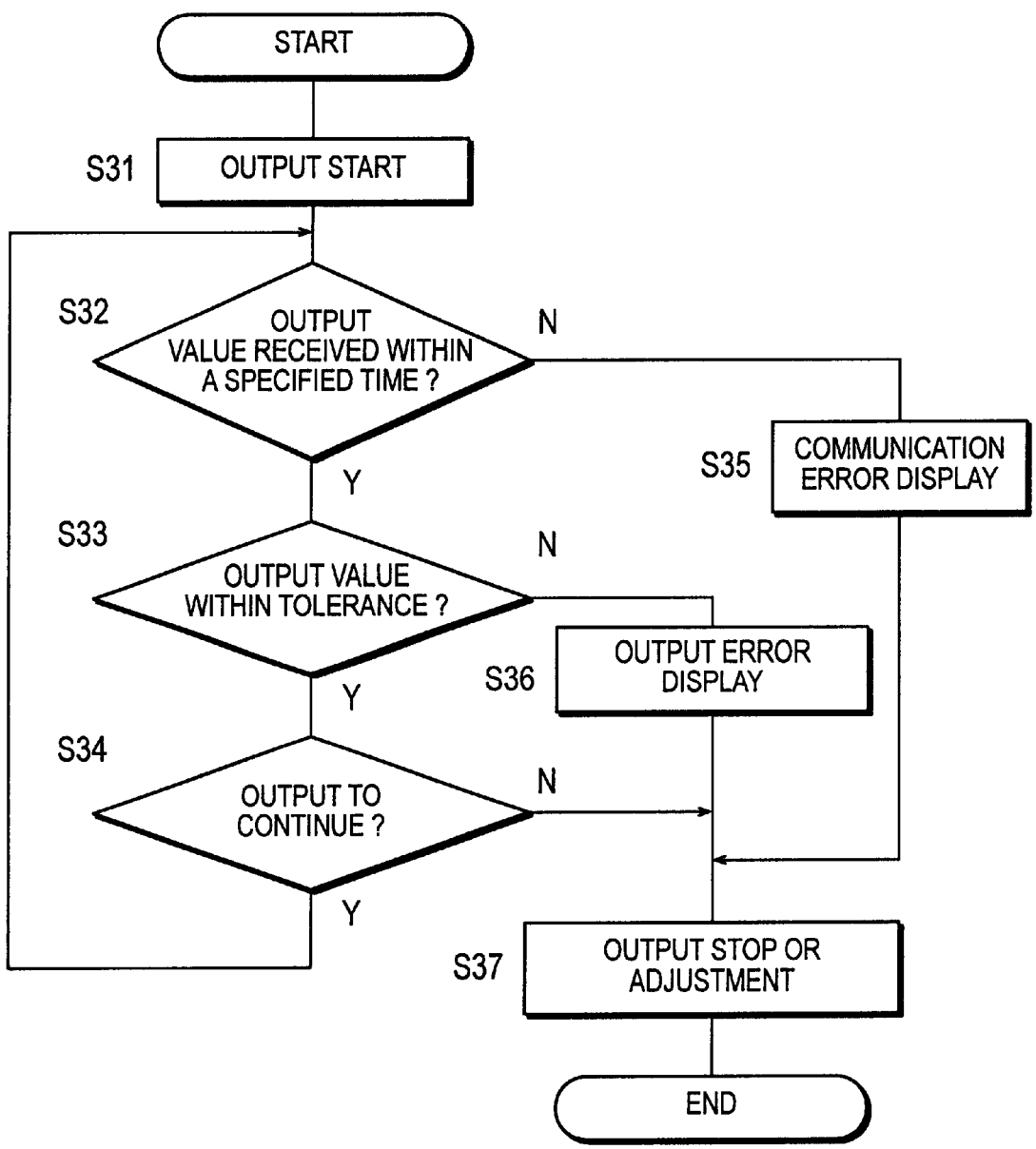
FIG. 19 is a flowchart for describing the monitoring operation of the laser beam output conditions.

FIG. 17 is a flowchart for describing the setup operation of the laser beam output power, FIG. 18 is a flowchart for describing the setup operation of the laser beam output time, and FIG. 19 is a flowchart for describing the monitoring operation of the laser beam output conditions.

As shown in FIG. 17, the controller 251b of the control unit 2 plans the treatment condition based on the target location determined based on diagnostic information, etc., and transmits the laser beam output power (e.g., 30 W) set up as a treatment condition to the laser beam generator 3 via the communication cable 293 (S11). The laser beam generator 3 confirms the setup value of the laser beam output power transmitted by the controller 251*b* and returns it as the confirmed value of the laser beam output power via the communication cable 293. When it receives the confirmed value of the laser beam output power returned by the laser beam generator 3 (S12: Yes), the controller 251*b* makes a judgment whether the setup value of the laser beam output power matches with the confirmed value (S13).

If the setup value of the laser beam output power matches with the confirmed value (S13: Yes), the controller 251*b* displays on the user interface 205 that the setup of the laser beam output power has been completed (S14), and terminates the setup operation of the laser beam output power. Thus, the laser beam output power is automatically and securely set up using the communication cable 293. If, on the other hand, the setup value of the laser beam output power does not match with the confirmed value (S13: No), the controller displays on the user interface 205 that there was an error in the setup of the laser beam output power (S15), and prompts the operator to handle it according to the predetermined procedure.

Although the controller 251*b* conducts the setup operation for the laser beam output time as a treatment condition (S21 through S25) as shown in FIG. 18, the description of the procedure will not be repeated here, as it is similar to the setup operation for the laser beam output condition (S11 through S15). The laser beam output time is set up to be approximately 300 seconds.

Moreover, when the operator steps on the footswitch 6 assuming that the initial setup is completed as shown in FIG. 19, the controller 251*b* checks the conditions of various parts of the thermal treatment apparatus and sends a signal to the laser beam generator 3 to output laser beams if the conditions for outputting laser beams are met. Thus, the laser beam generator 3 starts outputting laser beams based on the setup condition (S31).

The current laser beam output power is transmitted to the controller 251*b* via the communication cable 293 from the laser beam generator 3 at a fixed interval (e.g., 1 second). If there is no transmission of the laser beam output power from the laser beam generator 3 (S32: No), the controller 251*b* displays on the user interface 205 that there was a communication error (S35), and prompts the operator to handle it according to the predetermined procedure.

As it receives the laser beam output power transmitted by the laser beam generator 3 (S32: Yes), the controller 251*b* makes a judgment whether the actual laser beam output power is within the tolerance (e.g., ±10% of the setup value) (S33). If the laser beam output power is not within the tolerance (S33: No), the controller 251*b* displays on the user interface 205 that there was an output error (S36), stops the laser emission output (S37), and prompts the operator to handle it according to the predetermined procedure.

Even if the controller 251*b* determines that the laser beam output power is within the tolerance (S33: Yes), it constantly monitors the conditions of various parts of the thermal treatment apparatus while the laser beam is active, and continues to make judgments whether the laser beam can be continued active based on the conditions of various parts (S34). For example, the controller 251*b* deactivates the laser beam by means of stopping the laser beam activation signal transmitted via the footswitch signal cable 291, when the temperature obtained by the detection signal obtained by the mirror temperature sensor 111 becomes higher than the specified temperature (S34: No). The controller 251*b* may also make adjustments such as sending signals to change (increase or decrease) the laser beam output power of the laser beam generator 3 via the transmission cable 293 in accordance with the detection signal of the mirror temperature sensor 111 (S37). The controller 251*b* may also make adjustments or stop the laser beam when it is judged that the laser beam should be deactivated by monitoring the signals from various sensors and the conditions of various parts of the thermal treatment apparatus (S37).

As can be seen from the above, the second embodiment is not only capable of achieving a similar effect as the first embodiment, but also is capable of setting up the laser beam output condition as a treatment condition automatically and securely in order to improve the operating and reliability characteristics. It is also capable of automatically adjusting the laser beam output conditions of the laser beam generator 3 (e.g., changing the laser beam output power) via the communication cable 293, in order to improve the variety of control and the functionality.

Although the mirror temperature sensor was assumed as the detection means for detecting the information concerning the emission function of the laser beam emitted by the laser beam emission part in the descriptions of the thermal treatment apparatuses according to the first and second embodiments, the invention is not limited to it. For example, it is also possible to use a detector that detects the distortion of the laser beam emission part.

Figure 20:
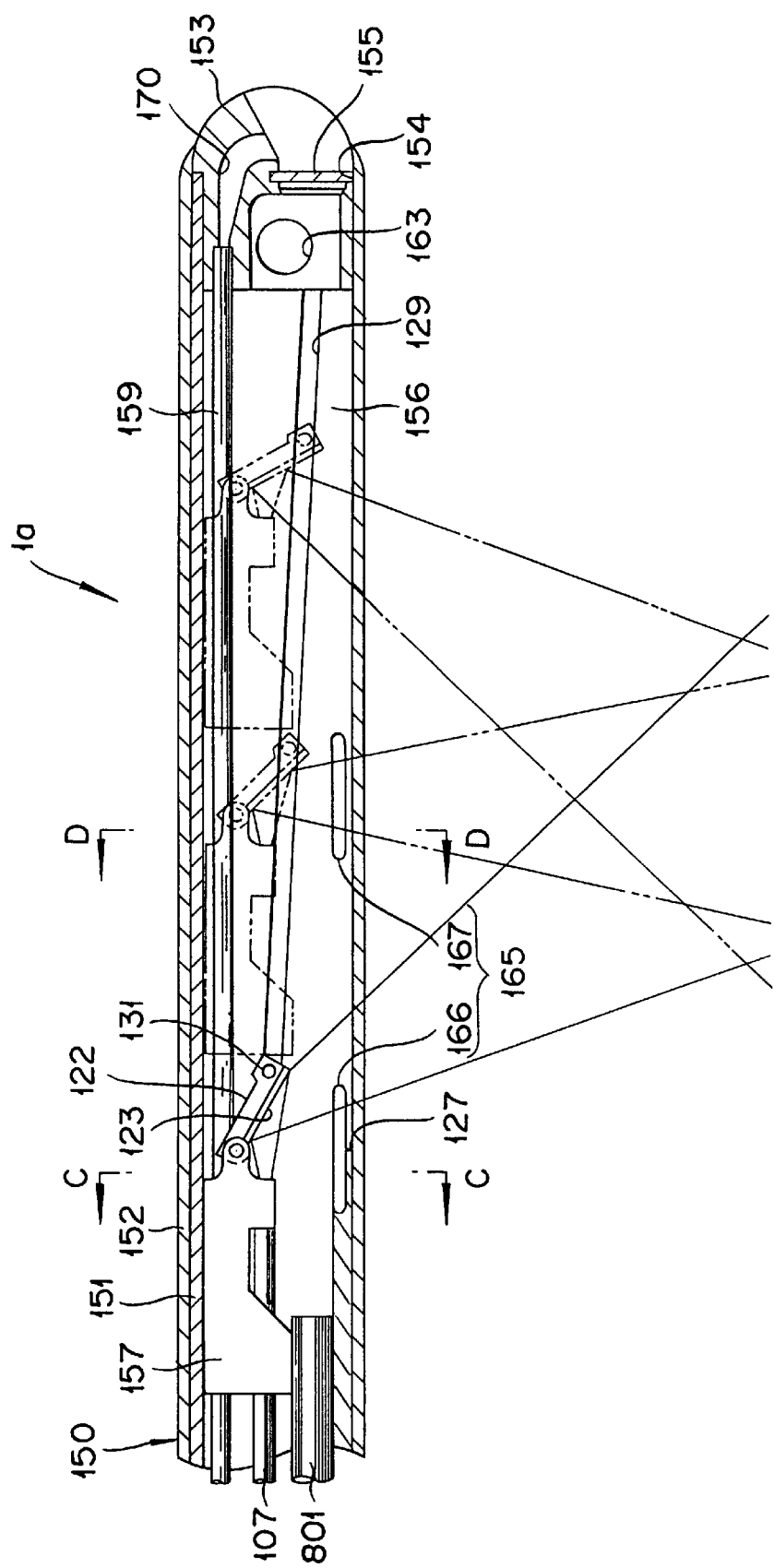
FIG. 20 is a cross section of the distal end of the laser beam irradiation unit used on a thermal treatment apparatus according to the third embodiment of the invention.
Figure 21:
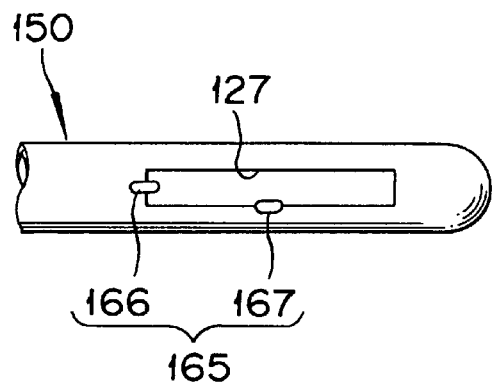
FIG. 21 is a bottom outline view of FIG. 20.
Figure 22:
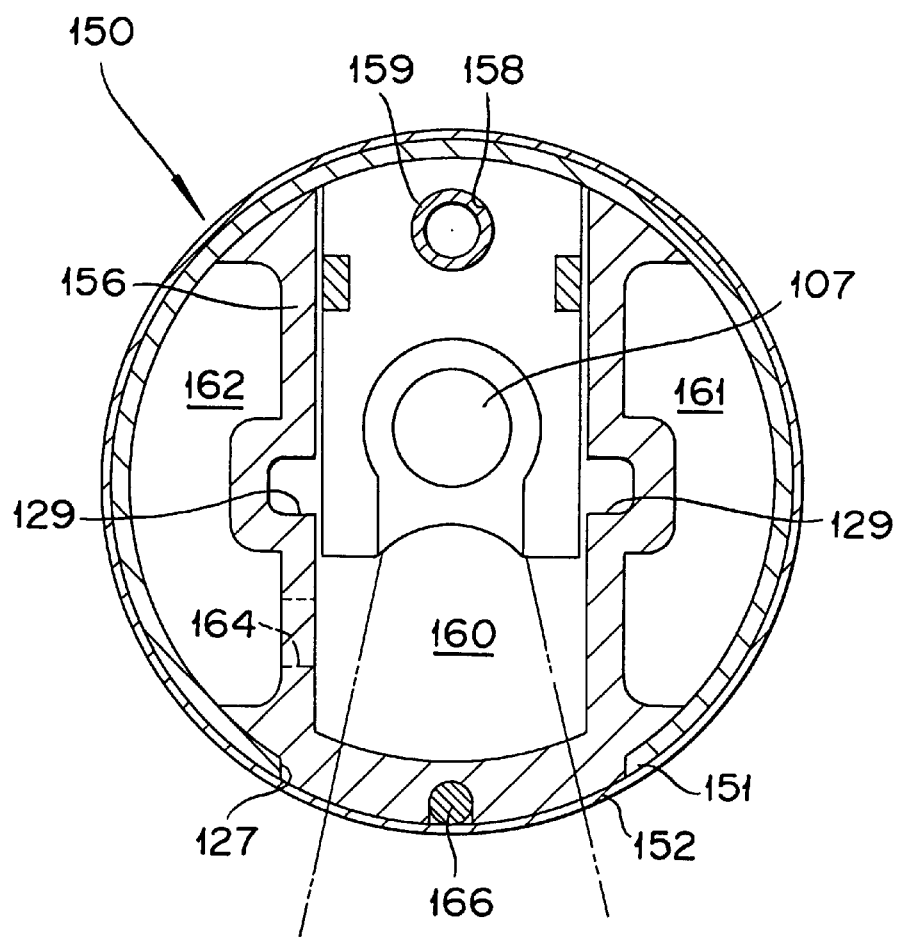
FIG. 22 is a cross section along the line C—C of FIG. 20.
Figure 23:
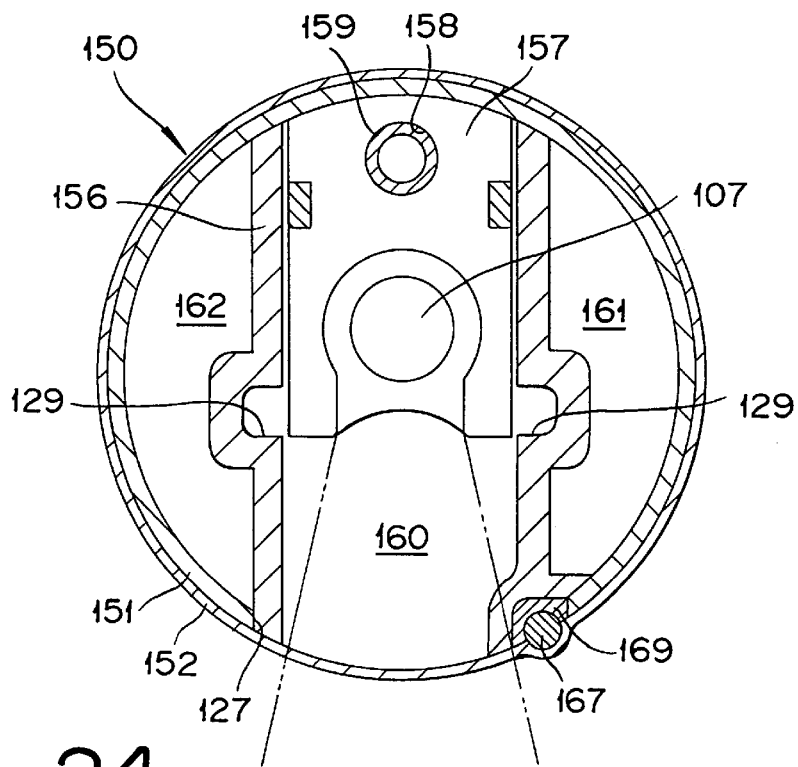
FIG. 23 is a cross section along the line D—D of FIG. 20.

FIG. 20 is a cross section of the distal end of the laser beam irradiation unit used on a thermal treatment apparatus according to the third embodiment of the invention, FIG. 21 is a bottom outline view of FIG. 20, FIG. 22 is a cross section along the line C—C of FIG. 20, and FIG. 23 is a cross section along the line D—D of FIG. 20. The third embodiment will be described bellow primarily concerning with the differences from the first embodiment while omitting descriptions on common parts.

As shown in FIG. 20, a laser beam irradiation unit 1*a* according to the third embodiment comprises an insertion part 150 to be inserted into the living body having a long and slender inner layer pipe 151, and a laser beam emission part 122 contained in the distal end of the insertion part 150 for emitting laser beams. The laser beam emission part 122 has a laser beam reflection surface (mirror) 123 that reflects laser beams.

The inner layer pipe 151 of the insertion part 150 is made of a hard tube-like member made of a material such as stainless steel. The distal end of the inner pipe 151 has a window 127 formed to be an opening for transmitting laser beams. The entire inner pipe 151, which includes the window 127, is covered by an outer tube 152 with a good laser beam transmission capability.

A cap 153 is mounted on the distal end of the inner pipe 151. The cap 153 is provided with a front observation window 154 in order to observe the front direction during the insertion process of the insertion part 150 into the living body. The front observation window 154 has a transparent plate 155 with a good light transmitting capability. A wall member 156 that defines an internal space is provided inside the distal end portion of the insertion part 150. The wall member 156 has a pair of plate-like parts on the left and right sides.

An optical fiber 107 is installed in the inside of the insertion part 150. The proximal end of the optical fiber 107 is connected to the laser beam generator 3 via an optical connector. The optical fiber 107 is entirely covered by a protective pipe made of stainless steel to prevent damages or bends in the insertion part 150 except the distal end part. A laser beam emission part 122 is pivotably mounted on a fixed member 157, which is affixed in the vicinity of the distal end of the optical fiber 107. A pipe 159 is inserted into a through hole formed on the fixed member 157. Thus, the fixed member 157 can slide along the pipe 159. Also, washing water can be supplied through the inside of the pipe 159. The washing water flows outside of the transparent plate 155 after being bent toward the front observation window 154 by a flow path 170 formed inside the cap 153.

A pair of protrusions 131 provided on both sides of the distal end of the laser beam emission part 122 is supported by a pair of grooves 129 formed on the wall member 156 slanting relative to the axial direction of the insertion part 150. The optical fiber 107 is connected to the drive unit and is made possible to reciprocate in the axial direction of the insertion part 150. Therefore, when the optical fiber 107 reciprocates, the laser beam emission part 122 attached to the distal end of the optical fiber 107 changes its tilting angle continuously as it reciprocates due to the groove 129.

The cooling water circulates inside the insertion part 150 in order to cool the surface of the vital tissue that receives the laser beam, to cool the laser beam emission part 122 inside the insertion part 150, etc. The cooling water supplied through the water supply tube 272 flows into a lumen 160, then flows into a lumen 161 through a hole 163 in the vicinity of the insertion part 150, and will be discharged through the drain tube 273. The cooling water flows from a hole 164 formed on the wall member 156 into a lumen 162.

The endoscope 801 is placed in the inside of the insertion part 150. The endoscope 801 is inserted from the proximal side of the laser beam irradiation unit 1a, and is made possible to move in the axial direction inside the insertion part 150. The endoscope 801 has a suitable field of view to capture a field of view through both the window 127 and the front observation window 154. The endoscope 801 is not shown in the drawing in FIG. 22 through FIG. 24.

In this third embodiment, a detection unit 165 is provided for detecting the reciprocating motion of the laser beam emission part 122 that include the mirror 123 as well as the surface temperature of the tissue to be thermally treated, and the operating condition of the laser beam generator 3 is controlled by the control unit 2 using the detection results of the detection unit 165. Such control can be implemented independently or can be implemented arbitrarily in combination with the control of the first and second embodiments.

The detection unit 165 has a reciprocating motion detection sensor 166 that detects the reciprocating motion of the laser beam emission part 122 and a urethra temperature sensor 167 that detects the temperature of the urethra wall. The sensors 166 and 167 are located in a compartment formed in the wall member 156. As shown in FIG. 23, adhesive 169 can be used for installing the sensor 166. Thermistors are used as the sensors 166 and 167. However, other temperature measuring sensors such as thermocouples may be used as well. The sensor 166 can be a sensor such as a photoelectric element capable of detecting laser beams.

The reciprocating motion detecting sensor 166 is located near the rear end of the reciprocating motion of the laser beam emission part 122, i.e., near the rear end of the window 127. Thus, it is possible to detect the laser beam emitted from the laser beam emission part 122 when the laser beam emission part 122 is at the rear end (location indicated by solid lines in FIG. 20) as shown in FIG. 20. The reciprocating motion of the laser beam emission part 122 is detected by measuring the detection time interval at the reciprocating motion detection sensor 166.

Figure 25:
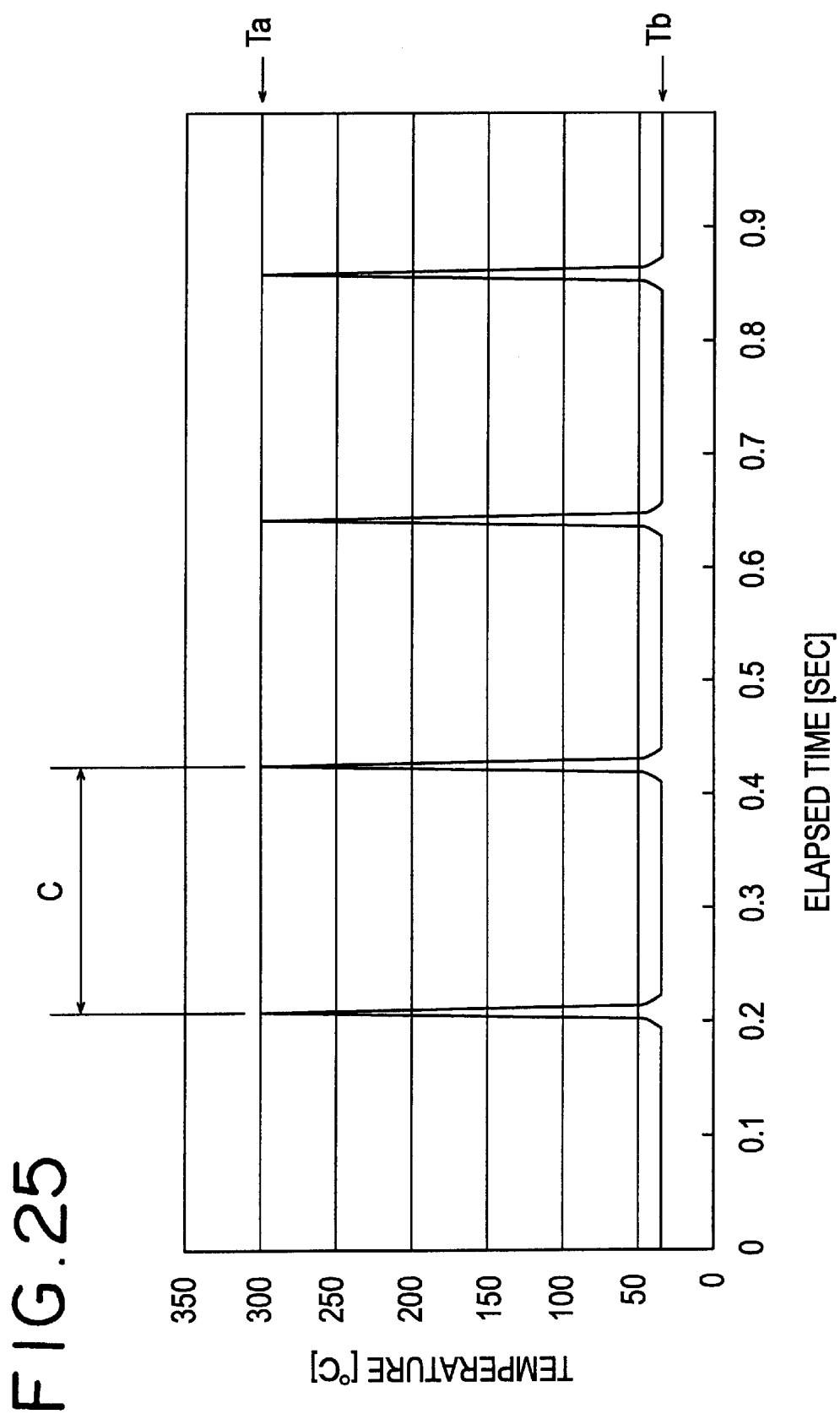
FIG. 25 is a diagram showing the detected values of the reciprocating motion detection sensor.

FIG. 25 is a diagram showing the detected values of the reciprocating motion detection sensor. When it receives the laser beam emitted by the laser beam emission part 122, the reciprocating motion detection sensor 166 outputs instantaneously a peak signal Ta larger than normal. The reciprocating motion detection sensor 166 outputs a normal signal Tb, which is lower than said peak signal Ta, when it is not receiving laser beams. FIG. 25 shows the detection value when the laser beam emission part 122 reciprocates at the frequency of, for example, 5 Hz, indicating that the peak signal Ta is appearing at approximately every 0.2 seconds. The operating condition of the laser beam emission part 122 concerning the laser beam traveling irradiation can be known by measuring the time interval, i.e., the cycle C, of the peak signal Ta detected by the reciprocating motion detection sensor 166. The reciprocating motion detection sensor 166 can be provided at the front end position or the rear end position of the reciprocating motion of the laser beam emission part 122. This makes it possible to check whether the operation of the laser beam emission part 122 is a proper one in a short time. Further, even if different travel speeds are used for coming and going, it is possible to check the operating condition of the laser beam emission part 122 on each travel.

The urethra temperature sensor 167 is placed in the side vicinity of the center of the window 127. This makes it possible to detect the urethra wall temperature Tc more securely without interference to the laser beam irradiation of the tissue.

Figure 24:
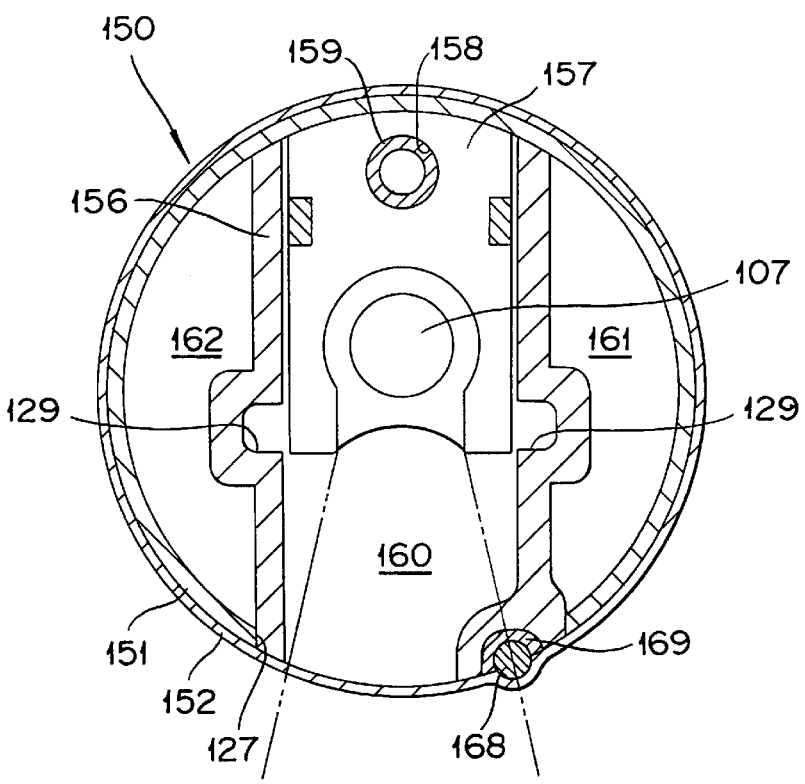
FIG. 24 is a cross section along the line D—D of FIG. 20 showing a modified example of the detection unit.

The detection unit 165 can be constituted in such a way, as shown in FIG. 24, as to have only one detection sensor 168 for detecting both the reciprocating motion of the laser beam emission part 122 and the urethra temperature. This detection sensor 168 is located in the side vicinity of the center of the window 127 as in the case of the urethra temperature sensor 167, it is placed slightly closer to the center of the window 127 as shown in FIG. 24 than the urethra temperature sensor 167 shown in FIG. 23 for the convenience of detecting the laser beam. In this configuration, the urethra temperature can be found out from the normal signal Tb that corresponds to the signal obtained by cutting the peak signal Ta as shown in FIG. 25.

Figure 26:
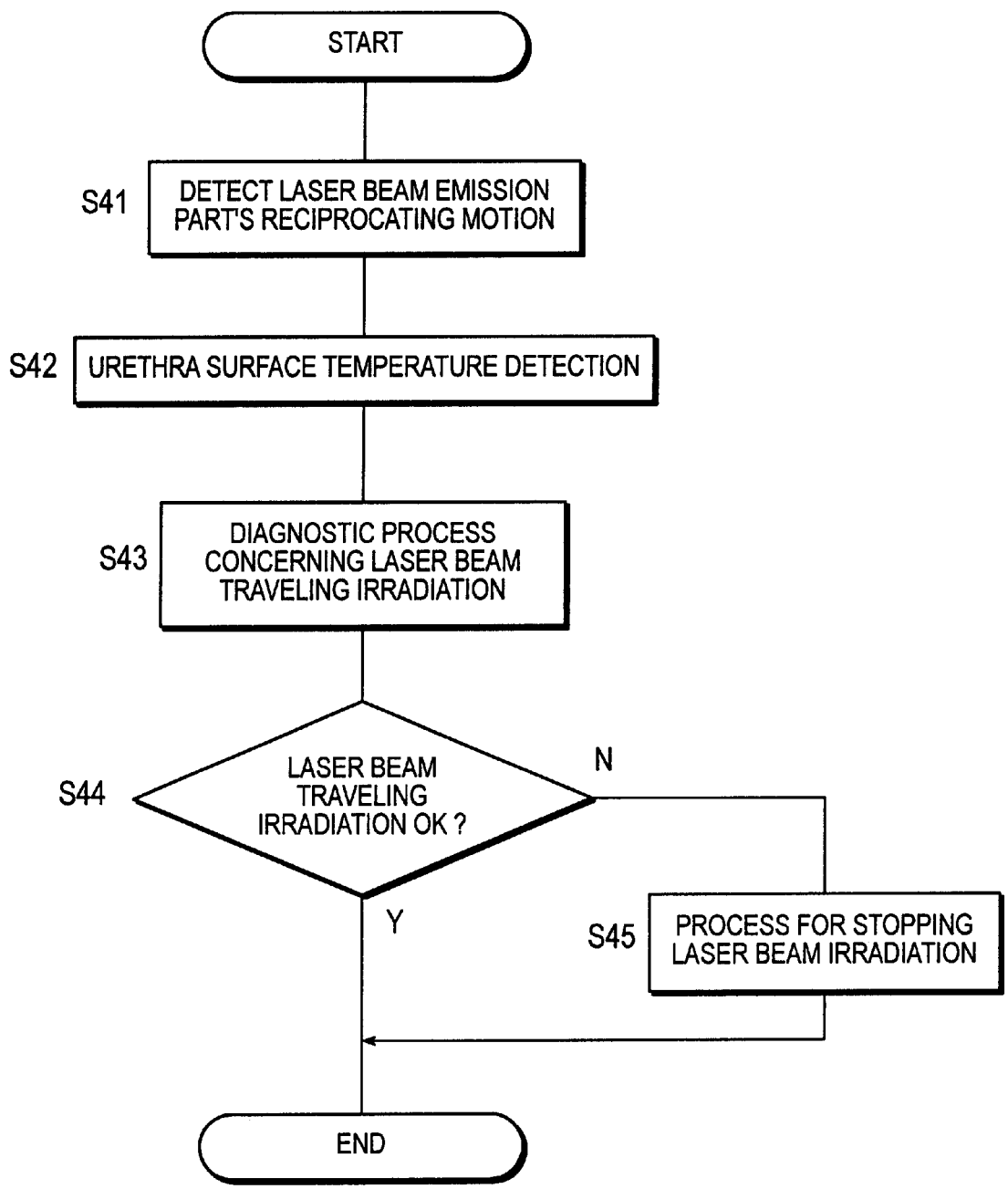
FIG. 26 is a flowchart showing the control sequence concerning the laser beam traveling irradiation of the thermal treatment apparatus according to the third embodiment of the invention.

Next, the control sequence concerning the laser beam traveling irradiation will be described below with reference to FIG. 26.

First, the reciprocating motion of the laser beam emission part 122 is detected based on the signal from the reciprocating motion sensor 166. Specifically, the peak signal Ta, the peak-to-peak cycle C, etc., are detected based on the detection values of the reciprocating motion detection sensor 166 (S41).

Further, the surface temperature of the urethra is detected based on the signal from the urethra temperature sensor 167 (S42).

Next, based on the detection results at the step S41 and S42, the diagnostic process concerning the laser beam traveling irradiation will be conducted (S43). The diagnostic process will be conducted according to the diagnostic table shown in FIG. 27A and FIG. 27B. The diagnostic table shown in FIG. 27A and FIG. 27B is only an example and is prepared and stored in the memory unit beforehand, but the operator or the manager of the apparatus can also arbitrarily modify it.

According to FIG. 27A and FIG. 27B, it is diagnosed normal and the laser beam traveling irradiation is considered adequate if the peak-to-peak cycle C is constant (i.e., the variation range for the predetermined cycle is less than a predetermined percentage), and the urethra surface temperature Tc is within the preset range (e.g., 20 through 45° C.).

Even if the urethra surface temperature Tc is within the preset range, the driving condition of the laser beam emission part is judged to be unacceptable and the motion instability exists, if the peak-to-peak cycle C is unstable. This is suspected to be caused by either the problems in the drive system, problems in the mirror motion, or problems in the transmission system. The problems of the drive system include operation errors, backlash, motor problems and power source problems; the mirror motion problems include backlash and overloading; and the transmission system problems include overloading to the probe. Even if the urethra surface temperature Tc is within the preset range, the driving condition of the laser beam emission part is judged to be unacceptable and the motion is considered too fast, if the peak-to-peak time span is too small. This is suspected to be caused by problems of the driving system, etc. The driving system problems in this case include operation errors, motor problems, power source problems, and broken parts. Even if the urethra surface temperature Tc is within the preset range, the driving condition of the laser beam emission part is judged to be unacceptable and the motion is considered too slow, if the peak-to-peak time span is too large. This is suspected to be caused by problems of the driving system, etc. The driving system problems in this case include operation errors, motor problems, and power source problems. Even if the urethra surface temperature Tc is within the preset range, the driving condition of the laser beam emission part or the laser beam reflection condition is judged to be unacceptable and the motion is considered stopped, if no peak-to-peak signals can be detected. This is suspected to be caused by problems in the driving system, problems in the mirror motion, or problems of the transmission system, etc. The driving system problems in this case include operation errors, backlash, motor problems, and power source problems; the mirror motion problems include backlash and overloading; and the transmission system problems include overloading to the probe.

Furthermore, even if the peak-to-peak cycle C is constant, the laser beam output is judged to be inappropriate and the laser beam output value is considered too small, if the peak signal Ta is lower than the preset range and the urethra surface temperature Tc is within the preset range. This is suspected to be caused by light source problems or optical component problems. The light source problems in this case include lowering of the laser beam output; and the optical component problems include optical fiber breakage, mirror grinding problems and mirror burning. Also, even if the peak-to-peak cycle C is constant, the laser beam output is judged to be inappropriate and the laser beam output value is considered too large, if the peak signal Ta is higher than the preset range and the urethra surface temperature Tc is within the preset range. This is suspected to be caused by light source problems or setup errors. The light source problems in this case include rising of the laser beam output and the setup errors include the laser beam output power setup errors caused by the operator.

Moreover, even if the peak-to-peak cycle C is constant, the laser beam output or cooling is judged to be inappropriate and it is considered either that the laser beam output is too small or the cooling is too much, if the urethra surface temperature Tc is lower than the preset range. This is suspected to be caused by light source problems, optical component problems, or cooling system problems. The light source problems in this case include lowering of the laser beam output; the optical component problems include optical fiber breakage, mirror grinding problems and mirror burning; and the cooling system problems include the case where the coolant water flow is too much and the case where the coolant water temperature is too low. Also, even if the peak-to-peak cycle C is constant, the laser beam output or cooling is judged to be unacceptable and it is considered either that the laser beam output is too large or that the cooling is insufficient, if the urethra surface temperature Tc is higher than the preset range. This is suspected to be caused by light source problems, setup errors, or cooling system problems. The light source problems in this case include rising of the laser beam output; the setup errors include the laser beam output power setup errors caused by the operator; and the cooling system problems include the case where the coolant water flow is too little and the case where the coolant water temperature is too high.

Next, at the step S43, a judgment is made whether the laser beam traveling irradiation has been diagnosed proper (S44).

If the laser beam traveling irradiation is diagnosed not proper (S44: No), the control unit will terminate the laser beam activation signal in order to stop the operation of the laser beam generator 3 and/or do other process (S45). The system can inform the operator about the result of the diagnosis concerning the laser beam traveling irradiation obtained at the step S43. Thus, the operator can take a more appropriate measure against the result of the diagnosis.

As can be seen from the above, the third embodiment makes it possible to directly monitor the laser beam traveling irradiation, i.e., the emission operation itself of the laser beam by the laser beam emission part that moves continuously. Therefore, it is possible to detect more quickly and securely whether the tissue being treated is properly irradiated with laser beams. Thus, it is possible to achieve a better treatment effect by accurately applying laser beams to the target lesion location.

Figure 28:
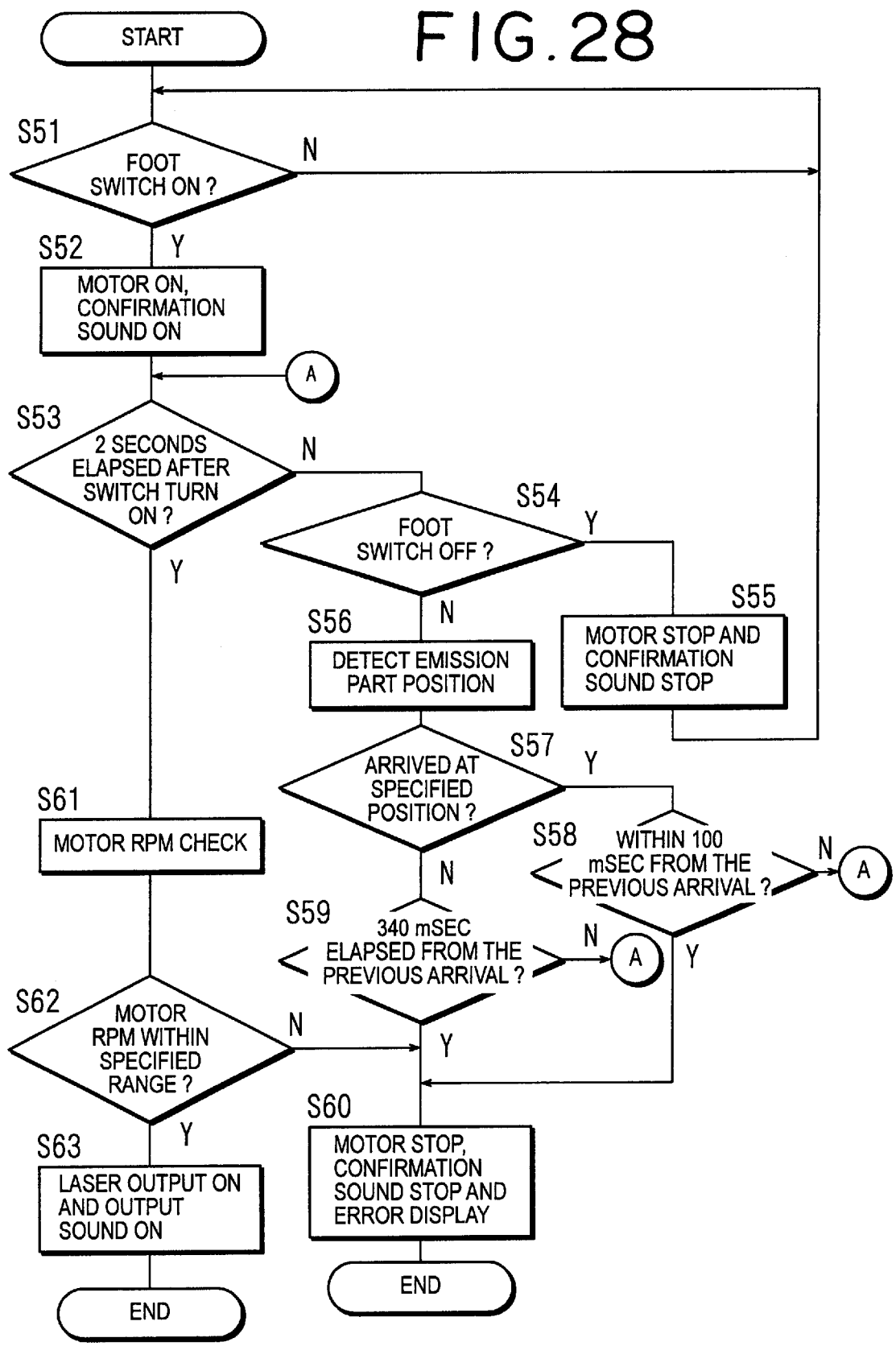
FIG. 28 is a flowchart showing the control sequence concerning the laser beam traveling irradiation of the thermal treatment apparatus according to the fourth embodiment of the invention at the start of the laser beam irradiation.
Figure 29:
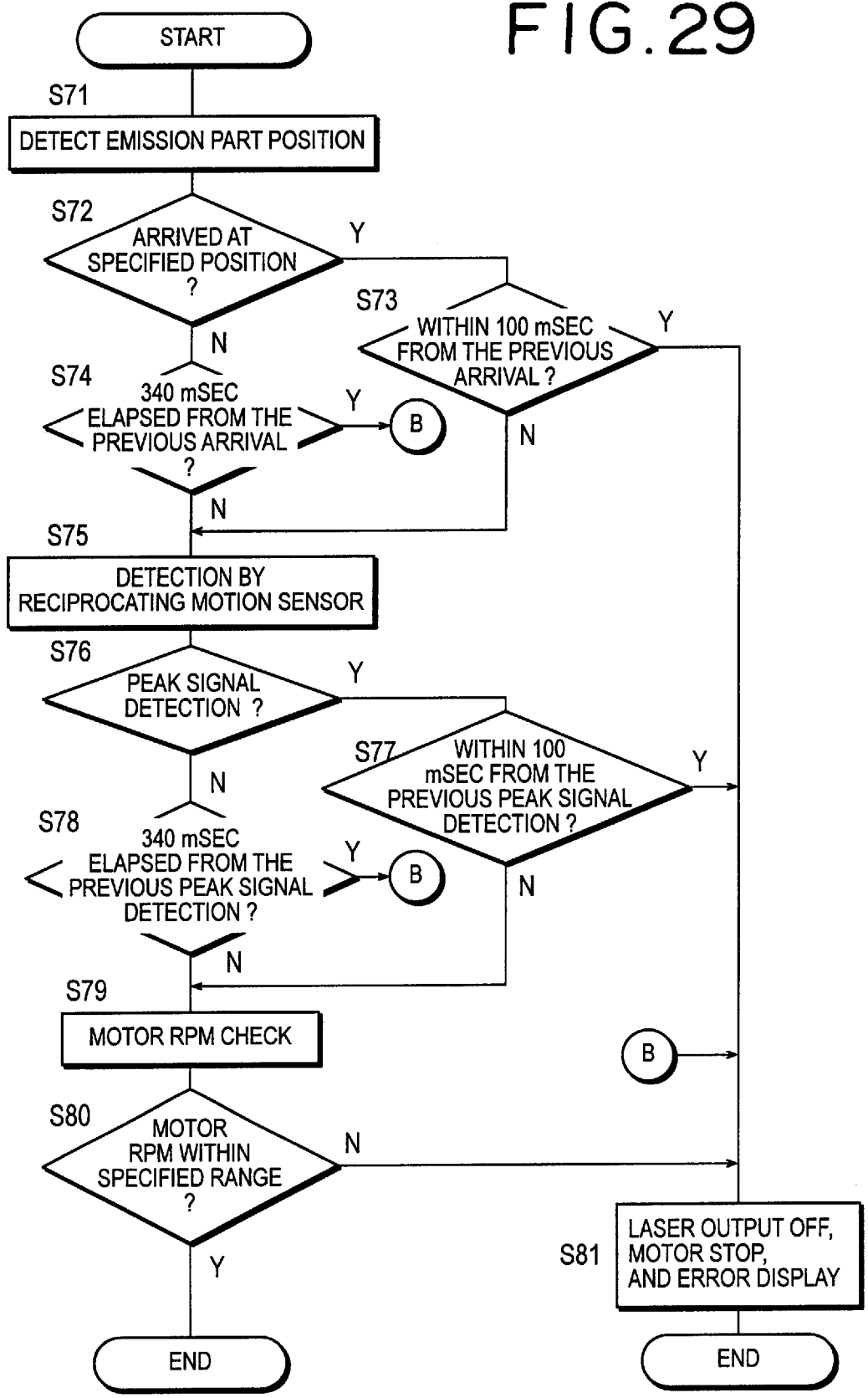
FIG. 29 is a flowchart showing the control sequence concerning the laser beam traveling irradiation of the thermal treatment apparatus according to the fourth embodiment of the invention during the laser beam irradiation.
Figure 30:
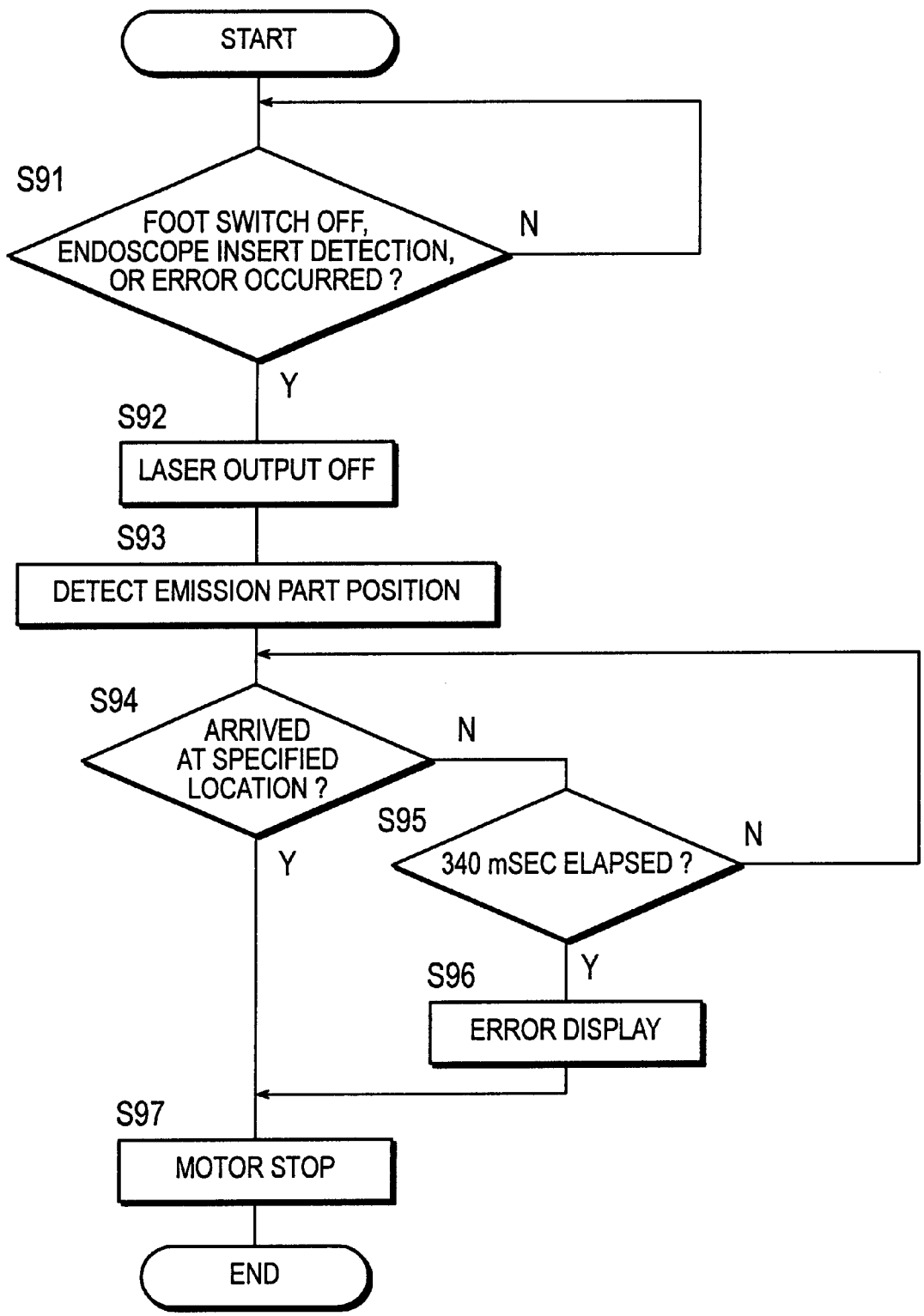
FIG. 30 is a flowchart showing the control sequence concerning the laser beam traveling irradiation of the thermal treatment apparatus according to the fourth embodiment of the invention at the end of the laser beam irradiation.

FIG. 28 through FIG. 30 are flowcharts showing the control sequence concerning the laser beam traveling irradiation of the thermal treatment apparatus according to the fourth embodiment of the invention. The fourth embodiment will be described below primarily with respect to the differences from the third embodiment while omitting a description of parts common to both embodiments.

An emission part position sensor (not shown) is provided in the fourth embodiment for detecting that the laser beam emission part 122 is at the rear end (position shown by solid lines in FIG. 20) . This emission part position sensor is provided preferably at a position suitable for detecting the laser beam emission part 122 itself. However, the emission part position sensor can be located at a position where it is possible to detect the fixed member 157, to which the laser beam emission part 122 is attached and which is located at the distal end of the protective pipe covering the optical fiber 107, or the proximal fixed part of the protective pipe of the optical fiber 107. The constitutions of other parts of the thermal treatment apparatus are similar to those in the third embodiment.

In this fourth embodiment, the reciprocating motion of the laser beam emission part 122 that include the mirror 123 is detected, and the operating condition of the laser beam generator is controlled using said detection results. Such control can be implemented independently or can be implemented arbitrarily in combination with the control of the first through third embodiments.

First, the control sequence concerning the laser beam traveling irradiation at the start of the laser power activation will be described with reference to FIG. 28.

When the foot switch 6 is turned on (S51: Yes), the system turns on the motor 401 of the drive unit 4, and issues a confirmation sound that indicates that the motor 401 is operating (S52). Next, a judgment is made whether a specified time (e.g., 2 seconds) has elapsed since the foot switch 6 was turned on (S53). If the specified time has not yet elapsed (S53: No) and the foot switch 6 is turned off (S54: Yes), the motor 401 will be stopped and the confirmation sound will be stopped as well (S55).

If the specified time has not yet elapsed (S53: No) and the foot switch 6 is not turned off (S54: No), the position of the laser beam emission part 122 is detected (S56) by means of the emission part position sensor, and a judgment is made whether the laser beam emission part 122 has reached the rear end position, which is the specified reference position (S57). The time interval of the laser beam emission part 122 arriving at the rear end position is measured as it makes a reciprocating motion. The arrival of the laser beam emission part 122 to the rear end position means the change of the state of the laser beam emission part 122 at a position, which is not the rear end position, to its state at the rear end position. It is also possible to detect a case where the laser beam emission part 122 has stopped at the rear end position.

When a new arrival of the laser beam emission part 122 to the rear end position is detected (S57: Yes) within, for example, 100 msec of the previous arrival (S58: Yes), it is judged that the traveling speed of the laser beam emission part 122 is too fast, i.e., the reciprocation cycle is too short, causing the motor 401 and the confirmation sound to be stopped and a specified error message to be displayed (S60). On the other hand, if no new arrival of the laser beam emission part 122 to the rear end position is detected (S57: No) and, for example, 340 msec has elapsed since the previous arrival (S59: Yes), it is judged that the traveling speed of the laser beam emission part 122 is too slow, i.e., the reciprocation cycle is too long, hence both the motor 401 and the confirmation sound will be stopped and a specified error message will be displayed (S60). Consequently, the reciprocating motion of the laser beam emission part 122 is proper if the time interval C (msec) of the arrivals of the laser beam emission part 122 is, for example, 100<C<340.

The operation confirmation procedure shown in steps S54 through S60 will be repeated for 2 seconds after the foot switch 6 is turned on. If the motor 401 and the confirmation sound are not stopped during this time (S53: Yes), the rpm of the motor 401 is detected by the encoder, etc. (S61). If the rpm of the motor 401 is within a specified range (S62: Yes), the laser beam output by the laser beam generator 3 will be activated and the output sound that indicates that the laser beam is activated will be sounded (S63).

Therefore, by checking the reciprocating motion of the laser beam emission part 122 for a certain period of time before activating the laser beam, it is possible to prevent the laser beam from being activated when the traveling movement of the laser beam emission part 122 is inappropriate.

It is also possible to start the reciprocating motion of the laser beam emission part 122 and the activation of the laser beam in sequence by operating only the foot switch 6. Moreover, even if the footswitch 6 is turned on by mistake, the laser beam output will not be activated immediately, so that the activation instruction can be cancelled before the laser beam begins to be irradiated.

Next, the control sequence for the laser beam traveling irradiation while the laser beam is activated will be described referring to FIG. 29.

The position of the laser beam emission part 122 is detected by the emission part position sensor while the laser beam is being activated (S71), and a judgment is made whether the laser beam emission part 122 has reached the rear end position, which is the specified reference position (S72). When a new arrival of the laser beam emission part 122 at the rear end position is detected (S73: Yes), and it is, for example, within 100 msec of the previous arrival (S73: Yes), it is judged that the traveling speed of the laser beam emission part 122 is too fast, hence both the laser beam and the motor 401 will be stopped and a specified error message will be displayed (S81). If no new arrival is made to the rear end of the laser beam emission part 122 (S72: No) and 340 msec has elapsed since the last arrival (S74: Yes), it is judged that the traveling speed of the laser beam emission part 122 is too slow, hence both the laser beam emission output and the motor will be stopped and a specified error message will be displayed (S81).

If the time interval C (msec) of the repetitive arrivals of the laser beam emission part 122 at the rear end position due to its reciprocating motion is, for example, 100<C<340, the output value from the reciprocating motion detection sensor 166 is further detected (S75), and a judgment is made whether the peak signal Ta (refer to FIG. 25) is detected (S76). The reciprocating motion detection sensor 166 detects the laser beam emitted by the laser beam emission part 122 when the laser beam emission part 122 is at the rear end position.

If a new peak signal is detected by the reciprocating motion detection sensor 166 (S76: Yes) and it is, for example, within 100 msec from the peak signal detection from the previous peak signal detection (S73: Yes), it is judged that the traveling speed of the laser beam emission part 122 is too fast, hence both the laser beam and the motor 401 will be stopped and a specified error message will be displayed (S81). On the other hand, if no new peak signal is detected by the reciprocating motion detection sensor 166 (S76: No) and, for example, 340 msec has elapsed from the peak signal detection from the previous peak signal detection (S78: Yes), it is judged that the traveling speed of the laser beam emission part 122 is too slow, hence both the laser beam and the motor 401 will be stopped and a specified error message will be displayed (S81).

At the step S79, the rpm of the motor 401 is detected by the encoder, etc. (S79). If the rpm of the motor 401 is not within a specified range (S80: No), both the laser beam and the motor 401 will be stopped and a specified error message will be displayed (S81). The procedure shown in FIG. 29 will be repeated while the laser beam is being activated.

Therefore, by constantly checking the reciprocating motion of the laser beam emission part 122 while the laser beam is being activated, it is possible to prevent the laser beam from continuous activation when the traveling movement of the laser beam emission part 122 is inappropriate. Also, by detecting the laser beam itself emitted by the laser emission part 122 by means of the reciprocating motion detection sensor 166, it is possible to confirm that the laser beam is being emitted.

Next, the control sequence concerning the laser beam traveling irradiation while the laser beam output is stopped will be described with reference to FIG. 30.

The laser beam will be deactivated immediately, when either a laser beam deactivation instruction is issued by turning of f the foot switch 6, or when an insertion of the endoscope 801 into the distal end of the insertion part 150 is detected, or when an error signal is issued (S91: Yes) due to detection of a temperature by the urethra temperature sensor 167 exceeding the specified range, detection of a cooling water temperature exceeding the specified range of the cooling water, etc., during the laser beam is being activated (S92).

Next, the position of the laser beam emission part 122 will be detected by the emission part position sensor (S93), and a judgment will be made whether the laser beam emission part 122 has reached the rear end position, which is the specified reference position (S94). At the time when the laser beam emission part 122 reached the rear end position (S94: Yes), the motor 401 will be stopped (S97). In other words, the laser beam emission part 122 will be positioned and stopped at the rear end position while the laser beam is deactivated.

If the laser beam emission part 122 has not reached the rear end position (S94: No) and, for example, 340 msec has elapsed (S95: Yes), a specified error message will be displayed (S96) and the motor 401 will be stopped (S97).

Therefore, by confirming that the laser emission part 122 has traveled to the rear end position and stopped when the laser beam is deactivated, it is possible to prevent the next step from being initiated while the traveling motion of the laser beam emission part 122 is inappropriate.

When the laser beam emission part 122 is stopped at the rear end position, the laser beam emission part 122 is positioned at the top of the inside of the insertion part 150 as it is tilted closest to the horizontal position in FIG. 20. Therefore, it is possible to move the endoscope 801 without interfering with the laser beam emission part 122 to the distal end of the insertion part 150 when the laser beam is deactivated, thus making it easy to observe the front and side directions with the endoscope 801.

As can be seen from the above, the fourth embodiment makes it possible to directly monitor the reciprocating motion of the laser beam emission part that travels continuously. Therefore, it is possible to detect more quickly and securely a situation where the tissue being treated is improperly irradiated with laser beams due to an improper reciprocating motion of the laser emission part. Thus, it is possible to achieve a better treatment effect by accurately applying laser beams to the target lesion location.

Figure 31:
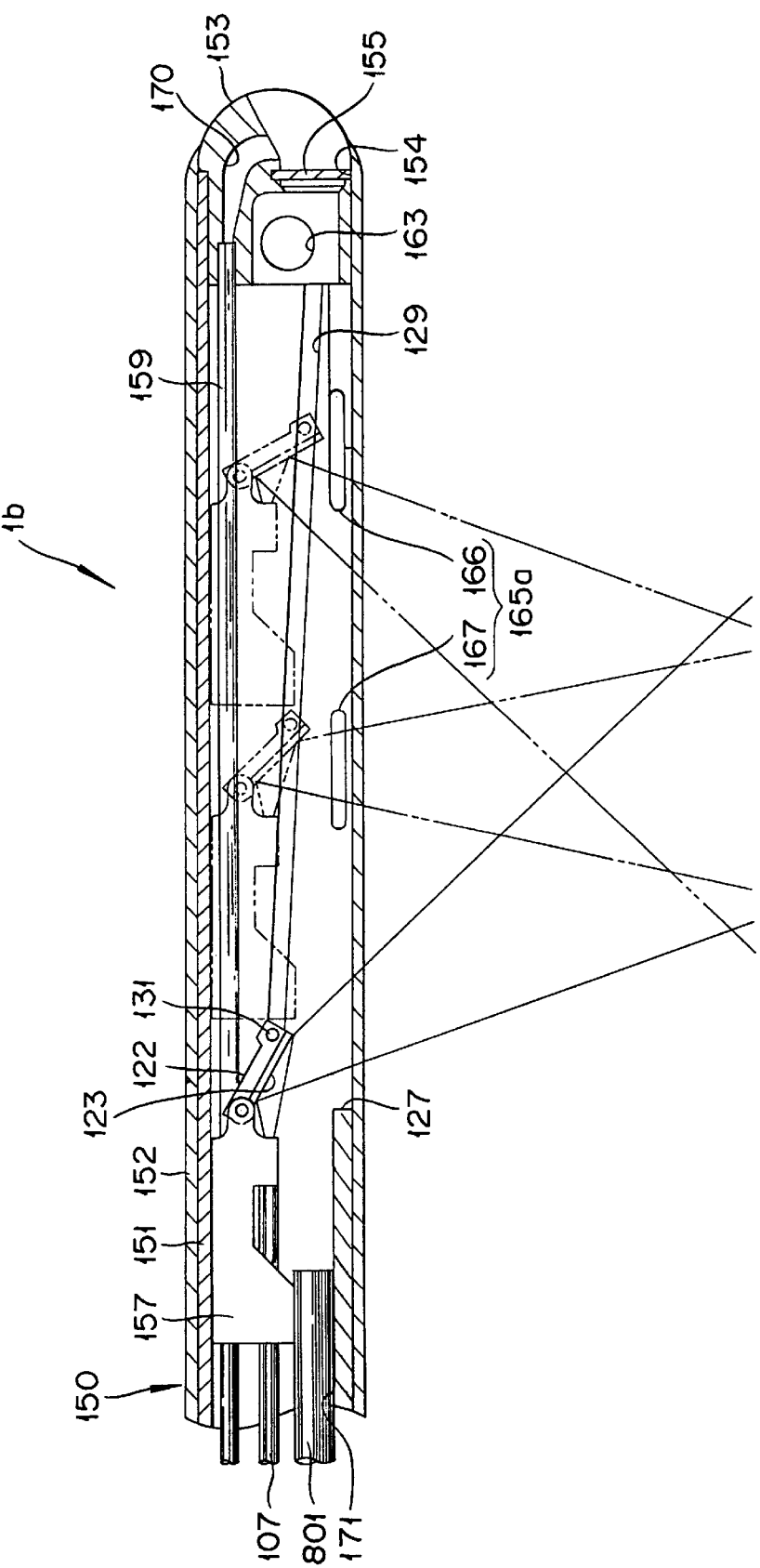
FIG. 31 is a cross section of the distal end of the laser beam irradiation unit used on a thermal treatment apparatus according to the fifth embodiment of the invention.
Figure 32:
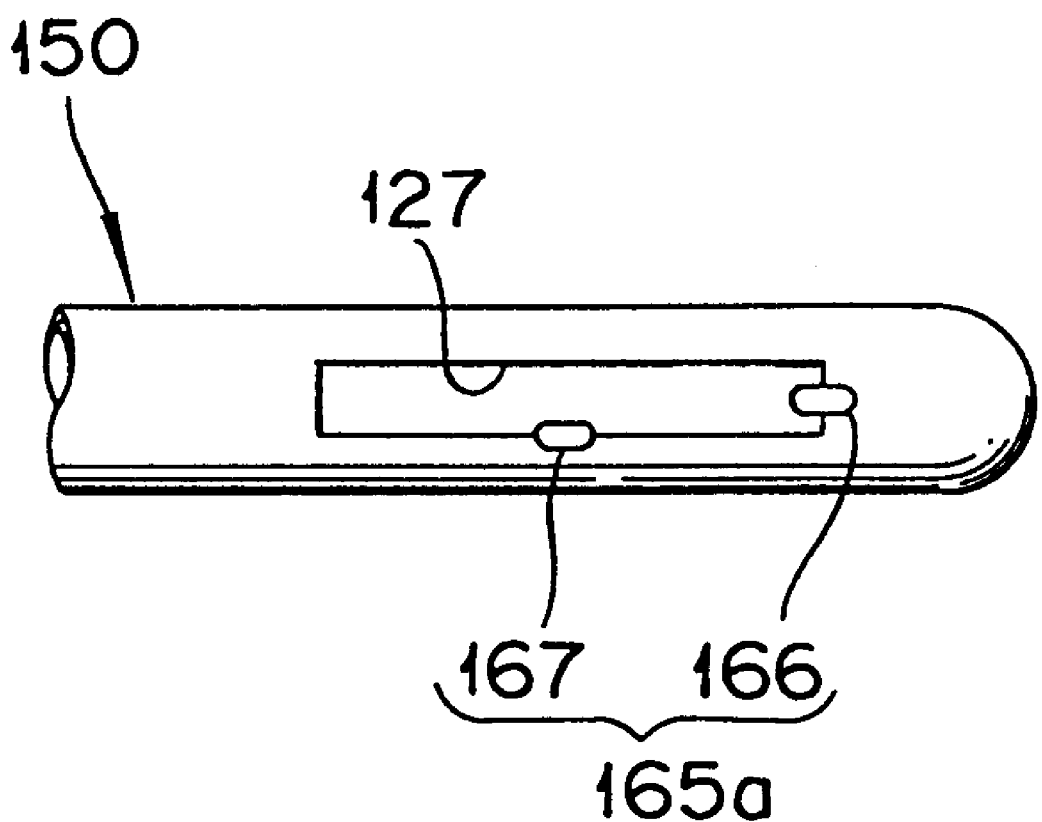
FIG. 32 is a bottom outline view of FIG. 31.

FIG. 31 is a cross section of the distal end of the laser beam irradiation unit used on a thermal treatment apparatus according to the fifth embodiment of the invention and FIG. 32 is a bottom outline view of FIG. 31. The fifth embodiment will be described bellow primarily concerning with the differences from the fourth embodiment while omitting descriptions on common parts.

The laser beam irradiation unit 1b of the fifth embodiment is different from the one used in the fourth embodiment in that the reciprocating motion detection sensor 166 of the detection unit 165a is located in the vicinity of the distal end of the reciprocating motion of the laser beam emission part 122, i.e., the vicinity of the distal end of the window 127. Consequently, as shown in FIG. 31, it can detect the laser beam emitted by the laser beam emission part 122 when the laser beam emission part 122 is at its distal end position (the right side of the two positions indicated by double dot chain lines in FIG. 31). The constitution of the rest of the thermal treatment apparatus will be the same as in the fourth embodiment. The reciprocating motion of the laser emission part 122 is detected by measuring the time interval between detections by the reciprocating motion detection sensor 166 and the emission part position sensor in the fifth embodiment.

Figure 33:
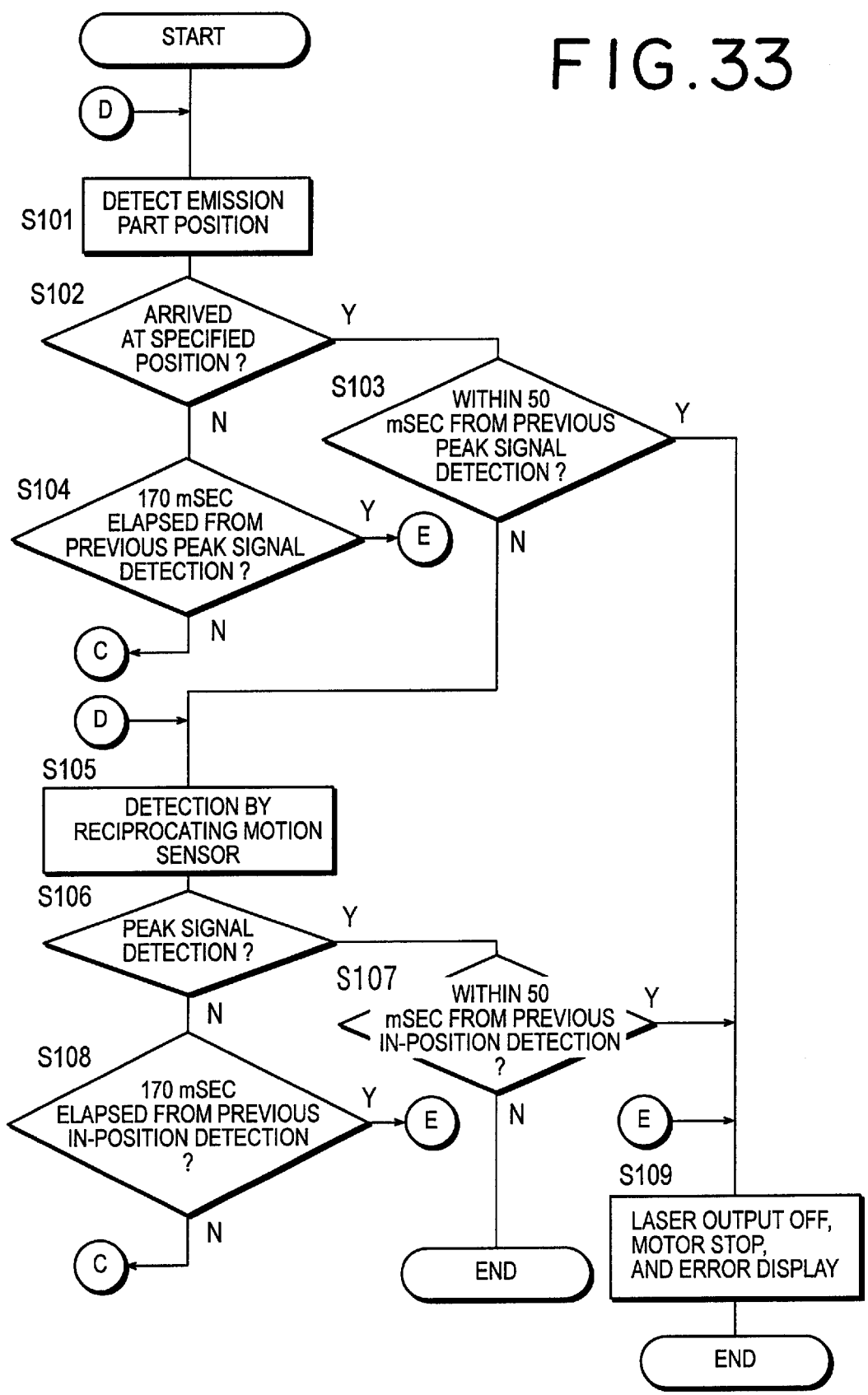
FIG. 33 is a flowchart showing the control sequence concerning the laser beam traveling irradiation of the thermal treatment apparatus according to the fifth embodiment of the invention.
Figure 34:
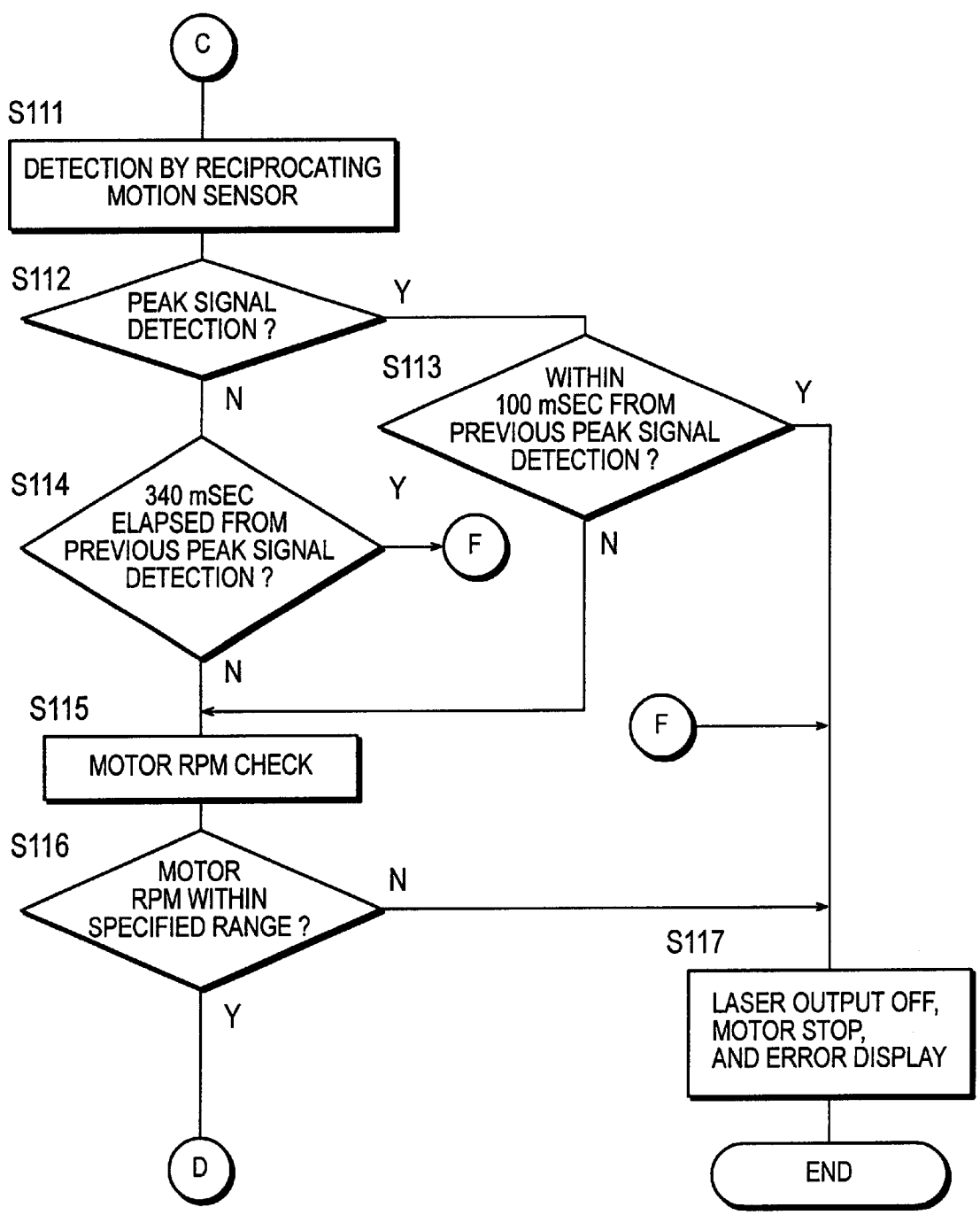
FIG. 34 is a flowchart showing the control sequence concerning the laser beam traveling irradiation of the thermal treatment apparatus according to the fifth embodiment of the invention.

FIG. 33 and FIG. 34 are flow charts showing the control sequence concerning the laser beam traveling irradiation of the thermal treatment apparatus according to the fifth embodiment of the invention.

The control sequence for the laser beam traveling irradiation while the laser beam is activated will be described with reference to FIG. 33 and FIG. 34. As to the control sequences concerning the laser beam traveling irradiation when the laser beam activation is initiated and when the laser beam is deactivated are similar to those in the fourth embodiment.

The position of the laser beam emission part 122 is detected by the emission part position sensor while the laser beam is being activated (S101), and a judgment is made whether the laser beam emission part 122 has reached the rear end position, which is the specified reference position (S102). When a new arrival of the laser beam emission part 122 at the rear endposition is detected (S102: Yes), and it is within, for example, 50 msec of the previous peak signal detection (S103: Yes) detected by the reciprocating motion detection sensor 166, it is judged that the traveling speed of the laser beam emission part 122 is too fast, hence both the laser beam and the motor will be stopped and a specified error message will be displayed (S109). On the other hand, if no new arrival of the laser beam emission part 122 to the rear end position is detected (S102: No) and, for example, 170 msec has elapsed since the previous peak signal detection by means of the reciprocating motion detection sensor 166 (S104: Yes), it is judged that the traveling speed of the laser beam emission part 122 is too slow, hence both the laser beam and the motor will stopped and a specified error message will be displayed (S109).

If the judgment result at the step S103 is negative, the output value from the reciprocating motion detection sensor 166 will be detected (S105), and a judgment will be made if the peak signal Ta (see FIG. 25) has been detected (S106). The reciprocating motion detection sensor 166 detects the laser beam itself emitted by the laser emission part 122 while the laser emission part 122 is at the distal end.

If a new peak signal is detected by the reciprocating motion detection sensor 166 (S106: Yes) and it is, for example, within 50 msec from the previous arrival at the rear end position detection detected by the emission part position sensor (S107: Yes), it is judged that the traveling speed of the laser beam emission part 122 is too fast, hence both the laser beam and the motor will be stopped and a specified error message will be displayed (S109). On the other hand, if no new peak signal is detected by the reciprocating motion detection sensor 166 (S106: No) and, for example, 170 msec has elapsed since the previous arrival at the rear end position detection detected by the emission part position sensor (S108: Yes), it is judged that the traveling speed of the laser beam emission part 122 is too slow, hence both the laser beam and the motor 401 will be stopped and a specified error message will be displayed (S109).

If the judgment result at the step S104 or S108 is negative, the process shown in FIG. 34 will be executed. However, since the processes at the step S111 through S117 of FIG. 34 are similar to the processes at the step S75 through S81 of FIG. 29, their descriptions are not repeated here. If the processes shown in FIG. 34 are executed following the process of the step S104 of FIG. 33, it advances to the step S101 of FIG. 33 if the judgment at the step S116 of FIG. 34 is affirmative, while if the processes shown in FIG. 34 are executed following the process of the step S108 of FIG. 33, it advances to the step S105 of FIG. 33 if the judgment at the step S116 of FIG. 34 is affirmative. The sequences shown in the flowcharts of FIG. 33 and FIG. 34 are repeated while the laser beam is activated.

Consequently, in addition to the fact that the same effects as the fourth embodiment can be achieved, the fifth embodiment will be able to detect the operating condition of the laser beam emission part 122 in each pass even if different traveling speeds are set up for the going and coming passes of the reciprocating motion by means of changing the setup positions of the reciprocating motion detection sensor 166 without adding any new sensors. Moreover, it is capable of detecting whether the motion of the laser beam emission part 122 is appropriate more quickly.

Figure 35:
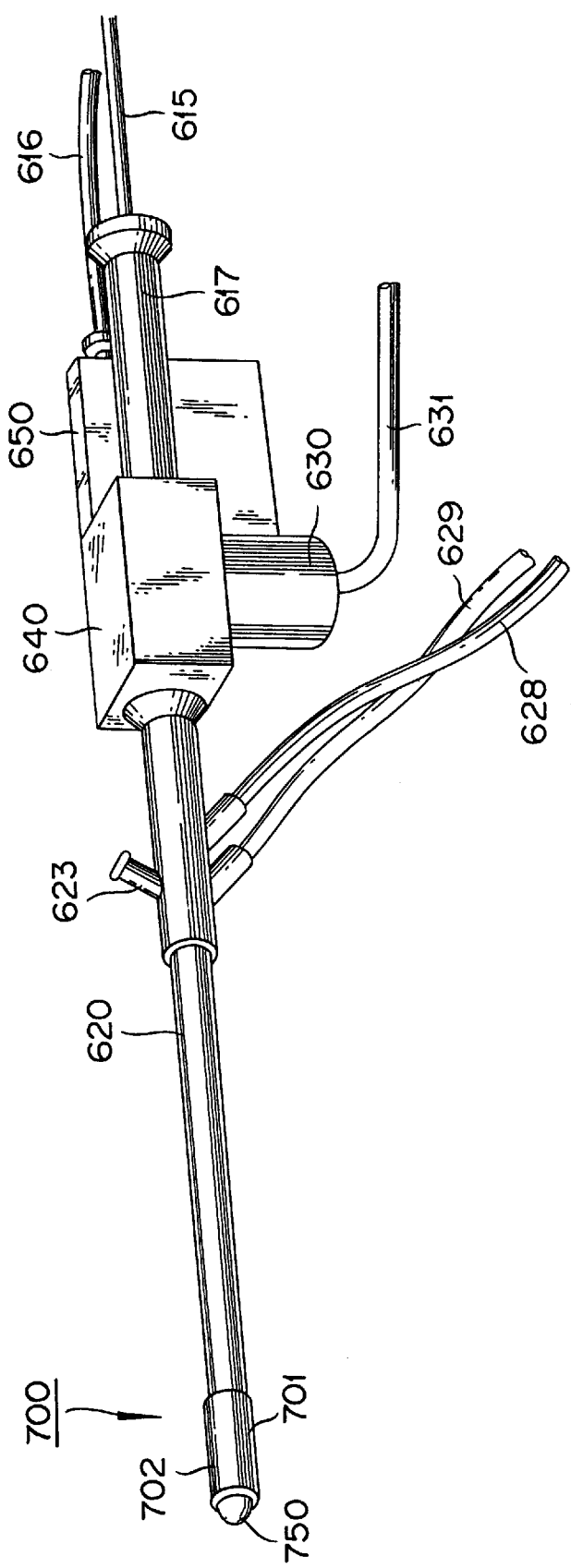
FIG. 35 is a perspective drawing of a laser beam irradiation unit used on a thermal treatment apparatus according to the sixth embodiment of the invention.
Figure 36:
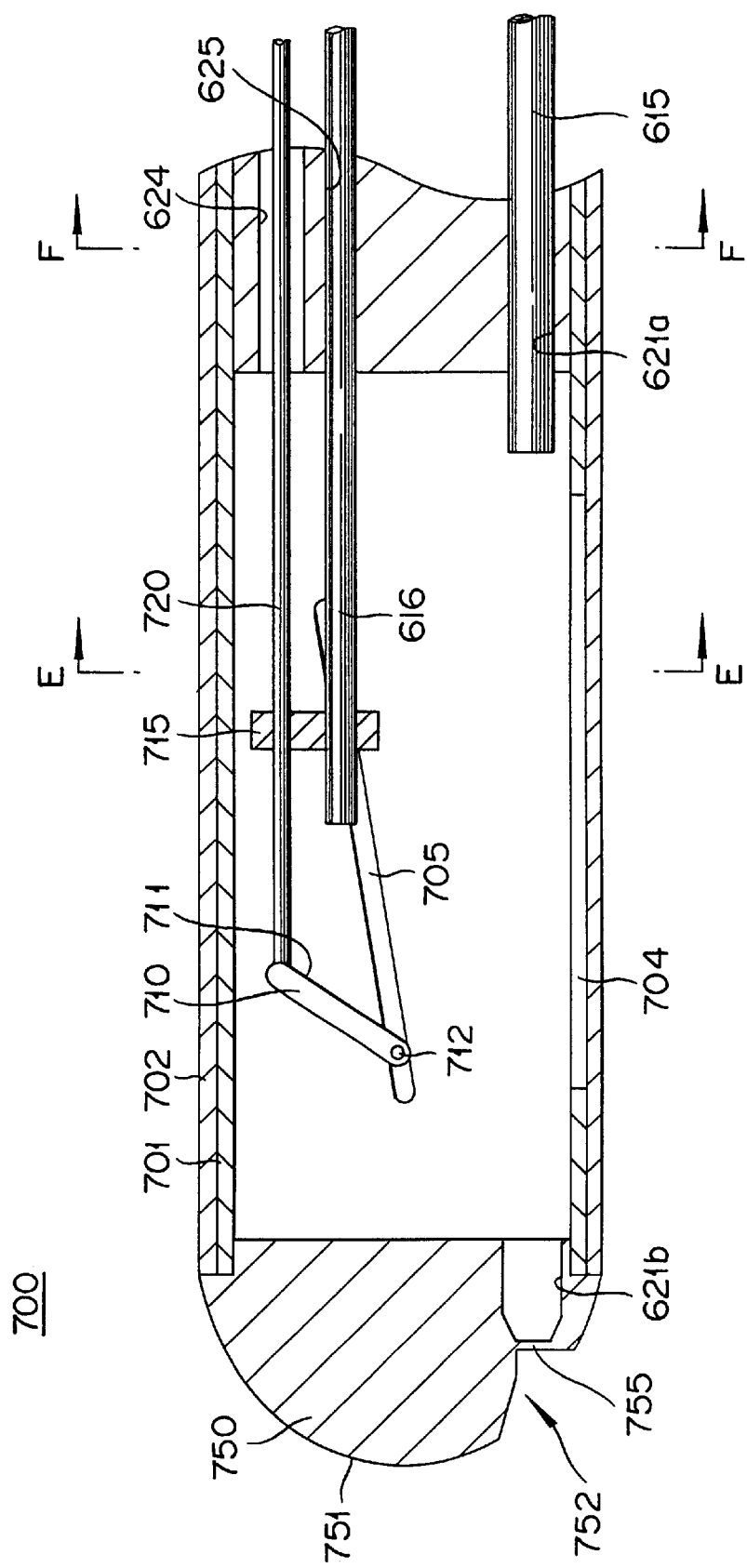
FIG. 36 is a drawing for describing the internal construction of the insertion part of the laser beam irradiation unit.
Figure 37:
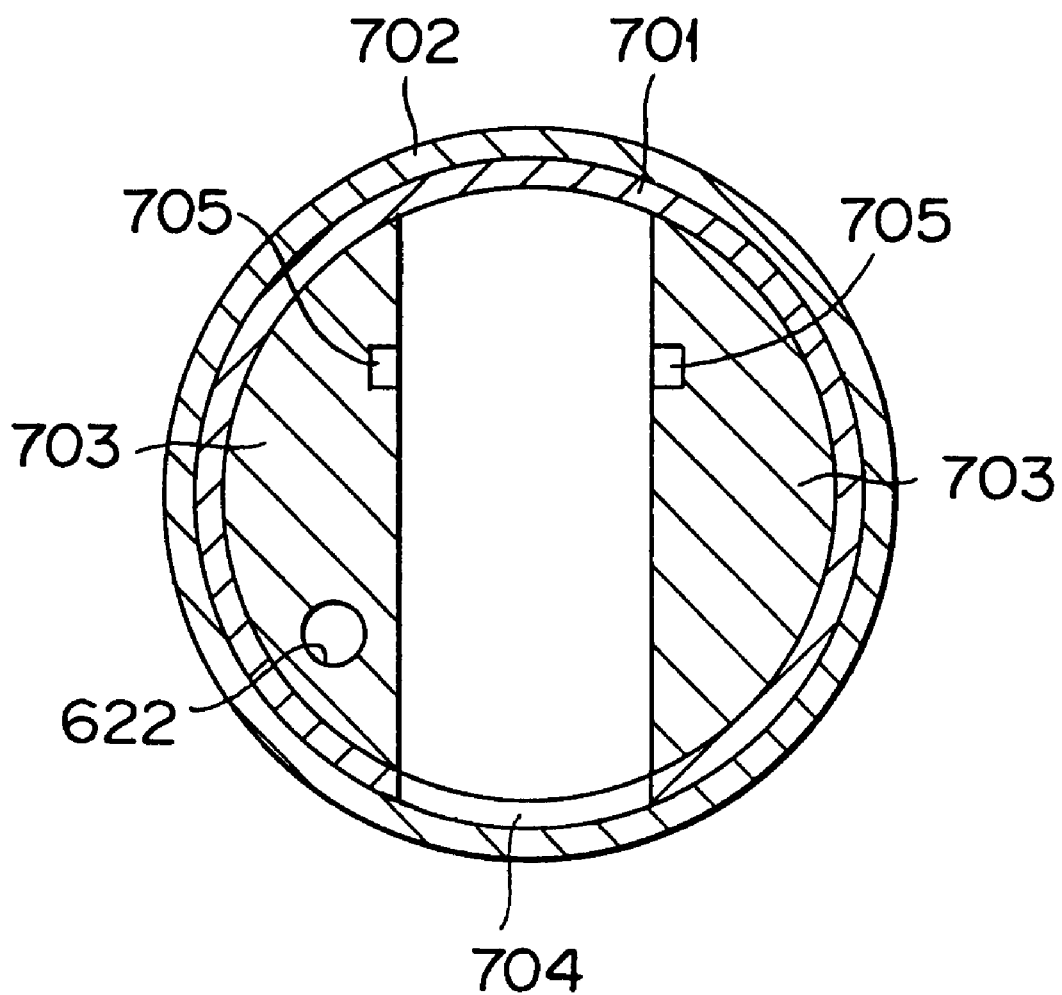
FIG. 37 is a cross section along the line E—E of FIG. 36.

FIG. 35 is a perspective drawing of a laser beam irradiation unit used on a thermal treatment apparatus according to the sixth embodiment of the invention, FIG. 36 is a drawing for describing the internal construction of the insertion part 700 of the laser beam irradiation unit 1c, and FIG. 37 is a cross section along the line E—E of FIG. 36.

The laser beam irradiating unit 1c has a long and slender main body 620, a drive unit 630, a cam box 640, a cushioning unit 650, and an endoscope 615.

An insertion part 700 to be inserted into the living body is formed at the distal end of the main body 620. The insertion part 700 has a housing 701, a covering member 702, and an end cap 750. The housing 701 is a hard tube-like member having a side window 704 provided for both laser beam emitting and side observation and is covered by a covering member 702 with a good laser beam transparency. The inside of the housing 701 is provided with a pair of wall members 703 affixed there to define the internal space of the housing 701. In order to make the inside of the housing 701 an enclosed system, the housing 701 is closely fitted with the end cap 750. The end cap 750 has a front observation window 755 to have the front view of the insertion part 700.

An optical fiber 616 is placed in the inside of the main body 620 and the housing 701. The proximal end of the optical fiber 616 is connected to the laser beam generator via an optical connector.

An emission part 710 for emitting laser beams sideways from the insertion part 700 is contained in the inside of the housing 701. one end of an arm 720 is connected to the emission part 710. The connection point between the emission part 710 and the arm 720 forms a hinge mechanism. The other end of the arm 720 is connected to a cam mechanism within the cam box 640. The cam mechanism converts the rotating motion of the drive unit 630 into a reciprocating motion in the longitudinal direction of the main body 620. Therefore, the arm 720 makes a reciprocating motion driven by the drive unit 630 and the emission part 710 makes a reciprocating motion as they are linked together. The drive unit 630 receives electric power from an electric power source (not shown) via a cable 631.

A pair of protrusion 712 is formed on both sides of the emission part 710. The protrusions 712 engage slidably with a pair of rail grooves 705 provided on wall members 703 of the housing 701. The rail groove 705 is non-parallel with the reciprocating direction of the arm 720. Therefore, the emission part 710 changes its angle according to the position of the arm 720 and the rail groove 705.

A flat reflecting surface 711 is formed on one side of the emission part 710 for reflecting the laser beam. The laser beam is cast on the reflecting surface 711 from the optical fiber 616 and the reflected laser beam passes through the side window 704 to be irradiated on the lesion.

The distal end of the optical fiber 616 is connected with the arm 720 via a connecting member 715. Thus, while the optical fiber 616 and the arm 720 reciprocate together as a unit, the positional relation between the reflecting surface 711 and the distal end of the optical fiber 616 is maintained approximately constant.

The cushioning unit 650 stores the optical fiber 616 in a loop shape and affixes its base. Therefore, the reciprocating motion of the optical fiber 616 inside the housing 701 and the main body 620 is converted into contraction and expansion of the loop inside the cushioning unit 650. Thus, the motion and load of the optical fiber 616 is absorbed and the optical fiber 616 does not move toward the outside of the laser irradiation unit 1c.

The endoscope 615 is fixed in a straight-line shape and is protected from damage and bending as it is covered by a protective pipe made of stainless pipe except the distal end located inside the internal space of the housing 701. The endoscope 615 is inserted into an endoscope guide lumen 621 (621a, 621b) via an endoscope tube 617. The endoscope guide lumen 621 consists of an endoscope guide lumen 621a formed on the side of the main body 620 and an endoscope guide lumen 621b formed on the side of the end cap 750, and serves as a passage for guiding the endoscope 615 to the vicinity of the front observation window 755 and the side observation window 704.

The endoscope 615 is movable in the longitudinal direction of the main body 620. The endoscope 615 travels maintaining its straight-line shape without bending, so that it does not move away from the guide lumen 621 even if the internal space of the housing 701 exists between the guide lumens 621a and 621b.

The endoscope 615 has a preferable view for observing the inside of the living body through the side window 704 and the front observation window 755. Consequently, placing the endoscope 615 near the side window 704 makes it possible to view the sideways from the insertion part 700 and placing it near the front observation window 755 makes it possible to view the front. Thus, observation of the surface layer of the tissue, positioning of the housing 701 based on the observation, and visual confirmation of the laser beam irradiation position can be easily done.

The endoscope 615 has a filter function for cutting out the wavelength region irradiated by the optical fiber 616. This filter function is provided between the endoscope 615 and the monitor for displaying the image of said endoscope 615, or in the endoscope 615. Therefore, the laser beam can be prevented from entering the operator's eyes when observing the inside of the living body using the endoscope.

Next, the specific structure of the end cap 750 will be described.

Figure 38A:
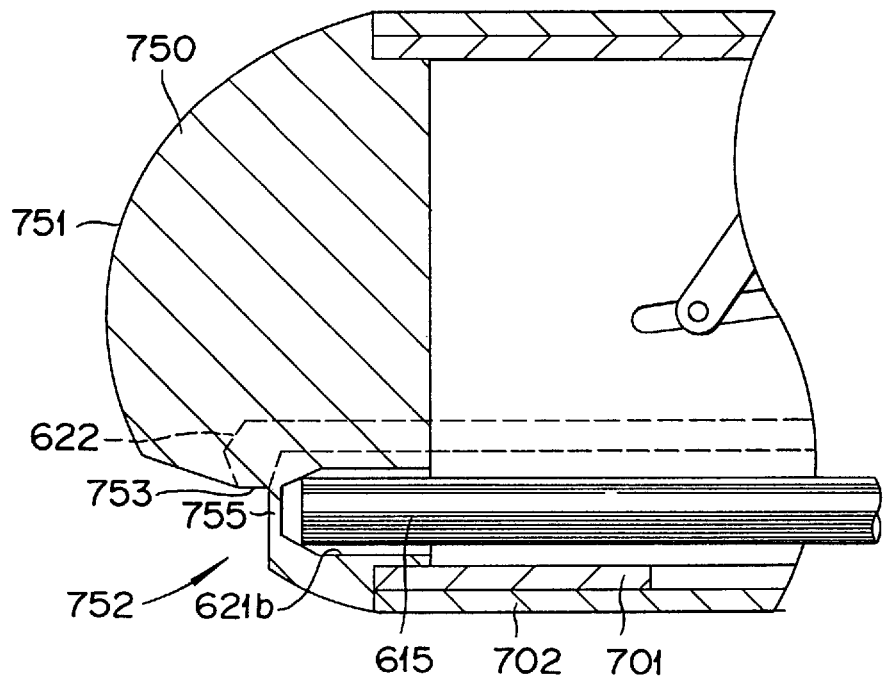
FIG. 38A is a cross section of the periphery of the end cap.
Figure 38B:
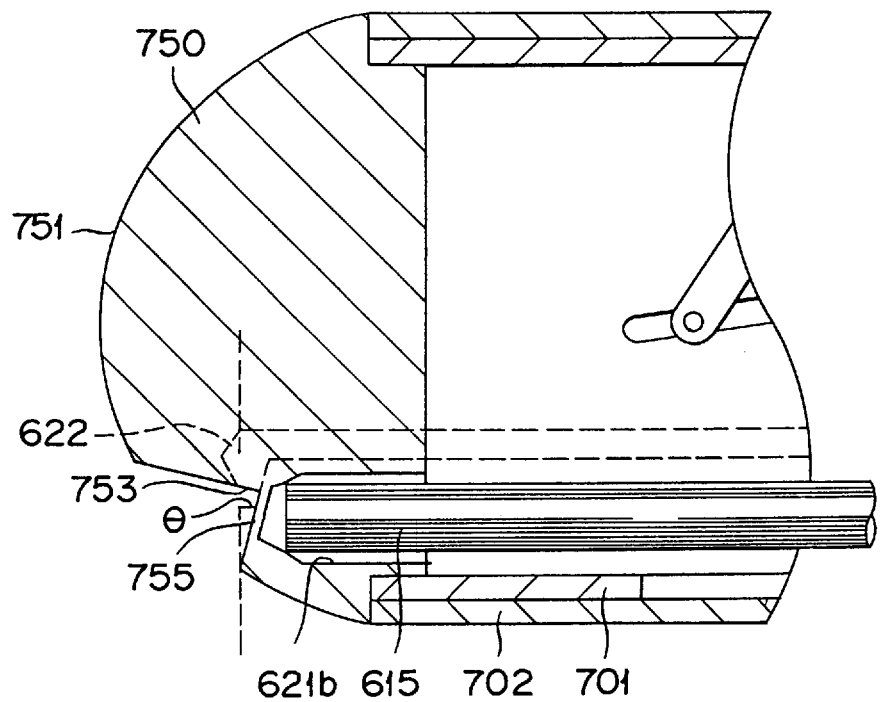
FIG. 38B is a cross section showing a variation of the end cap.

FIG. 38A is a cross section of the periphery of the end cap 750 and FIG. 38B is a cross section showing a variation of the end cap 750. An irrigation flush lumen 622 does not appear on the cross section for FIG. 38A and FIG. 38B in actuality, but is shown here to help understanding by dotted lines.

The end cap 750 has a smooth, quasi-semispherical part 751 creating no steps with the housing 701, so that it can be easily inserted into the living body. The housing 701 is covered by the covering member 702.

The end cap 750 contains the front observation window 755 that makes the front observation by the endoscope 615 possible. The front observation window 755 is located at a notched area 752 formed as a part of the quasi-semispherical part 751 of the end cap 750. The notched part 752 is formed in an outwardly expanding shape from the front observation window 755 toward the end cap 750 so that it does not hinder the view of the endoscope 615 provided via the front observation window 755. The end cap 750 and the front observation window 755 are formed as a single unit made of a transparent material that does not hinder the field of view of the endoscope 615, so that the number of parts is to be reduced. However, it is possible to make the end cap 750 and the front observation window 755 separately and affixed together. It is possible to have only the front observation window 755 be made of a transparent material in such a case.

The end cap 750 has an irrigation flow flushing port 753 for removing blood, body tissue fluid, and air bubbles attached on the outside of the front observation window 755. The irrigation flow flushing port 753 is formed to inject the irrigation flow directly onto the front observation window 755 in order to wash the front observation window 755 and its periphery efficiently. Thus, the soiled front observation window 755 can be cleaned and the observation by the endoscope 615 can be performed properly.

As shown in FIG. 38A, the irrigation flush port 753 is connected to the irrigation flush lumen 622 placed parallel to the longitudinal direction of the insertion part 700. The irrigation flush lumen 622 is formed inside the wall member 703 of the housing 701 as shown in FIG. 37. The irrigation flow is injected from an irrigation inlet port 623 as shown in FIG. 35. The irrigation flow should preferably be a fluid that is colorless, transparent, and harmless to the living organism, such as purified water or physiological saline.

The endoscope guide lumen 621b is formed on the end cap 750. The endoscope guide lumen 621b is provided to guide the endoscope 615 to the vicinity of the front observation window 755. The endoscope guide lumen 621b does not cause any problem in guiding the endoscope 615 to the front view window 755 as long as the endoscope 615 is shorter than the main body 620, but otherwise the endoscope 615 can cause damage to the front view window 755 by hitting it. As a preventive measure for such an accident, the diameter of the endoscope guide lumen 621b is tapered with the diameter near the front observation window 755 decreasing toward the front observation window 755.

Due to this tapering, the diameter of the endoscope guide lumen 621b is smaller than the diameter of the endoscope 615 in the vicinity of the front view window 755. Therefore, the endoscope 615 is caused to stop before it hits the front observation window 755 as it abuts against the inner wall of the endoscope guide lumen 621b. As can be seen from the above, the endoscope guide lumen 621b has a structure (tapering structure) to prevent the damage of the front observation window 755 by abutting of the endoscope 615. The range of the taper is not specifically limited as long as it is provided inside the end cap 750. The gradient of the tape is not specifically limited so long as it prevents the endoscope 615 from hitting the front observation window 755.

The front observation window 755 consists of a uniform and transparent flat surface. The front observation window 755 is constituted to be perpendicular or close to perpendicular to the optical axis of the endoscope 615 in order to prevent halation due to the endoscope guide light. The angle "close to perpendicular" means an angle shown as θ in FIG. 38B, which is an angle formed by the observation window 755 tilting toward the main body 620 side from a perpendicular line to the optical axis of the endoscope 615. The angle θ is 0° to 27°, or more preferably 10° to 15°, when the field of view angle of the endoscope 615 is 60°, the material of the front observation window is acrylic, and the coolant is water. The halation prevention angle θ is appropriately set according to the field of view angle, the window material and the coolant. By setting the angle of the front observation window 755 as shown above, the halation of the endoscope 615 can be prevented and the field of view can be maintained properly.

The cross sectional structure of the main body 620 will be described below with reference to FIG. 39.

Figure 39:
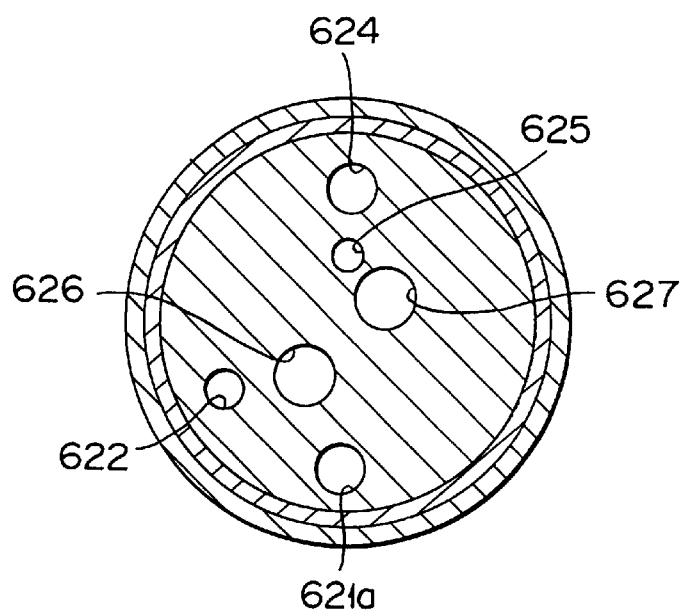
FIG. 39 is a cross section along the line F—F of FIG. 36.

FIG. 39 is a cross section along the line F—F of FIG. 36. In FIG. 39, the operating portion, the housing 701 and the covering member 702 are not shown for the sake of clarity.

Formed inside the main body 620 are: a lumen 624 for the arm, a lumen 625 for the optical fiber, a coolant supply lumen 626, a coolant discharge lumen 627, an endoscope guide lumen 621a, and the irrigation flush lumen 622. The lumen 624 for the arm is parallel to the axis of the main body 620, and the arm 720 reciprocates inside the lumen. The lumen 625 for the optical fiber is parallel to the axis of the main body 620, and the optical fiber 616 that is covered by the protective pipe reciprocates inside said lumen.

The coolant supply lumen 626 and the coolant discharge lumen 627 are provided for supplying and discharging the cooling fluid. The coolant supply lumen 626 is connected to the coolant circulating unit(cooling unit) via a tube 628 as shown in FIG. 35, and the coolant discharge lumen 627 is connected to the same via a tube 629. The coolant supply lumen 626 and the coolant discharge lumen 627 are both connected to the internal cavity (see FIG. 36) of the housing 701, in which the emission part 710 is placed. Therefore, the coolant sent in from the coolant circulating unit is guided into the internal space of the housing 701 via a tube 628 and the coolant supply lumen 626 to cool the surface of the tissue which is irradiated by the laser beam, the emission part 710, the covering member 702 through which the laser beam is transmitted, and other components of the unit. The coolant is returned to the coolant circulating unit via the coolant discharge lumen 627 and the tube 629.

The endoscope guide lumen 621a has the endoscope 615 inside it and allows it to reciprocate in it.

The irrigation flush lumen 622 transports the irrigation fluid from the irrigation inlet port 623 shown in FIG. 35. The irrigation flush lumen 622 is communicating from the inside of the main body 620 to the wall member 703 of the housing 701. The irrigation flush lumen 622 is not opened to the internal space of the housing 701 and opens only at the irrigation flush port 753 of the end cap 750. Therefore, the irrigation flush lumen 622 is entirely independent from the coolant inlet lumen 626 and the coolant discharge lumen 627. Therefore, the irrigation fluid and the cooling fluid can be separately guided.

It is preferable to prevent backflows of the coolant by providing check valves that are not shown in each of the lumens 621a, 624 and 625.

Figure 40:
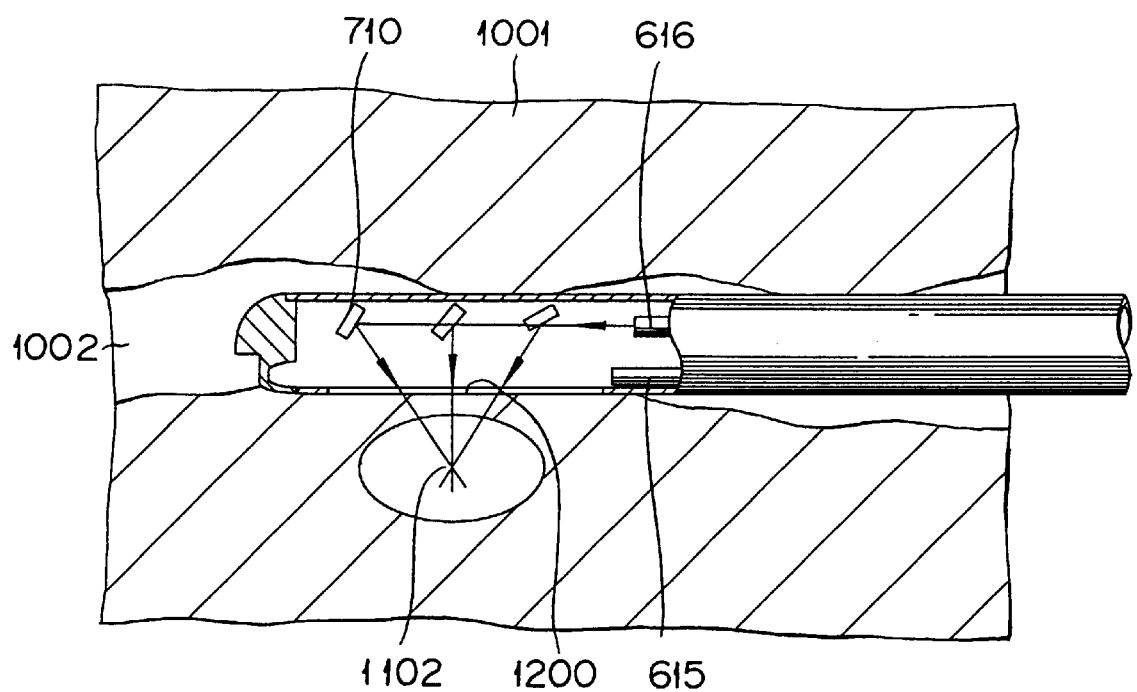
FIG. 40 is a conceptual drawing for describing how the laser beam irradiation unit is used.

The practical usage and the related actions of the laser irradiating unit lc will be described with reference cot FIG. 40. FIG. 40 is a conceptual drawing for describing how the laser beam irradiation unit 1C is used.

First, the insertion part 700 of the main body 620 of the laser irradiation unit lc is inserted into the body cavity 1002. The endoscope 615 is placed near the front observation window 755 and the approximate position of the target lesion is determined through front observations. Next, the housing 701 which contains the emission part 710 is made to contact closely against the surface layer in the vicinity of lesion, i.e., the target location 1102 to be heated.

Next, while confirming the vicinity of the target location 1102 by means of front observations through the front observation window 755 and side observations through the side window 704 appropriately moving the endoscope 615 along the endoscope guide lumen 621, the target location 1102 is accurately identified. In case of the target location 1102, the entire laser beam irradiation unit Ic is moved in the longitudinal direction of the main body 620 if there is a need for adjusting the position of the housing 701 in the longitudinal direction of the body cavity 1002. If there is a need for adjusting the housing 701 in the circumferential direction of the body cavity 1002, the entire laser beam irradiation apparatus 1c is rotated.

When the thermal treatment is started against the target location 1102, the coolant, whose temperature is adjusted in advance, is supplied from the coolant circulating unit via the tube 628 to the laser irradiation unit 1c and the laser beam generator will be activated. The generated laser beam is introduced into the laser irradiation unit 1c via a connector.

The laser beam is guided into the insertion part of the laser irradiation unit 1c via the optical fiber 616, reflected by the reflecting surface 711 of the emission part 710 in the housing 701, passes through the side window 704 and the covering member 702, and is irradiated on the target location 1102. The emission part 710 changes its irradiating angle as it reciprocates axially at the frequency of 1–6 Hz. Although the optical pass of the laser beam continuously changes but always passes through the target location 1102.

As a consequence, the target location 1102 inside the vital tissue 1001 and its vicinity generates more heat due to the continuous irradiation of the laser beam than other areas. Therefore, the target location 1102 reaches the desired temperature.

Areas above the target location 1102, for example, the surface layer 1200 of the vital tissue 1001, receive laser beam irradiations only intermittently so that they generate only a small amount of heat. Similarly, areas below the target location 1102 receive laser beam irradiations only intermittently so that they generate only a small amount of heat as well. In other words, the peripheral areas (normal areas) other than the target location 1102 are maintained at relatively low temperatures. Therefore, even if the target location 1102 is located deep inside the tissue, the damage to the areas other than the target location 1102 are prevented or minimized, while the target location 1102 is effectively heated. Thus, it provides a high safety to the patient. Moreover, the target location 1102 can be changed as desired, thus making it possible to heat any desired areas.

The laser beam can be arbitrary as long as it has good depth-reaching capabilities. The wavelength of the laser beam should preferably be 750 to 1300 nm or 1600 to 1800 nm.

The diameter of the insertion part of the laser irradiation unit 1c, in other words, the outer diameter of the main body 620 can be arbitrary as long as it can be inserted into the body cavity 1002. However, the diameter of the main body 620 should preferably be 2 to 20 mm, or more preferably, 3 to 8 mm.

As can be seen from the above, the laser beam irradiation unit 1c applied on the thermal treatment apparatus of this embodiment makes it possible to observe the lesion from the front observation window 755 and the side window 704, thus enabling easy and fast positioning of the housing 701.

It is of course also possible to control the operating condition of the laser beam generators as shown in the first through fourth embodiments using the laser beam irradiation unit 1c of this embodiment.

Since the endoscope guide lumen 621b is tapered, there is no possibility that the endoscope 615 to hit the front observation window 755. Moreover, the laser beam irradiation unit 1c of this embodiment is capable of thermally treating only the inside of the prostate even if normal tissues such as the urethra and the rectum exist in the vicinity of the prostate such as in the case of benign prostatic hyperplasia and prostate cancer.

Figure 41:
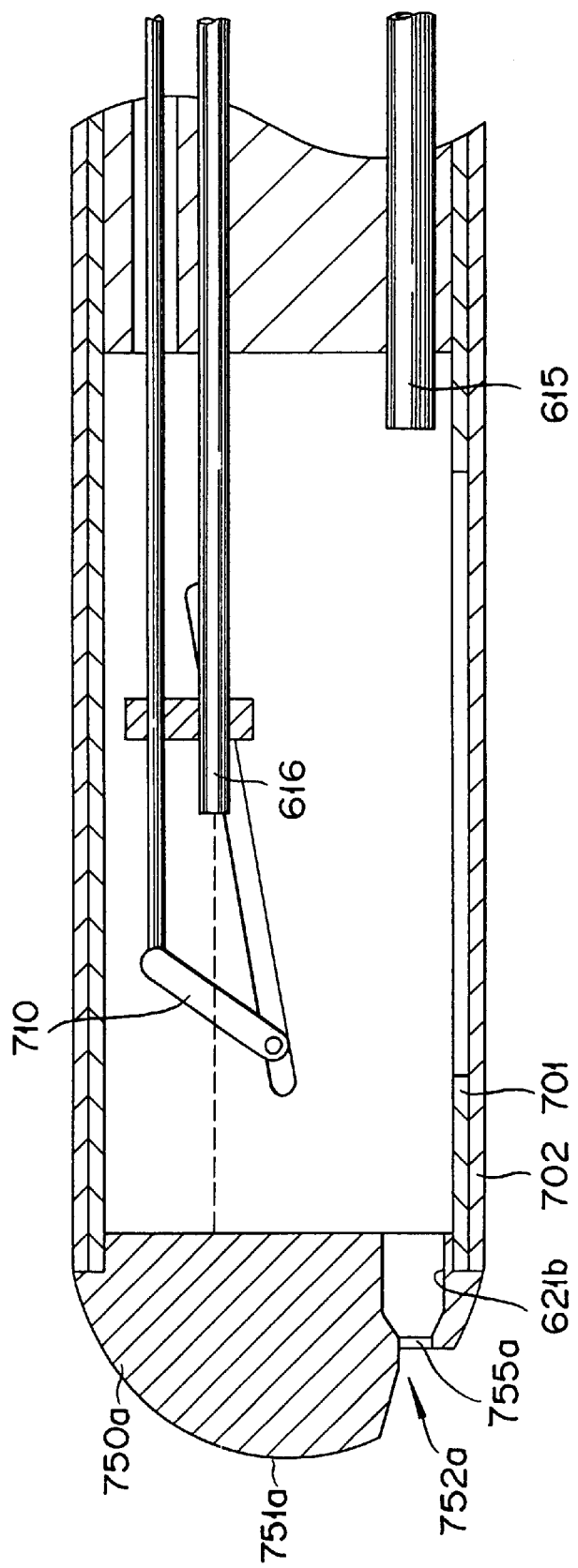
FIG. 41 is a drawing showing the end cap of the laser beam irradiation unit used on the thermal treatment apparatus concerning the seventh embodiment of the invention.

FIG. 41 is a drawing showing the end cap of the laser beam irradiation unit used on the thermal treatment apparatus concerning the seventh embodiment of the invention.

The only difference between the seventh embodiment and the sixth embodiment is the end cap, so that the end cap will be described with reference to FIG. 41. All other components that are similar to those in the sixth embodiment are assigned with the same numbers and their descriptions are not repeated here.

In FIG. 41, an end cap 750a is made of a material that filters out the laser beam supplied by the optical fiber 616. The end cap 750a has a smooth, quasi-semispherical part 751a creating no steps with the housing 701, so that it can be easily inserted into the living body. The end cap 750a also has a front observation window 755a.

The front observation window 755a is made of a transparent material that does not prevent the field of view of the endoscope 615. The front observation window 755a is located at a notched area 752a formed as a part of the quasi-semispherical part 751a. The notched part 752a is formed in an outwardly expanding shape from the front observation window 755a toward the end cap 750a so that it does not hinder the view of the endoscope 615 provided via the front observation window 755a.

Since the end cap 750a is made of a material that filters out laser beams so that it does not cause any leakage of laser beams out of the end cap 750a even when the emission part 710 is damaged and laser beams go straight without being reflected.

It is obvious that this invention is not limited to the particular embodiments shown and described above but may be variously changed and modified without departing from the technical concept of this invention.

Although laser beams are used as an example of the energy to be irradiated at vital tissues in the embodiments described above, the invention is not limited to it. The energies to be used can be microwave, radio frequency, ultrasound, etc.

Although prostatic hyperplasia is used as an example of the tissue to be treated in the above descriptions, the invention is not limited to it and the applicable tissues include all kinds of tissues that can be thermally treated by irradiating energy either via a body cavities or lumens such as blood vessel, digestive tubes (esophagus, bowel, etc.) and abdominal cavity or from the body surface.

The energy output unit can be constituted in such a way that it has a shape that allows it to be inserted in the urethra and that the energy output direction faces toward a location in the prostate as the unit is inserted into the urethra; the thermal treatment unit can consist of a urethra temperature detection member that detects the temperature of the urethra wall and a rectum temperature detection member that detects the rectum wall, both of which being provided in the energy output unit; and the energy control unit can be constituted to control the operating condition of the energy supply unit based on the detection results of the urethra temperature detection member and the rectum temperature detection member.

It can also be equipped with an optical detection member that is provided at the energy output unit and optically detects whether said energy output unit is abutting with the energy output object, and the energy control unit controls the operating condition of the energy supply unit using the detection result of the optical detection member. Such a control can be independently executed or can be executed in combination with the control of each embodiment.

The thermal treatment apparatus can be constituted to have a refrigerant container that holds the refrigerant, a refrigerant supply pass and a refrigerant collection pass that connects between the refrigerant container and the energy output unit, a refrigerant send out unit for sending out the refrigerant to the energy output unit, a cooling unit that cools the refrigerant, and a refrigerant control unit that adjust the flow and temperature of the refrigerant by controlling the operating conditions of the refrigerant sending out unit and the cooling unit.

The refrigerant container can be constituted to have a first side, a second side parallel to the first side, and the cooling unit can be constituted to have a first cooling unit that contacts with the first side of the refrigerant container and a second cooling unit that is mounted detachably on the second side of the refrigerant container.

The thermal treatment apparatus can be constituted to have a lumen that extends in the longitudinal direction inside the energy output unit and opens in the vicinity of the distal end of said energy output unit, and an observation member that can be inserted into said lumen in order to observe the living body.

This application is based on Japanese patent Application No. 2000-201644 filed on Jul. 3, 2000, the contents of which are hereby incorporated by reference.

What is claimed is:

1. A thermal treatment apparatus, for thermally treating a vital tissue by means of applying energy, comprising:
   an energy supply unit for supplying energy for treatment;
   an energy output unit that is connected to said energy supply unit and has an energy reflection member for reflecting energy supplied by said energy supply unit;
   a drive unit that changes the position and angle of said energy reflection member;
   a detection unit that detects information concerning emission function of energy emitted by being reflected by said energy reflection member; and
   an energy control unit controlling operating conditions of said energy supply unit based on said detection unit detection results; and
   wherein said detection unit detects said energy reflection member temperature.

2. A thermal treatment apparatus as claimed in claim 1, wherein said detection unit is provided in areas of said energy reflection member except a reflection surface of the energy reflection member where the energy is received.

3. A thermal treatment apparatus as claimed in claim 2, wherein said detection unit is provided on a back of the reflection surface of said energy reflection member.

4. A thermal treatment apparatus for thermally treating a vital tissue by means of applying energy, comprising:
   an energy supply unit for supplying energy for treatment;
   an energy output unit that is connected to said energy supply unit and has an energy reflection member for reflecting energy supplied by said energy supply unit;
   a drive unit that changes the position and angle of said energy reflection member;
   a detection unit that detects information concerning emission function of energy emitted by being reflected by said energy reflection member; and
   an energy control unit controlling operating conditions of said energy supply unit based on said detection unit detection results; and
   a monitoring unit for monitoring operating conditions of said drive unit; wherein
      said energy control unit controls operating conditions of said energy supply unit using output results from said monitoring unit.

5. A thermal treatment apparatus for thermally treating a vital tissue by means of applying energy, comprising:
   an energy supply unit for supplying energy for treatment;
   an energy output unit that is connected to said energy supply unit and has an energy reflection member for reflecting energy supplied by said energy supply unit;
   a drive unit that changes the position and angle of said energy reflection member;
   a detection unit that detects information concerning emission function of energy emitted by being reflected by said energy reflection member; and
   an energy control unit controlling operating conditions of said energy supply unit based on said detection unit detection results; and
   wherein said detection unit detects reciprocating motion of said energy reflection member.

6. A thermal treatment apparatus as claimed in claim 5, wherein
   said detection unit has an energy detection member for detecting energy emitted by said energy reflection member when said energy reflecting member is at a specified position, thus detecting said energy reflection member's reciprocating motion by measuring time intervals between said energy detection member's detections.

7. A thermal treatment apparatus as claimed in claim 5, wherein
   said detection unit has a position detection member for detecting whether said energy reflection member is at a specified position, thus detecting said energy reflection member's reciprocating motion by measuring time intervals between said position detection member's detections.

8. A thermal treatment apparatus as claimed in claim 5, wherein
   said detection unit has a position detection member for detecting whether said energy reflection member is at a first position and an energy detection member for detecting energy emitted by said energy reflection member when said energy reflecting member is at a second position, thus detecting said energy reflection member's reciprocating motion by measuring time intervals at said position detection member and said energy detection member.

9. A thermal treatment apparatus as claimed in claim 5, wherein
   said detection unit further detects surface temperature of the vital tissues being thermally treated.

10. A thermal treatment apparatus as claimed in claim 9, wherein said detection unit has a single energy detection member for detecting energy emitted by said energy reflection member when said energy reflecting member is at a specified position, thus detecting said energy reflection member's reciprocating motion by measuring time intervals between said energy detection member's detections as well as detecting said vital tissues' surface temperature by means of said energy detection member.

11. A thermal treatment apparatus as claimed in claim 9, further comprising
a diagnosis unit for performing diagnosis concerning emission functions of the energy emitted by said energy reflection member.

12. A thermal treatment apparatus as claimed in claim 5, further comprising
a wall member on which a pair of grooves are formed for supporting slidably protrusions provided on both sides of said energy reflection member, wherein
said wall member has a containing part for storing said detection unit.

13. A thermal treatment apparatus as claimed in claim 5, wherein
said detection unit has either an optical sensor or a temperature sensor.

14. A thermal treatment apparatus as claimed in claim 5, wherein said energy supply unit supplies laser beams as the energy.

15. A thermal treatment apparatus as claimed in claim 5, wherein
said energy output unit comprises:
  a long and slender insertion part that is provided with said energy reflection member and can be inserted into a living body;
  an endoscope that is inserted into said insertion part for observing vital tissues; and
  a front observation window and a side observation window for making it possible to observe the front and side directions of said insertion part by means of said endoscope.

16. A thermal treatment apparatus as claimed in claim 15, wherein
said energy output unit further comprises:
  a guide lumen for supporting said endoscope so that it can move from proximal side of said insertion part to said front observation window's vicinity.

17. A thermal treatment apparatus as claimed in claim 15, wherein
said energy output unit further comprises:
  a prevention part that prevents said endoscope from contacting with said front observation window.

18. A thermal treatment apparatus as claimed in claim 17, wherein
said prevention part has a tapered construction formed to reduce diameter toward said front observation window, wherein the distal end diameter of said tapered construction is smaller than the endoscope's diameter.

19. A thermal treatment apparatus as claimed in claim 15, wherein
said endoscope has a filter that prevents said energy from passing.

20. A thermal treatment apparatus as claimed in claim 15, wherein
said front observation window is perpendicular to or tilting from perpendicular to an optical axis of said endoscope by an angle smaller than a specified angle.

21. A thermal treatment apparatus as claimed in claim 15, wherein
said front observation window is formed on an end cap provided at a tip of said insertion part and said end cap has a spherical smooth shape.

22. A thermal treatment apparatus as claimed in claim 21, wherein
said end cap has an irrigation outlet port for releasing irrigation liquid for washing said front observation window's outer periphery; and
said insertion part has an irrigation liquid passage to guide the irrigation liquid to said irrigation outlet port.

23. A thermal treatment apparatus as claimed in claim 22, wherein
said insertion part has a coolant passage to guide coolant for cooling said energy reflection member and said insertion part's surface; and
said irrigation liquid passage and said coolant passage are formed independently inside said insertion part.

24. A thermal treatment apparatus as claimed in claim 21, wherein
said end cap is formed integrally with said front observation window.

25. A thermal treatment apparatus as claimed in claim 21, wherein
said end cap is made of a material that filters out laser beams in areas except in a vicinity of said front observation window of said end cap.

* * * * *